US006147055A

United States Patent [19]

[11] Patent Number: 6,147,055

[45] Date of Patent: *Nov. 14, 2000

Hobart et al.

[54] CANCER TREATMENT METHOD UTILIZING PLASMIDS SUITABLE FOR IL-2 EXPRESSION

[75] Inventors: Peter M. Hobart, Poway; Michal Margalith, Solana Beach; Suezanne E. Parker, San Diego; Shirin Khatibi, Carlsbad, all of Calif.

[73] Assignee: Vical Incorporated, San Diego, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/818,562

[22] Filed: Mar. 14, 1997

Related U.S. Application Data

[63] Continuation of application No. 08/345,913, Nov. 28, 1994, Pat. No. 5,641,665.

[51] Int. Cl.[7] .................................................. A61K 48/00

[52] U.S. Cl. ...................... 514/44; 536/23.52; 435/320.1

[58] Field of Search ............................... 435/69.1, 172.3, 435/320.1; 514/44; 530/329, 350; 536/23.1, 23.4, 23.5, 24.1; 935/23, 66

[56] References Cited

U.S. PATENT DOCUMENTS

| | | | |
|---|---|---|---|
| 4,738,927 | 4/1988 | Taniguchi et al. . | |
| 4,992,367 | 2/1991 | Cullen et al. | 435/69.52 |
| 5,122,458 | 6/1992 | Post et al. . | |
| 5,168,062 | 12/1992 | Stinski . | |
| 5,229,109 | 7/1993 | Grimm et al. | 424/85.2 |
| 5,250,296 | 10/1993 | Ootsu | 424/85.2 |
| 5,264,618 | 11/1993 | Felgner et al. | 560/224 |
| 5,328,470 | 7/1994 | Nabel et al. | 604/101 |
| 5,459,127 | 10/1995 | Felgner et al. | 514/7 |
| 5,589,466 | 12/1996 | Felgner et al. | 514/44 |
| 5,641,665 | 6/1997 | Hobart et al. | 435/172.3 |
| 5,693,622 | 12/1997 | Wolff et al. | 514/44 |
| 5,703,055 | 12/1997 | Felgner et al. | 514/44 |

FOREIGN PATENT DOCUMENTS

| | | |
|---|---|---|
| 2190382A | 11/1987 | United Kingdom . |
| 8901036 | 2/1989 | WIPO . |
| 9324640 | 12/1993 | WIPO . |

OTHER PUBLICATIONS

Galanis et al. J. Clin. Oncology, vol. 17, pp. 3313–3323, 1999.

Stuart H. Orkin, and Arno G. Motulsky. "Report and Recommendations of the Panel to Assess the NIH investment in Research on Gene Therapy", Dec. 7, 1995.

Tomlinson et al. J. Controlled Release, vol. 39, pp. 357–372, 1996.

Crystal Science, vol. 270, pp. 404–410, 1995.

Orkin Report and Recommendations of the panel to assess the NIH investment in research on gene therapy, Dec. 7, 1995.

Hanania et al. Am. J. Med., vol. 99, pp. 537–552, Nov. 1995.

Mulligan, Science, vol. 260, pp. 926–932, May 14, 1993.

Vieweg et al. Cancer Invest., vol. 13, pp. 193–201, 1995.

Blaese et al. Scientific American, vol. 276, pp. 111–115, Jun. 1997.

Verma et al. Nature, vol. 389, pp. 239–242, 1997.

Manthorpe et al. Human Gene Therapy, vol. 4, p. 419–431, 1993.

Montgomery et al. DNA and Cell Biology, vol. 12, pp. 777–783, 1993.

San et al. Human Gene therapy, vol. 4, pp. 781–788, 1993.

Berg, D. et al. (1978) In Microbiology [Schelessinger, D. ed.] pp. 13–15 American Society for Microbiology, Washington D.C.

(List continued on next page.)

*Primary Examiner*—John L. LeGuyader
*Assistant Examiner*—Michael C. Wilson
*Attorney, Agent, or Firm*—Sterne, Kessler, Goldstein & Fox

[57] ABSTRACT

The present invention relates to plasmids suitable for IL-2 expression, particularly, human IL-2 expression, and related methods.

24 Claims, 21 Drawing Sheets

CMV Promoter/Enhnacer
Kanamycin r
CMV IE1 5'UT AND Intron1
pUC18 ori
HUMAN 1L-2
BGH Term.

OTHER PUBLICATIONS

Bolivar, F. et al. (1977) Construction and characterization of new cloning vehicles II. A multipurpose cloning system. Gene 2:95–113.

Chapman, B. et al. (1991) Effect of intron A from human cytomegalovirus (Towne) immediate–early gene on heterologous expression in mammalian cells. Nucleic Acids Research 19(14):3979–3986.

Cullen, B. et al. (1988) Expression of a cloned human interleukin–2 cDNA is enhanced by the substitution of a heterologous mRNA leader region. DNA 7(9) 645–650.

Gansbacher, B. et al. (1990) Interleukin 2 gene transfer into tumor cells abrogates tumorigenicity and induces protective immunity. J. Exp. Med. 172:1217–1224.

Gansbacher, B. et al. (1992) Retroviral gene transfer induced constitutive expression of interleukin–2–or interferon . . . Blood 80(11):2817–2825.

LaFemina, R. et al. (1980) Structural organization of the DNA molecules from human cytomegalovirus. Animal Virus Genetics 39–55.

Lewin, R. (1987) When does not homology mean something else. Science 237:1570.

Manthorpe, M., et al. (1993) Gene therapy by intramuscular injection of plasmid DNA: studies on firefly luciferase gene expression in mice. Human Gene Therapy 4:419–431.

Margalith, M., et al. (1995) VCL1102: A plasmid DNA vector to effect high levels of IL–2 expression in vivo. Journal of Cellular Biochemistry Supplement 21A, see abstract C6–534.

Montogomery, D., et al. (1993) Heterologous and homologous protection against influenza A by DNA vaccination: optimization of DNA vectors. DNA and Cell Biology 12(9): 777–783.

Nabel, G., et al. (1994) Immunotherapy for cancer by direct gene transfer into tumors. Human Gene Therapy 5:57–77.

Nabel, G., et al. (1993) Direct gene transfer with DNA–liposome complexes in melanoma: expression, biologic activity, and lack of toxicity in humans. Proc. Natl. Acad. Sci. 90:11307–11311.

Oka, A. et al. (1981) Nucleotide sequence of the kanamycin resistance transposon Tn903. J. Mol. Biol. 147:217–226.

O'Quigley, J. et al. (1991) Methods for dose finding studies in cancer clinical trials: a review and results of a monte carlo study. Statistics in Medicine 10:1647–1664.

O'Quigley, J. et al. (1990) Continual reassessment method: a practical design for phase I clinical trials in cancer. Biometrics 46:33–48.

Orkin, S., et al. Report and recommendations of the panel to assess the NIH investment in research on gene therapy. Dec. 7, 1995.

Parker, S., et al. (1994) Direct delivery of cytokine genes into tumors for cancer immunotherapy. Journal of Cellular Biochemistry Supplement 18A, see abstract DZ 414.

Plautz, G., et al. (1993) Immunotherapy of malignancy by in vivo gene transfer into tumors. Proc. Natl. Acad Sci. 90:4645–4649.

Reeck, G.R., et al. (1987) Homology in proteins and nucleic acids: a terminology muddle and a way out of it. Cell 50:667.

San, H., et al. (1993) Safety and short–term toxicity of a novel cationic lipid formulation for human gene therapy. Human Gene Therapy 4:781–788.

Storer, B. (1989) Design and analysis of phase I clinical trial. Biometrics 45:925–937.

Vile, R.G., and Hart, I.R. (1994) Targeting of cytokine gene expression to malignant melanoma cell using tissue specific promoter sequences. Annals of Oncology 5 (Suppl 5):S59–S65.

Wardley, R., et al. (1992) The use of feline herpesvirus and baculovirus as vaccine vectors for the gag and env genes of feline leukaemia virus. Journal of General Virology 73:1811–1818.

% VOLUME: CONTROL
100
90
80
70
60
50
40
30
20
10
0
SALINE
IL2 PLASMID 50UG
IL2 PLASMID 10UG
IL2 PLASMID 2UG
IL2 PLASMID 0.4UG
IL2 PLASMID/DM 50UG
IL2 PLASMID/DM 10UG
IL2 PLASMID/DM 2UG
IL2 PLASMID/DM 0.4UG
IL2 PLASMID/BAE 50UG
IL2 PLASMID/BAE 10UG
IL2 PLASMID/BAE 2UG
IL2 PLASMID/BAE 0.4UG
IL2 PLASMID/BAE 0.4UG ng/~1x10e6 Cells (35mm Well)
250
200
150
100
50
0
Lipid Only
CMVBGH
RSVIL2SV40
CMVIL2BGH
Plasmid DNA

SEQUENCE LISTING

<160> NUMBER OF SEQ ID NOS: 3

<210> SEQ ID NO 1
<211> LENGTH: 4928
<212> TYPE: DNA
<213> ORGANISM: Homo sapiens
<220> FEATURE:
<221> NAME/KEY: CDS
<222> LOCATION: (1689)..(2159)

<400> SEQUENCE: 1
cattgcatac gttgtatcta tatcataata tgtacattta tattggctca tgtccaatat 60
gaccgccatg ttgacattga ttattgacta gttattaata gtaatcaatt acggggtcat 120
tagttcatag cccatatatg gagttccgcg ttacataact tacggtaaat ggcccgcctg 180
gctgaccgcc caacgacccc cgcccattga cgtcaataat gacgtatgtt cccatagtaa 240
cgccaatagg gactttccat tgacgtcaat gggtggagta tttacggtaa actgcccact 300
tggcagtaca tcaagtgtat catatgccaa gtccggcccc ctattgacgt caatgacggt 360
aaatggcccg cctggcatta tgcccagtac atgaccttac gggactttcc tacttggcag 420
tacatctacg tattagtcat cgctattacc atggtgatgc ggttttggca gtacaccaat 480
gggcgtggat agcggtttga ctcacgggga tttccaagtc tccaccccat tgacgtcaat 540
gggagtttgt tttggcacca aaatcaacgg gactttccaa aatgtcgtaa taaccccgcc 600
ccgttgacgc aaatgggcgg taggcgtgta cggtgggagg tctatataag cagagctcgt 660
ttagtgaacc gtcagatcgc ctggagacgc catccacgct gttttgacct ccatagaaga 720
caccgggacc gatccagcct ccgcggccgg gaacggtgca ttggaacgcg gattccccgt 780
gccaagagtg acgtaagtac cgcctataga ctctataggc acacccettt ggctcttatg 840 catgctatac tgtttttggc ttggggccta tacacccccg cttccttatg ctataggtga 900
tggtatagct tagcctatag gtgtgggtta ttgaccatta ttgaccactc ccctattggt 960
gacgatactt tccattacta atccataaca tggctctttg ccacaactat ctctattggc 1020
tatatgccaa tactctgtcc ttcagagact gacacggact ctgtattttt acaggatggg 1080
gtcccattta ttatttacaa attcacatat acaacaacgc cgtcccccgt gcccgcagtt 1140
tttattaaac atagcgtggg atctccacgc gaatctcggg tacgtgttcc ggacatgggc 1200
tcttctccgg tagcggcgga gcttccacat ccgagccctg gtcccatgcc tccagcggct 1260
catggtcgct cggcagctcc ttgctcctaa cagtggaggc cagacttagg cacagcacaa 1320
tgcccaccac caccagtgtg ccgcacaagg ccgtggcggt agggtatgtg tctgaaaatg 1380
agctcggaga ttgggctcgc accgctgacg cagatggaag acttaaggca gcggcagaag 1440
aagatgcagg cagctgagtt gttgtattct gataagagtc agaggtaact cccgttgcgg 1500
ttgctgttaa cggtggaggg cagtgtagtc tgagcagtac tcgttgctgc cgcgcgcgcc 1560
accagacata atagctgaca gactaacaga ctgttccttt ccatgggtct tttctgcagt 1620
caccgtcgtc gacacgtgtg atcagatcta gcctcaaccc tgactatctt ccaggtcatt 1680 gttccaac atg gcc ctg tgg atc gac agg atg caa ctc ctg tct tgc att 1730
Met Ala Leu Trp Ile Asp Arg Met Gln Leu Leu Ser Cys Ile
1 5 10 gca cta agt ctt gca ctt gtc aca aac agt gca cct act tca agt tct 1778
Ala Leu Ser Leu Ala Leu Val Thr Asn Ser Ala Pro Thr Ser Ser Ser
15 20 25 30

-continued

```
aca aag aaa aca cag cta caa ctg gag cat tta ctg ctg gat tta cag     1826
Thr Lys Lys Thr Gln Leu Gln Leu Glu His Leu Leu Leu Asp Leu Gln
                 35                  40                  45

atg att ttg aat gga att aat aat tac aag aat ccc aaa ctc acc agg     1874
Met Ile Leu Asn Gly Ile Asn Asn Tyr Lys Asn Pro Lys Leu Thr Arg
             50                  55                  60

atg ctc aca ttt aag ttt tac atg ccc aag aag gcc aca gaa ctg aaa     1922
Met Leu Thr Phe Lys Phe Tyr Met Pro Lys Lys Ala Thr Glu Leu Lys
         65                  70                  75

cat ctt cag tgt cta gaa gaa gaa ctc aaa cct ctg gag gaa gtg cta     1970
His Leu Gln Cys Leu Glu Glu Glu Leu Lys Pro Leu Glu Glu Val Leu
     80                  85                  90

aat tta gct caa agc aaa aac ttt cac tta aga ccc agg gac tta atc     2018
Asn Leu Ala Gln Ser Lys Asn Phe His Leu Arg Pro Arg Asp Leu Ile
 95                 100                 105                 110

agc aat atc aac gta ata gtt ctg gaa cta aag gga tct gaa aca aca     2066
Ser Asn Ile Asn Val Ile Val Leu Glu Leu Lys Gly Ser Glu Thr Thr
                115                 120                 125

ttc atg tgt gaa tat gct gat gag aca gca acc att gta gaa ttt ctg     2114
Phe Met Cys Glu Tyr Ala Asp Glu Thr Ala Thr Ile Val Glu Phe Leu
            130                 135                 140

aac aga tgg att acc ttt tgt caa agc atc atc tca aca ctg act         2159
Asn Arg Trp Ile Thr Phe Cys Gln Ser Ile Ile Ser Thr Leu Thr
        145                 150                 155

tgataattaa gtgcttccca cttaaaacat atcagggatc tcgactctag aggatcatcg   2219

cggccgctct agaccaggcg cctggatcca gatctgctgt gccttctagt tgccagccat   2279

ctgttgtttg cccctccccc gtgccttcct tgaccctgga aggtgccact cccactgtcc   2339

tttcctaata aaatgaggaa attgcatcgc attgtctgag taggtgtcat tctattctgg   2399

ggggtggggt ggggcaggac agcaaggggg aggattggga agacaatagc aggcatgctg   2459

gggatgcggt gggctctatg ggtacccagg tgctgaagaa ttgacccggt tcctcctggg   2519

ccagaaagaa gcaggcacat ccccttctct gtgacacacc ctgtccacgc ccctggttct   2579

tagttccagc cccactcata ggacactcat agctcaggag ggctccgcct tcaatcccac   2639

ccgctaaagt acttggagcg gtctctccct ccctcatcag cccaccaaac caaacctagc   2699

ctccaagagt gggaagaaat taaagcaaga taggctatta agtgcagagg gagagaaaat   2759

gcctccaaca tgtgaggaag taatgagaga aatcatagaa ttcgtaatca tgtcatagct   2819

gtttcctgtg tgaaattgtt atccgctcac aattccacac aacatacgag ccggaagcat   2879

aaagtgtaaa gcctggggtg cctaatgagt gagctaactc acattaattg cgttgcgctc   2939

actgcccgct ttccagtcgg gaaacctgtc gtgccagctg cattaatgaa tcggccaacg   2999

cgcggggaga ggcggtttgc gtattgggcg ctcttccgct tcctcgctca ctgactcgct   3059

gcgctcggtc gttcggctgc ggcgagcggt atcagctcac tcaaaggcgg taatacggtt   3119

atccacagaa tcaggggata acgcaggaaa gaacatgtga gcaaaaggcc agcaaaaggc   3179

caggaaccgt aaaaaggccg cgttgctggc gtttttccat aggctccgcc cccctgacga   3239

gcatcacaaa aatcgacgct caagtcagag gtggcgaaac ccgacaggac tataaagata   3299

ccaggcgttt ccccctggaa gctccctcgt gcgctctcct gttccgaccc tgccgcttac   3359

cggatacctg tccgcctttc tcccttcggg aagcgtggcg ctttctcata gctcacgctg   3419

taggtatctc agttcggtgt aggtcgttcg ctccaagctg ggctgtgtgc acgaaccccc   3479

cgttcagccc gaccgctgcg ccttatccgg taactatcgt cttgagtcca acccggtaag   3539

acacgactta tcgccactgg cagcagccac tggtaacagg attagcagag cgaggtatgt   3599
```

-continued

```
aggcggtgct acagagttct tgaagtggtg gcctaactac ggctacacta gaaggacagt   3659

atttggtatc tgcgctctgc tgaagccagt taccttcgga aaaagagttg gtagctcttg   3719

atccggcaaa caaaccaccg ctggtagcgg tggttttttt gtttgcaagc agcagattac   3779

gcgcagaaaa aaaggatctc aagaagatcc tttgatcttt tctacggggt ctgacgctca   3839

gtggaacgaa aactcacgtt aagggatttt ggtcatgaac aataaaactg tctgcttaca   3899

taaacagtaa tacaaggggt gttatgagcc atattcaacg ggaaacgtct tgctcgaggc   3959

cgcgattaaa ttccaacatg gatgctgatt tatatgggta taaatgggct cgcgataatg   4019

tcgggcaatc aggtgcgaca atctatcgat tgtatgggaa gcccgatgcg ccagagttgt   4079

ttctgaaaca tggcaaaggt agcgttgcca atgatgttac agatgagatg gtcagactaa   4139

actggctgac ggaatttatg cctcttccga ccatcaagca ttttatccgt actcctgatg   4199

atgcatggtt actcaccact gcgatccccg ggaaaacagc attccaggta ttagaagaat   4259

atcctgattc aggtgaaaat attgttgatg cgctggcagt gttcctgcgc cggttgcatt   4319

cgattcctgt ttgtaattgt ccttttaaca gcgatcgcgt atttcgtctc gctcaggcgc   4379

aatcacgaat gaataacggt ttggttgatg cgagtgattt tgatgacgag cgtaatggct   4439

ggcctgttga acaagtctgg aaagaaatgc ataagctttt gccattctca ccggattcag   4499

tcgtcactca tggtgatttc tcacttgata accttatttt tgacgagggg aaattaatag   4559

gttgtattga tgttggacga gtcggaatcg cagaccgata ccaggatctt gccatcctat   4619

ggaactgcct cggtgagttt tctccttcat tacagaaacg gctttttcaa aaatatggta   4679

ttgataatcc tgatatgaat aaattgcagt ttcatttgat gctcgatgag tttttctaag   4739

aattcgccat tcgccattca ggctgcgcaa ctgttgggaa gggcgatcgg tgcgggcctc   4799

ttcgctatta cgccagctgg cgaaaggggg atgtgctgca aggcgattaa gttgggtaac   4859

gccagggttt tcccagtcac gacgttgtaa aacgacggcc agtgccaagc tttttgcaaa   4919

agcctaggc                                                           4928
```

```
<210> SEQ ID NO 2
<211> LENGTH: 157
<212> TYPE: PRT
<213> ORGANISM: Homo sapiens

<400> SEQUENCE: 2

Met Ala Leu Trp Ile Asp Arg Met Gln Leu Leu Ser Cys Ile Ala Leu
  1               5                  10                  15

Ser Leu Ala Leu Val Thr Asn Ser Ala Pro Thr Ser Ser Ser Thr Lys
             20                  25                  30

Lys Thr Gln Leu Gln Leu Glu His Leu Leu Leu Asp Leu Gln Met Ile
         35                  40                  45

Leu Asn Gly Ile Asn Asn Tyr Lys Asn Pro Lys Leu Thr Arg Met Leu
     50                  55                  60

Thr Phe Lys Phe Tyr Met Pro Lys Lys Ala Thr Glu Leu Lys His Leu
 65                  70                  75                  80

Gln Cys Leu Glu Glu Glu Leu Lys Pro Leu Glu Glu Val Leu Asn Leu
                 85                  90                  95

Ala Gln Ser Lys Asn Phe His Leu Arg Pro Arg Asp Leu Ile Ser Asn
            100                 105                 110

Ile Asn Val Ile Val Leu Glu Leu Lys Gly Ser Glu Thr Thr Phe Met
        115                 120                 125
```

-continued

```
Cys Glu Tyr Ala Asp Glu Thr Ala Thr Ile Val Glu Phe Leu Asn Arg
    130                 135                 140

Trp Ile Thr Phe Cys Gln Ser Ile Ile Ser Thr Leu Thr
145                 150                 155


<210> SEQ ID NO 3
<211> LENGTH: 6
<212> TYPE: PRT
<213> ORGANISM: Homo sapiens

<400> SEQUENCE: 3

Met Ala Leu Trp Ile Asp
  1               5
```

CANCER TREATMENT METHOD UTILIZING PLASMIDS SUITABLE FOR IL-2 EXPRESSION

This application is a continuation of U.S. patent application Ser. No. 08/345,913, filed Nov. 28, 1994, now U.S. Pat. No. 5,641,665.

FIELD OF THE INVENTION

The present invention relates to plasmids suitable for IL-2 expression, particularly human IL-2 expression, and related methods.

BACKGROUND OF THE INVENTION

Recent advances in our understanding of the biology of the immune system have led to the identification of important modulators of immune responses. Agents known as cytokines mediate many of the immune responses involved in antitumor activity. Several of these cytokines have been produced by recombinant DNA methodology and evaluated for their antitumor effects. In clinical trials, the administration of cytokines has resulted in objective tumor responses in patients with various types of neoplasms.

Interleukin 2 (IL-2) is an important cytokine in the generation of antitumor immunity. In response to tumor antigens, helper T-cells secrete local amounts of IL-2. This IL-2 acts locally at the site of tumor antigen stimulation to activate cytotoxic T-cells (CTL) and natural killer cells (NK), cellular immune activity which may mediate systemic tumor cell destruction.

Intravenous, intralymphatic, or intralesional administration of IL-2 has resulted in clinically significant responses in some cancer patients. However, severe toxicities (e.g., hypotension, pulmonary edema, prerenal azotemia, cardiac arrhythmias and myocardial infarction) limit the dose and efficacy of systemic IL-2 administration. The toxicity of systemically administered cytokines is not surprising since these agents mediate local cellular interactions and they are normally secreted in limited quantities in a paracrine fashion.

Investigators are exploring other techniques to evaluate the use of reduced dose levels of IL-2. One protocol is an adoptive transfer approach that involves altering a patient's tumor cells by removing them from the patient, transfecting them with the IL-2 gene using a retroviral vector and then reinjecting them back into the patient. Another approach is to inject an established HLA-A2 positive immunizing cell line (allogeneic matched cells) that has been altered to secrete IL-2.

There is a need for the direct intralesional administration of recombinant genes into established tumors in vivo, to genetically modify them, as they grow in situ, to produce and secrete local amounts of IL-2.

There is also a need to overcome the limitations of an approach where tumor cells are collected, propagated in vitro, modified and selected and then reinjected in vivo.

SUMMARY OF THE INVENTION

According to the invention there is provided a plasmid suitable for IL-2 eukaryotic expression, consisting essentially of: an expression facilitating sequence derived from the immediate-early promoter region of CMV; an expression facilitating sequence derived from the transcriptional termination/polyadenylation signal sequence of the BGH gene; a sequence coding for the eukaryotic expression of an IL-2, characterized as possessing a bioactivity of the complete IL-2, operably linked to both of said expression facilitating sequences, wherein said sequence coding for the expression of an IL-2 is a sequence encoding a mature IL-2 and a non-IL-2 leader peptide that augments eukaryotic expression compared to a wild-type IL-2 leader peptide; and, optionally: a non-mammalian origin of replication; and a sequence operably encoding a selectable marker.

The mature IL-2 may be homologous to wild-type human IL-2.

The non-IL-2 leader peptide may constitute the human IL-2 leader peptide except for the addition of four amino acids.

The non-IL-2 leader peptide may constitute the human IL-2 leader peptide except for the replacement at the 5' end of Met-Ala-Leu-Trp-Ile-Asp SEQ ID No:3 for Met-Tyr.

The expression facilitating sequence derived from the immediate-early promoter region of CMV may be a promoter sequence and an intron sequence.

The expression facilitating sequence derived from the transcriptional termination/polyadenylation signal sequence of the BGH gene may be a transcriptional termination and a polyadenylation signal sequence.

The plasmid may possess the functional characteristics of the plasmid encoded by the nucleotide sequence of SEQ ID NO:1.

The plasmid may have the nucleotide sequence of SEQ ID NO:1.

The plasmid may be capable of directing production and secretion of human IL-2 in a human tumor cell.

In another embodiment the invention provides a host cell transformed any of the above plasmids.

In still another embodiment the invention provides a method for producing any of the above plasmids, comprising the steps of: growing bacterial cells containing the plasmid; and recovering the plasmid from the bacterial cells.

In yet another embodiment the invention provides a cassette system adapted for use in the direct intralesional administration of recombinant genes into established tumor cells in vivo, as they grow in situ, to produce and secrete IL-2, consisting essentially of: a transcription unit, encoding IL-2 in a replicon, containing a sequence encoding a non-IL-2 leader peptide constituting the human IL-2 leader peptide except for the replacement at the 5' end of Met-Ala-Leu-Trp-Ile-Asp SEQ ID No:3 for Met-Tyr, which sequence encoding said non-IL-2 leader peptide is operably linked to sequence encoding said IL-2.

In a further embodiment the invention provides a vector comprising a DNA sequence operably encoding a protein of interest and a non-IL-2 leader peptide, which non-IL-2 leader peptide constitutes the human IL-2 leader peptide except for the replacement at the 5' end of Met-Ala-Leu-Trp-Ile-Asp SEQ ID No:3 for Met-Tyr, wherein the non-IL-2 leader peptide is capable of augmenting the secretion of the protein in a mammalian cell.

In an additional embodiment the invention provides a pharmaceutical composition comprising the plasmid of Claim 1 in combination with a pharmaceutically acceptable vehicle. The plasmid may complexed to a cationic lipid mixture. The cationic lipid mixture may be DMRIE-DOPE. The DMRIE-DOPE may have a molar ratio of about 1:1. The plasmid to lipid ratio may be about 5:1.

The invention also provides a eukaryotic expression vector for the expression of a DNA sequence in a human tissue, consisting essentially of: a CMV immediate early sequence that contains a CMV promoter and a CMV intron; a sequence whose 5' end is attached to the 3' end of the CMV sequence, the sequence encoding a non-IL-2 leader peptide, the peptide constituting the human IL-2 leader peptide except for the replacement at the 5' end of Met-Ala-Leu-Trp-Ile-Asp SEQ ID No:3 for Met-Tyr; a cassette whose 5' end is attached to the 3' end of the sequence encoding a non-IL-2 leader peptide, the cassette containing a DNA sequence that is to be expressed; and-a BGH gene sequence whose 5' end is attached the 3' end of the cassette, the BGH sequence containing a transcriptional termination and a polyadenylation signal; and a selectable marker; wherein the vector is capable of replicating in prokaryotes.

In another embodiment the invention provides a method of gene therapy, the improvement comprising administering any of the above plasmids directly into a solid tumor resulting in the local secretion of IL-2.

BRIEF DESCRIPTION OF THE DRAWINGS

FIG. 21. IL-2 Bioassay. The lipid used for the in vitro transfection is indicated in parenthesis following the sample number. Samples: #5–#6, CMVBGH (parental plasmid without the human IL-2 gene); #19–#24, IL-2 plasmid DNA; #21+Ab, IL-2 plasmid DNA+neutralizing anti-IL-2 antibody; hr IL-2, recombinant human IL-2.

DETAILED DESCRIPTION OF THE INVENTION

Figure 1:
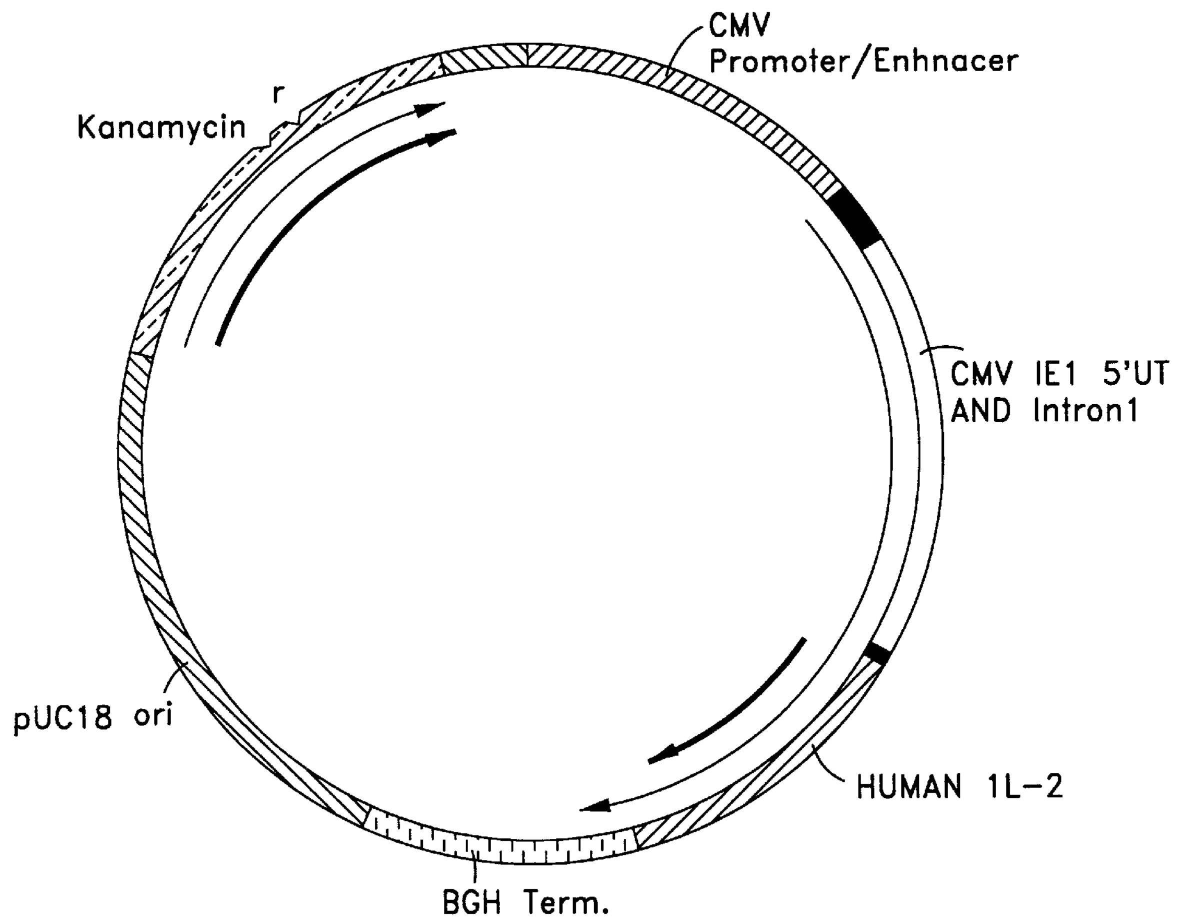
FIG. 1. IL-2 Plasmid DNA Construct.

It will be readily apparent to one skilled in the art that various substitutions and modifications may be made to the invention disclosed herein without departing from the scope and spirit of the invention.

A novel immunotherapeutic agent has been developed for intervention in human malignancy. A plasmid suitable for IL-2 expression has been developed for use as an immunotherapeutic agent in the treatment of patients with solid tumors or lymphomas. This approach relies on the direct intralesional administration of recombinant genes into established tumor cells in vivo, to genetically modify them, as they grow in situ, to produce and secrete local amounts of Interleukin-2 (IL-2).

This approach differs from previous methods in which tumor cells are collected, propagated in vitro, modified and selected and then reinjected in vivo. Limitations of these latter approaches include, 1) the need to establish a cell line from each experimental subject and to avoid tissue rejection, 2) concerns about alteration of the phenotype of cells propagated in tissue culture, 3) outgrowth of aberrant transformed cells, and 4) the time and effort required.

It is envisioned that the intralesional secretion of local amounts of IL-2 by tumor cells reduces or eliminates a systemic toxic response, recruits immune cells to the tumor site, causes immunologic recognition of specific tumor antigens, and causes subsequent tumor reduction or eradication.

In the present method, genes are directly transferred into solid tumor sites where local cells take up and express the gene. In some sites such as skeletal and cardiac muscle, expressible DNA can be injected without using carriers. In other tissues, such as tumor cells, DNA expression is facilitated by introducing the DNA complexed with a cationic lipid. The lipid component facilitates the entry of the DNA into those cells provided access to the DNA/lipid complex. Delivery of DNA to patients in a drug-like manner is thus facilitated.

In a proposed trial, this approach is applied to human patients with solid malignant tumors or lymphomas using a plasmid suitable for the expression of IL-2. This plasmid is introduced into solid tumor nodules. Tumor types include all solid cutaneous tumors, and metastases of malignant melanoma, renal cell carcinoma, and hepatic metastases of advanced colorectal carcinoma, as well as lymphomas.

In this study, the IL-2 plasmid is injected into solid malignant tumors or lymphomas of selected patients. Expression of IL-2 gene is confirmed. Gene dose responses are correlated with specific immune responses. In subsequent phases, this procedure is envisioned as part of protocols to be augmented by other antitumor therapy. Such studies provide an alternative strategy for the immunotherapy of malignancy and allow definition of the mechanisms of immune rejection of tumor cells. Adaptations of this method are also applied to the treatment of other human diseases.

Protocol Information

A Phase I study is described to test for safety and dose optimization of the direct gene transfer approach for delivering the IL-2 gene directly into solid tumors and lymphomas.

According to the Phase I protocol, the product is composed of a plasmid DNA coding for IL-2, formulated with a cationic lipid mixture. The cationic lipid mixture is prepared from a mixture of lipids, preferably of positively charged lipids and neutral lipids, e.g., DMRIE and DOPE. When introduced into the target tumor tissues, the lipid facilitates transfection of the plasmid. On introduction of the plasmid, the recombinant gene is expressed.

The Phase I study is directed to determining safety and dose optimization of the direct gene transfer approach using a plasmid suitable for IL-2 expression. The preferred plasmid is a circular, double-stranded DNA plasmid that is a simplified eukaryotic expression vector. The gene for IL-2 is inserted into that plasmid so that IL-2 is expressed when the plasmid is introduced into cells. Other genes are also included to aid and enhance expression of IL-2. Accordingly, IL-2 is placed under the transcriptional control of the cytomegalovirus (CMV) immediate early promoter/enhancer sequence that facilitates expression of a composite mRNA containing a 5' untranslated (UT) sequence from the CMV, the IL-2 coding sequence, and the bovine growth hormone 3' UT sequence. The plasmid also includes a bacterially expressed kanamycin resistance (kanamycinr) gene, derived from transposable element TN903, and a bacterial origin of replication. It does not contain any eukaryotic origins of replication (precluding integration into host genomic DNA) or any other viral sequences (precluding infection) or known oncogenic coding sequences (precluding oncogenesis). A figure of this plasmid is provided in FIG. 1.

The preferred DMRIE/DOPE lipid mixture includes two lipid components.

Figure 2A:
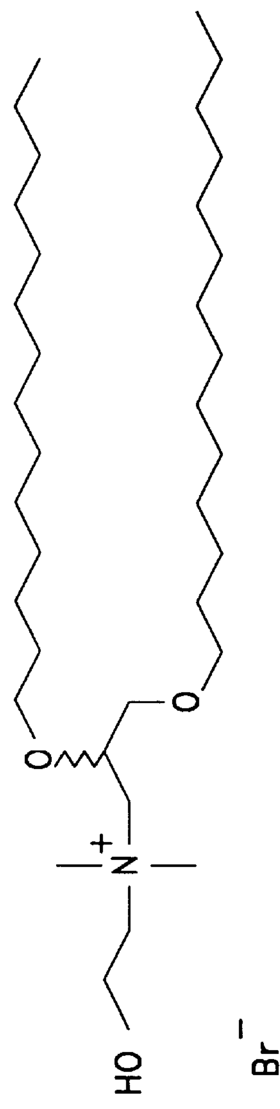
FIG. 2. Structures of DMRIE-Br and DOPE. A. DMRIE, synthesized as DMRIE-Br (CAS name: (+/−)-N-(2-hydroxyethyl)-N,N-dimethyl-2,3-bis (tetradecyloxy)-1-propanaminium bromide) is a cationic lipid with a molecular weight of 636.89. The structur of DMRIE-Br is given. B.DOPE (CAS name: 1,2-dioleoyl-sn-glycero-3-phosphoethanolamine) is a cationic lipid with a molecular weight of 744.04. The structure of DOPE is given.

DMRIE, synthesized as DMRIE-Br (CAS name: (+/−)-N-(2-hydroxyethyl) -N,N-dimethyl-2,3-bis (tetradecyloxy) -1-propanaminium bromide) is a cationic lipid with a molecular weight of 636.89. The structure of DMRIE-Br is given in FIG. 2A.

Figure 2B:
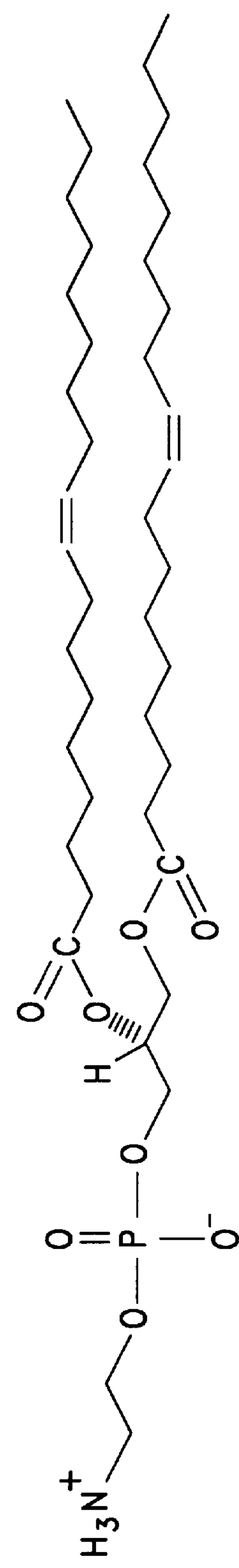

DOPE (CAS name: 1,2-dioleoyl-sn-glycero-3-phosphoethanolamine) is a neutral lipid with a molecular weight of 744.04. Thus structure of DOPE is given in FIG. 2B.

The Phase I clinical trial calls for a dose package that contains escalating doses of the plasmid DNA formulated with the DMRIE/DOPE lipid mixture in an injection vehicle. The proposed concentrations of plasmid DNA and DMRIE/DOPE in each dose package is specified in the following table:

TABLE OF DOSE PACKAGES

| Dose Package | Plasmid DNA conc. (mg/mL) | Mass dried DMRIE/DOPE (mg/mL) | Volume sterile injection vehicle (mL) |
|---|---|---|---|
| 10 μg | 0.01 | 0.004 | 1.2 |
| 30 μg | 0.03 | 0.012 | 1.2 |
| 100 μg | 0.10 | 0.04 | 1.2 |
| 300 μg | 0.30 | 0.12 | 1.2 |

The Phase I trial tests the IL-2 DNA/DMRIE/DOPE lipid complex as an immunotherapeutic agent in solid malignant tumors or lymphomas by direct gene transfer.

The objectives of this Phase I study include: 1) to determine in patients with metastatic malignancies the safety, side effects, toxicity and maximum tolerated dose (MTD) of direct intratumoral injection of increasing doses of a DNA/lipid mixture designed to introduce the IL-2 gene into patients with solid tumors or metastases or lymphomas, 2) to confirm in vivo expression of the IL-2 gene in the tumor cells, 3) to determine the biological activity and pharmacokinetics of the treatment including: intratumoral gene transfection and transcription by PCR analysis, intratumoral inflammatory or immune response by immunohistochemistry of tumor biopsies, and systemic immune activation as measured by baseline peripheral blood mononuclear cell (PBMC) thymidine incorporation, NK cell activity and CTL activity against autologous tumor cells, and 4) to characterize the clinical response to the study drug by serially assessing the size of the injected tumor and of other tumor masses that may be present and evaluable.

This is a Phase I open-label study in which up to 25 patients are enrolled for injections directly into tumor nodules with a lipid-formulated IL-2 plasmid complex. Solid tumors (excluding bony tumors), and metastases of malignant melanoma, renal cell carcinoma, and hepatic metastases of advanced colorectal carcinoma, and lymphomas are the tumor types to be evaluated.

Eligible patients have a primary tumor nodule injected several times at specified intervals with a specified dose of the study drug (see below). There are four groups with 5 patients each treated at the prescribed dose (10, 30, 100 or 300 μg), with a group of 5 patients retreated at the MTD dose, or at 300 μg if the MTD is not reached. The highest dose that does not yield Grade 3 or higher toxicities is considered the MTD. All toxicities are graded according to the World Health Organization (WHO) Recommendations for Grading of Acute and Sub-Acute Toxic Effects. (All patents and publications cited hereunder are incorporated herein by reference.)

TABLE OF SPECIFIED DOSES

| Dosage Group | No. Of Patients Per Group | Dose Per Treatment | Total No. Of Treatments Per Patient | Days Between Treatments |
|---|---|---|---|---|
| I | 5 | 10 ug | 6 | 7 |
| II | 5 | 30 ug | 6 | 7 |
| III | 5 | 100 ug | 6 | 7 |

-continued

TABLE OF SPECIFIED DOSES

| Dosage Group | No. Of Patients Per Group | Dose Per Treatment | Total No. Of Treatments Per Patient | Days Between Treatments |
|---|---|---|---|---|
| IV | 5 | 300 ug | 6 | 7 |
| V | 5 | MTD | 6 | 7 |

Patients are carefully selected based on their past medical history and present status, if they have failed conventional therapy or if conventional therapy is not indicated, and if they meet the following inclusion criteria: 1) histologically confirmed metastasis of malignant disease, 2) patients must have at least one metastatic lesion measurable in two dimensions and at least 1 cm in longest diameter, 3) patients must have had either prior standard therapies for their disease and have become unresponsive to them, or have made the decision that other therapy would not be of any major benefit, 4) patients must be adults, 18 years of age or older, 5) patients must have adequate bone marrow reserve: WBC>3000/mm$^3$, platelets>100,000/mm$^3$, hemoglobin>9.0 gm %, adequate renal and liver function: creatinine≦2.0, bilirubin <2.0 mg/DL, SGOT and SGPT <3×the upper limit of normal, adequate coagulation: PT and PTT within normal limits, 6) patients must have a baseline Karnofsky Performance Status (KPS) score of a least 70, 7) estimated life expectancy of a least 16 weeks, 8) patients must be able to render signed informed consent, 9) patients must be HIV antibody negative, Hepatitis B antigen negative and IL-2 antibody negative, 10) female patients who have child bearing potential must use an approved method of contraception and test negative for pregnancy (both male and female patients must use contraception during the course of the study), and 11) patients must demonstrate immunocompetence by having a PHA stimulated lymphocyte response in the normal range.

Those are excluded who meet the following exclusion criteria: 1) patients who are Hepatitis B antigen positive, HIV antibody positive or IL-2 antibody positive, 2) patients with a history of autoimmune disease, 3) patients with a history of hepatitis (acute or chronic active), 4) patients with any active infection requiring parenteral antibiotics, 5) patients with uncontrolled hypertension or New York Heart Association stage 3 or 4 disease, 6) patients receiving radiation, chemotherapy, steroid therapy within the past 3 weeks or 6 weeks if they have received BCNU or Mitomycin C, 7) patients receiving concurrent anticancer drug therapy, any immunosuppressive drugs and any other experimental therapy, 8) patients who fail to meet the criteria for immunocompetence as defined above, 9) patients with diabetes mellitus who are not controlled by medical treatment, 10) patients with uncontrolled brain metastases, and 11) patients with pre-diagnosed psychiatric disorders that would make compliance to the protocol difficult, or would compromise ability to give informed consent.

The study drug is supplied as a single sterile vial containing Interleukin-2 plasmid DNA and DMRIE/DOPE lipid mixture in an injection vehicle.

The DNA concentration is specified in the following table:

TABLE OF DNA CONCENTRATIONS

| Dose to Patient | Plasmid DNA Concentration (mg/Ml) |
|---|---|
| 10 ug | 0.01 |
| 30 ug | 0.03 |
| 100 ug | 0.1 |
| 300 ug | 0.3 |

The study drug is administered and toxicities are monitored. Tumor lesions are selected for treatment if they are accessible to intratumor administration by direct needle injection. These metastatic lesions are located at any accessible site such as skin, nodes, lung, liver, soft tissues etc. Bony tumors are excluded. The amount of study drug material injected into each tumor is based on the algorithm outline below. The prescribed dose (10, 30, 100 or 300 $\mu$g) is thawed and diluted with injection vehicle to the appropriate volume. If necessary, the study drug is injected with the aid of sonographic or CAT scan visualization of the metastasis. Prior to injection, following placement of the needle, gentle aspiration is applied to the syringe to ensure that no material is injection intravenously. After injection of the drug and with the needle still in place, the dead space is flushed with 0.25–0.50 mL of injection vehicle.

| Tumor Diameter (cm) | Volume of Injection (cc) |
|---|---|
| 1.0–1.5 | 1.0 |
| 1.6–2.0 | 2.0 |
| 2.1–3.0 | 3.0 |
| 3.1–X | 4.0 |

Vital signs are measured every 15 minutes at the start of, during, and after the injection for at least 2 hours or until the patient is stable. If the systolic blood pressure drops below 80 mm Hg, the injection is terminated immediately and the patient is closely monitored and treated appropriately until blood pressure is normalized.

Patients are closely monitored for toxicity for 3–4 hours post injection then 24 hours and 7 days after the first and second injections. For injections 3–6, patients are monitored for 3–4 hours post injection then 7 days post injection as long as they have experienced no toxicity during the 4 and 24 hour observation periods following injections 1 and 2.

TABLE OF SCHEDULE FOR POST-INJECTION MONITORING

| Treatment # | 3–4 Hrs | 24 Hrs | 7 Days | 14 Days |
|---|---|---|---|---|
| 1 | X | X | X | — |
| 2 | X | X | X | — |
| 3 | X | — | X | — |
| 4 | X | — | X | — |
| 5 | X | — | X | — |
| 6 | X | — | X | X |

Before each subsequent injection, patients are evaluated for toxicities from the prior injection and injected with the next dose only if no Grade 3 or higher toxicity occurs. A tumor sizing is done at each intramural injection of the nodule. If the tumor shrinks to a point where it can no longer be injected, subsequent doses are administered into another tumor nodule if any are present.

After the 6th injection, patient follow-up includes evaluations with tumor sizings at weeks 8 and 16. After the week 16 visit, patients are evaluated a minimum of every 4 months.

If a patient experiences stable disease or a partial response (see below) at 4–8 weeks after the last injection of their initial course, he/she may receive an additional course of treatment identical to the first course of treatment or the next higher dose. The patient must, however, continue to meet the entry criteria.

No more than two weeks prior to entry into the study, and several times during the study according to a schedule of events, all patients have the following studies performed to assess their disease status: 1) physical exam and medical history, including height, weight, vital signs, performance status, and tumor measurements (tumor staging by physical exam when accessible), 2) chest X ray, 3) EKG, 4) CBC, platelet count, differential, PT, PTT, 5) blood chemistries: creatinine, BUN, bilirubin, alkaline phosphatase, LDH, SGOT, SGPT, phosphorus, uric acid, calcium, total protein, albumin, glucose, 6) Lymphocyte Proliferative Response to PHA, 7) anergy panel skin tests, 8) pregnancy test for women, 9) HIV antibody test, 10) hepatitis screen, 11) IL-2 antibody test, 12) tumor biopsies, 13) CT/MRI/Ultrasound (if relevant) for baseline and to evaluate status of disease, 14) special tests: blood is drawn for serum to be analyzed by PCR for the presence of the plasmid, 15) blood draws during this is limited to a maximum of 60 mL each time.

Adverse events are monitored, and patients are removed from the study if unacceptable toxicity (Grade III or IV) develops.

Classical pharmacological studies of drug distribution, half time, metabolism, and excretion are not entirely relevant to in vivo gene injection and expression. However, the fate of the plasmid and detection of the gene product (IL-2) are relevant to the development of this agent. In addition, immune activation is important. Therefore, as part of the measurement of the efficacy of this study, successful gene transfer and expression is evaluated by molecular and immunological analyses. The following parameters are measured to evaluate the tumor transfection and expression of IL-2: 1) the presence of DNA from the IL-2 gene is assessed by PCR amplification of cells obtained by biopsy of the treated site after the injection of the study drug, 2) immunohistochemical staining of tumor biopsy samples is used to assess immunologic response and soluble IL-2 expression, 3) serum IL-2 level are measured pre-treatment and 2 times post the start of therapy, however, the detection of serum IL-2 levels is not anticipated, 4) PCR analysis of peripheral blood samples is used to test for the presence of plasmid DNA after the start of treatment and compared to pre-therapy, but detection of the gene in peripheral blood samples is not anticipated, 5) the cellular immune response is evaluated by measuring baseline and post-treatment IL-2 induced activation of PBMC by thymidine uptake assay and NK/LAK response in peripheral blood pre-therapy and post-therapy, and 6) an attempt is made to excise tumor tissue from another site prior to treatment for diagnosis, immunochemistry, cryo-preservation and to evaluate peripheral blood lymphocyte immunological reactions to the tumor before and after treatment.

As an additional part of the evaluation of the efficacy of this study, the clinical response is measured. Standard oncologic criteria are applied to determine whether or not a patient responds to the study drug. All tumor measurements are recorded in centimeters and constitute the longest diameter and the perpendicular diameter at the widest portion of the tumor. The tumor response definitions listed below are used to compare current total tumor size to pre-treatment total tumor size.

There is a complete tumor response upon disappearance of all clinical evidence of active tumor for a minimum of four weeks, and the patients is free of all symptoms of cancer.

There is a partial tumor response upon fifty percent (50%) or greater decrease in the sum of the products of all diameters of measurable lesions. These reductions in tumor size must endure for a minimum of four weeks. No simultaneous increase in the size of any lesion or appearance of new lesions may occur. The appropriate diagnostic tests used to demonstrate the response must be repeated four weeks after initial observation in order to document this duration.

There is stable disease upon less than 50% decrease in the sum of the products of all diameters of measurable lesions, or an increase in the tumor mass less than 25% in the absence of the development of new lesions.

There is progressive disease upon tumor progression as defined if one or more of the following criteria are met: 1) appearance of any new lesions(s), 2) increase in tumor size of ≧25% in the sum of the products of all diameters of measurable lesions, 3) significant clinical deterioration that cannot be attributed to treatment or other medical conditions and is assumed to be related to increased tumor burden, and 4) worsening of tumor-related symptoms deemed clinically significant by physician.

The principles of informed consent described in Food and Drug Administration (FDA) Regulations 21 C.F.R. Part 50 are followed.

Approval is obtained by the study site Institutional Review Board (IRB) for the Clinical Protocol and Informed Consent Document, and agreement is obtained from the IRB to monitor the conduct of the study and review it periodically.

The primary goal of this protocol is to determine the safety, side effects, toxicity, and maximum tolerated dose (MTD) of direct intratumoral injection of increasing doses of the IL-2 plasmid in patients with solid tumors or metastases or lymphomas. Five groups with five patients each is evaluated at potentially four dose levels. The MTD is defined as the highest dose which does not result in Grade 3 or higher toxicity in any of the patients treated at that dose (it is recognized that the MTD may not be reached). Toxicities and side effects at each dose level are tabulated.

This design is based on the traditional design for early phase I studies. Although newer approaches have preferred properties from a statistical perspective, the application of these approaches to this study is limited because they typically require a much larger number of potential doses (Storer BE. Biometrics 45:925–937, 1989) or prior information about the dose-toxicity relationship (O'Quigley J, Chevret S. Statistics in Medicine 10:1647–1664, 1991; O'Quigley J, Pepe M, Fisher L. Biometrics 46:33–48, 1990.). The traditional design is therefore preferably chosen to be retained.

Chemistry, Manufacturing and Controls

The plasmid suitable for IL-2 expression is a eukaryotic expression vector that codes for the production of the human IL-2 protein. A process for the production of this plasmid has been developed using *E. coli.* The process is scaleable and is a combination of highly reproducible unit operations (fermentation, cell lysis, precipitation, size exclusion chromatography, formulation and fill). The advantages over existing methods include scaleability, improved plasmid purity and the elimination of undesirable process additives such as toxic solvents and animal derived enzymes.

The plasmid DNA is complexed with a cationic lipid preferably of DMRIE/DOPE to protect the DNA from degradation and facilitate cell entry.

The plasmid DNA is identified as the drug substance. The plasmid DNA is produced by bacterial fermentation in a well-characterized *E. coli* host. When introduced into eukaryotic cells, the recombinant genes in the plasmid are expressed, producing a biologically active gene expression product, Interleukin-2.

To form the drug product, the plasmid DNA is mixed with a combination of the lipids DMRIE and DOPE in injection vehicle. The DMRIE/DOPE lipid combination bears a net positive charge and can bind with the negatively charged DNA molecules. The resulting mixture of plasmid DNA and lipids is injected directly into solid tumor.

The plasmid DNA/lipid complex drug product is packaged and released in a liquid injectable dosage from a single dose vial.

The plasmid DNA is identified as the drug substance. The drug product is the final formulation of the plasmid complexed with the lipid mixture component in injection vehicle, in a vialed injectable dosage form.

Characteristics

One skilled in the art will readily appreciate that the IL-2 plasmid described herein is representative of a preferred embodiment that is exemplary and not intended as a limitation on the scope of the invention.

Any eukaryotic expression vector that is adapted to carry out the objects and obtain the ends and advantages mentioned as well as those inherent herein is encompassed within the spirit of the invention.

Accordingly, the IL-2 plasmid is assembled out of components where different selectable genes, origins, promoters, introns, 5' untranslated (UT) sequence, terminators, polyadenylation signals, 3' UT sequence, and leader peptides, etc. are put together to make the vector of your choice. This vector system is considered not so much a complete vector as a cassette system. Thus, selectable genes, origins, promoters, introns, 5' UT sequence, terminators, polyadenylation signals, 3' UT sequence and leader peptides, etc. can be substituted for those described.

Moreover, the IL-2 gene can be removed and another gene of interest substituted, should one desire to use the eukaryotic expression vector for the production of another protein.

Depending on how the plasmid is to be synthesized, it is adaptable to being replicated in bacterial cells, such as *E. coli,* or eukaryotic cells, such as yeast cells, insect cells, and mammalian cells, and, consequently, contains an appropriate origin of replication.

Additionally, it may contain selectable genes, by which host cells that have been transformed/transfected can be selected, such as genes that code for resistance to antibiotics.

Optionally, it may contain backbone derived from vectors such as pUC based plasmids and pBR322 and its derivatives, depending on how it is constructed.

Alternatively, it may be chemically synthesized and not contain an origin of replication or even be considered a replicon.

Promoters and similar elements, such as enhancers, and introns, and 5' UT sequence that promote eukaryotic expression are contemplated.

Terminators, polyadenylations signals, and 3' UT sequence that facilitate eukaryotic expression are envisioned.

Leader peptides and fusion leaders are contemplated. For example, the IL-2 leader peptide can be used or replaced by another leader peptide or a fusion leader.

Sequences of the IL-2 gene are envisioned, for example, to account for allelic differences and species variations. Conservative variants and functional fragments are contemplated. These are meant to include molecules that possess a bioactivity of the complete IL-2.

While a simplified expression vector is preferred, others are envisaged. Thus, the vector can be made bi-cistronic or poly-cistronic. Other genes of interest encoding, for example, other therapeutically important molecules, can be inserted. Other elements that facilitate eukaryotic expression may be added to the vector, for example, the EMC CITE sequence of U.S. Pat. No. 4,937,190 that functions as a translation enhancer.

In a preferred embodiment, the IL-2 plasmid is 4928 bp in size with a base composition of 2500 adenines, 2428 cytosines, 2428 guanines, and 2500 thymidines. The molecular weight is $3.38018 \times 10^6$ g.m.u. The IL-2 plasmid is diagrammed in FIG. 1, and the nucleotide sequence of the coding strand of the plasmid is given as SEQ ID NO:1. This is a high copy number plasmid that was constructed using isolated segments of cloned DNA, of known sequence, which were shuttled from one plasmid to another using standard molecular genetic techniques and commercially available enzymes.

The backbone plasmid DNA is derived from pUC18, a commercially available DNA widely used in molecular biology laboratories.

The plasmid contains the human IL-2 gene, and expresses IL-2 which has been shown to be biologically active in preclinical studies to date.

The plasmid contains two significant open reading frames, the kanamycin resistance protein, expressed in bacterial cells, and rat insulin II leader peptide/IL-2 fusion protein, expressed in mammalian cells. There are no additional viral or oncogenic sequences within the plasmid DNA.

The manufactured drug substance, the plasmid DNA, is a covalently closed circular DNA macromolecule biosynthesized in bacterial cells which have been grown in a kanamycin selection media. Bacterial cell growth is thus dependent upon the expression of the kanamycin resistance protein encoded within the plasmid DNA. Following preparation of culture of bacterial cells harboring this plasmid, the plasmid is purified from all other cellular products. The plasmid DNA is therefore an acellular product.

In addition to the kanamycin resistance gene, the plasmid DNA contains a nearly complete human IL-2 cDNA linked to a short DNA segment from the rat insulin II gene. The resulting sequence is predicted to encode a fusion protein constituting the first six amino acids from the rat insulin II leader peptide and amino acids 3 to 153 (complete carboxyl terminus) of IL-2. Eukaryotic cell transcription of this fusion protein coding sequence is controlled by the cytomegalovirus (CMV) immediate early 1 promoter which initiates mRNA synthesis at the endogenous immediate early 1 gene transcriptional initiation site, expressing a primary RNA transcript comprising the immediate early gene 5' untranslated (UT) region and intron. The intron is subsequently cleaved out of the mRNA molecule. Contiguous to the 3' end of the IL-2 coding sequence is a bovine growth hormone (BGH) gene sequence containing the coding region for the BGH 3' UT region along with the signal sequence for polyadenylation and transcriptional termination.

Therefore the IL-2 mRNA molecule, transcribed by the eukaryotic cell restricted CMV promoter, contains, in addition to CMV 5' UT and human IL-2 coding sequence, a large portion of the BGH 3' UT sequence and a polyadenylation tail. Finally, replication of the plasmid DNA in bacterial cells is regulated by the presence of a bacterial origin of replication.

Individual preparations of purified DNA are characterized for concentration by optical density absorbance measurements using a spectrophotometer with a 260 nanometer light source (1 absorbance unit=50 $\mu$g of DNA). Plasmid size and percentage of covalently closed DNA product is determined by electrophoretic migration, relative to known standards, on agarose gels.

Additional characterization is made using selective restriction endonuclease digestion of the drug DNA with subsequent separation and sizing of the predicted DNA fragments by agarose gel electrophoresis. Manifestation of expression of the coding sequences is determined by logarithmic growth of plasmid transformed bacterial cells in selection media (kanamycin resistance expression) and by ELISA assay of cultured mammalian cell spent media samples following plasmid transfection of those cells growing in vitro.

Combination of the cationic lipid DMRIE with DOPE, a charge-neutral lipid, gives the DMRIE/DOPE lipid mixture used in the plasmid DNA/lipid complex drug product. The plasmid DNA is mixed with the DMRIE/DOPE lipid combination at a mass ratio of from about 9:1 to 1:9, preferably 5:1 (plasmid DNA:cationic lipid), to form the plasmid DNA/lipid complex drug product. The preferable plasmid DNA:DMRIE mass ratio of 5:1 is chosen by concurrent optimization of aqueous solubility at the projected highest clinical dose concentration of 0.3 mg plasmid DNA/mL and in vitro transfection efficiency.

DMRIE and DOPE are both pure chemical synthetics and are not derived from any natural source which may leave antigen-producing substances as residues. Thus, there is little potential for contamination of DMRIE and DOPE by antigen-producing substances.

Preparation

The IL-2 plasmid DNA was constructed using isolated segments of cloned DNA, of known sequence, which were shuttled from one plasmid to another using standard molecular genetic techniques and commercially available enzymes (i.e., *E. coli* DNA polymerase I (Klenow fragment), bacteriophage T7 polymerase, bacteriophage T4 ligase, etc.). Subcloned products were tested for orientation and for sequence integrity by DNA restriction endonucleases digest mapping. The individual segments functioned to effect a high level of replication of plasmid DNA in bacterial cells, conferred expression of a selectable marker protein to bacterial cells harboring the plasmid, and, when introduced into mammalian cells, effected a high level of IL-2 expression. All subsequent references to domains of the IL-2 DNA will be oriented using the designation of first nucleotide at the 5' end of the CMV promoter as being nucleotide #1 (see FIG. 1 and SEQ ID NO:1).

The origin of replication of the plasmid DNA pUC18 backbone was taken from the naturally occurring bacterial plasmid, ColiE1 (Bolivar, R. et al.[1977] Gene 2, 95–113). pUC18 sequences are found in two locations within the plasmid The first, comprising the 5' end of the bacterial lac operon and the ColiE1 origin of replication is located between base $A^{2798}$ and $G^{3871}$ and corresponds to the EcoRI to BspHI fragment of pUC18.

The second pUC18 segment is located between $A^{4740}$ and $T^{4911}$ and corresponds to the NarI/HindIII restriction endonuclease sites of pUC18.

These two fragments are separated on the IL-2 plasmid by the insertion of the DNA encoding the kanamycin resistance gene derived from the bacterial transposon TN903 (Oka, A. et al. [1981] J. Mol. Biol. 147, 217–226). This resulted from the removal of a fragment containing the β-Lactamase gene (ampicillin resistance) normally found on pUC18 using NarI (Klenow fill-in) and AlwNI restriction endonuclease digestions and inserting an EcoRI (Klenow fill-in) and AlwNI restriction fragment from pET-9a (Novagen, Inc., Madison, Wis.) containing the TN903 gene into the IL-2 plasmid at $T^{3872}$ to $G^{4739}$.

Consequently, the IL-2 plasmid is designed to express the 30,700 MW aminoglycoside 3'-phosphotransferase protein (Berg, D. et al. [1978] In Microbiology-1978 [Schlessinger, D. ed.] pp 13–15, American Society for Microbiology, Washington, D.C.) in bacterial cells using the kanamycin gene promoter. The protein is encoded on the same strand of DNA as that encoding IL-2. The open reading frame for kanamycin resistance is from $A^{3923}$ to $T^{4736}$.

Mammalian cell expression of the human IL-2 protein coding sequence is under the transcriptional control of the cytomegalovirus (CMV) immediate early 1 (IE1) promoter and the 5' untranslated region of the immediate early gene. This control sequence is positioned 5' to the IL-2 coding sequence on the IL-2 plasmid, representing bases 1 to 1619 (SspI/SalI) of the plasmid. It was originally obtained from a pRL103a plasmid clone (LaFemina, R. and Hayward, G. [1980] In Fields and Jaenish (ed.), Animal Virus Genetics, Academic Press, New York, Vol. 18, pp. 30–55.) prepared from a 21 Kb HindIII fragment derived from human CMV (Towne strain) genome.

DNA from the 21 Kb clone was used to construct a pCMV6 expression plasmid (Chapman, B. et al. [1991] Nucl. Acids Res. 19, 3979–3986) using a SspI at −671 (bases from the CMV IE1 gene transcriptional initiation site) and PstI at +944 bp fragment. The SspI/SalI sequence was derived from pCMV6 which inserted a synthetic linker fragment containing the SalI site within the 5' UT region, 3' to the viral PstI site. This viral transcriptional control element contains 671 bp of the untranscribed IE1 promoter and 948 bp of the transcribed IE1 5' UT region at plasmid bases 1–1619. The 948 bp segment contains an 833 bp IE1 gene intron, found only in the primary mRNA transcribed from the IE1 promoter.

The coding sequence for IL-2 was isolated from a pBC12/HIV/IL2 clone obtained from ATCC (#67618). Restriction endonuclease digest of pBC12/HIV/IL2 with NheI (Klenow fill-in), which cleaves 41 bp 5' to the translational initiation codon, and BamHI, which cleaves 34 bp 3' to the translational stop codon, excised the IL-2 coding sequence and enabled an oriented insertion into the IL-2 plasmid ($G^{1645}$ to $G^{2195}$). This sequence contains a 5' segment derived from the rat insulin II gene, coding for the 5' UT region and the six amino acids of the signal peptide of rat insulin ($G^{1645}$ to $C^{1706}$), and a 3' segment coding for human pro-IL-2 beginning with Arg3 of the signal peptide (Cullen, B. [1988] DNA 7, 645–650). The deduced pro-IL-2 thus has a signal peptide of four amino acids longer than human IL-2, while the mature IL-2 that is secreted is homologous to wild-type human IL-2.

$T^{1620}$ to $A^{1644}$, $G^{2196}$ to $A^{2249}$, and $T^{4912}$ to $C^{4928}$ represent portions of synthetic DNA linker sequences used to facilitate cloning.

The last segment of the IL-2 plasmid, $G^{2250}$ to $G^{2797}$, is a transcriptional terminator/polyadenylation signal sequence taken from the bovine growth hormone gene. This sequence was derived from a commercially available vector, pCMV3 (Invitrogen, Inc., San Diego, Calif.), and contains the bovine growth hormone gene 3' UT region, including the $A^{2346}$ ATAAA polyadenylation signal sequence, and more than 400 bases of gene sequence signaling transcriptional termination.

The IL-2 plasmid DNA was synthesized and transfected into a standard, commercially available *E. coli* host strain, DH10B. The DH10B genotype is:

F-mcrA A Δ (mrr-hsdRMS-mcrBC) Φ80dlacZΔM15 ΔlacX74 deoR recA1 endA1 araD139 Δ (ara, leu)7697 galU galK λ- rpsL nupG.

Characterization of the host cell was based on auxotrophy tests and antibiotic resistance test, and by documentation of the genotype by certificate from the commercial supplier, GIBCO/BRL/LTI, Bethesda, Md.

The IL-2 plasmid was introduced into the DH10B cells by standard transformation procedures. Transformed cells were selected (single clonal colony) on LB-agarose plates supplemented with 50 μg/mL kanamycin. These cells were the source for the Master Cell Bank (MCB) and Manufacturer's Working Cell Bank (MWCB) used in production of preclinical drug safety and clinical lots.

MCB host cells were prepared by diluting 1 μL of 1.28 mg/mL plasmid DNA 1:100 in TE buffer. Manufacturer's competent host cells were removed from −70° C. freezer and thawed on ice. Host cells were then mixed gently and aliquoted in 100 μL volumes into chilled 1.5 mL microcentrifuge tubes. 0.78 mL (i.e. 1 ng DNA) of diluted plasmid DNA was added, by gentle mixing, to 100 μl of competent host cells. Microcentrifuge tubes containing cells were incubated 30 minutes on ice (0–4° C.), then at 37° C. for 45 seconds to heat shock. Microcentrifuge tubes were then returned to ice (0–4° C.) for two minutes.

Luria Broth (LB) ( 900 μL) at ambient room temperature was added to each tube. Tubes were then shaken at 225 RPM, 37° C., in an INNOVA 4300 incubator for 60 minutes, followed by centrifugation at 12,000 g for 1 minute in a Sorvall microcentrifuge. 900 μl of supernate was removed and the cells were resuspended in the remaining~100 μl of broth.

On a plate of LB+agar+kanamycin, 25 μl of incubation volume containing cells transformed with plasmid were spread, then incubated overnight at 37° C. in a dry heat oven.

Cells grown on the LB+agar+50 mg/L kanamycin plate were observed. Characterization of these transformed cells included mini-prep analysis and restriction enzyme cuts.

The MCB was prepared by streaking transformed *E. coli* cells onto Luria broth (LB) agar plates which contained the antibiotic Kanamycin to select for plasmid-containing cells which are Kanamycin-resistant due to the construction of the plasmid. LB agar was prepared by adding 4.0-gm LB agar powder to a 500-mL flask containing 100-mL distilled water and mixed thoroughly until the LB agar powder was dispersed. The flask was plugged and the plug covered with Sterigard paper. The flask was then autoclaved for 30 min. at not less than 121° C.

After autoclaving, the flask was allowed to cool to approximately 45° C., and 5-mg Kanamycin was added to the LB agar. Four pour-plates containing approximately 25-mL each of the LB agar were prepared and allowed to set. Plasmid-containing cells were streaked onto each plate in such manner as to ensure growth of isolated colonies.

The plates were then incubated for 20–30 hours at 37° C. The plates were either stored at 2–6° C. or were used immediately. Using sterile technique in a laminar flow hood, 3 colonies, each having grown out from a single cell, were individually scraped from the plate, using a sterile loop, and were inoculated into 50 mL of sterile Terrific Broth (TB) medium (complete, including Kanamycin) in a sterile 250-mL flask. Flasks were incubated at 37° C. in a shaker/incubator at 300–400 rpm for 10–20 hours.

Using sterile technique in a laminar flow hood, an amount of 1.50-mL±0.025-mL, was removed from each flask and placed in a microcentrifuge tube, and the flasks were refrigerated at 2–6° C. The samples were centrifuged for 2 minutes at approximately 12,000 rpm in a Sorvall microcentrifuge to obtain a cell pellet, and mini-prep plasmid DNA analysis was performed. Restriction digests were performed to verify plasmid identity, and the plasmid minipreps were prepared for agarose-gel electrophoresis. Agarose gels were run, and Polaroid photographs were taken and labeled. The highest-yielding overnight culture, as determined from the gel photograph, was used to make a stock solution.

To a culture tube containing 4-mL of sterile glycerol, 4-mL of the culture selected on the basis of the mini-prep analysis was added. This was gently agitated to ensure a homogeneous mix.

The culture-glycerol mixture was distributed in 0.1-mL aliquots into 40–80 sterile, labeled, cryogenic storage vials. The vials were labeled. The vials were stored in liquid nitrogen in appropriately labeled containers.

The MWCB was obtained from the MCB by taking 1 vial of MCB glycerol stock and streaking it out onto an LB agar plate containing Kanamycin antibiotic. Plates were incubated 20–30 hours at 37° C. In a laminar flow hood, a sterile loop was used to pick individual colonies. Each colony was inoculated into 1 each of 3 1-L flasks containing 250-mL of TB medium (complete) with Kanamycin antibiotic. The flasks were incubated at 37° C. and at 300–400 rpm in a shaker for 10–15 hours.

A 1.5-mL sample was withdrawn from each of the 3 flasks and was prepared for a mini-prep analysis. Based on the results of the mini-prep analysis, the highest-yielding flask was selected to use in preparing glycerol stocks of the MWCB.

In a laminar flow hood, 4 mL of the culture was removed from the flask and was added to a culture tube containing 4 mL of sterile glycerol. The tube was gently agitated to ensure a homogeneous mix. The culture/glycerol mix was distributed in 0.1-mL aliquots into 30–60 sterile, labeled, cryogenic storage vials. The individual vials were labeled. The vials were stored at −70° C. to −80° C.

The fermentation process was performed as a 15-L batch fermentation in TB medium (tryptone, yeast extract, phosphate buffer and glycerol, containing the antibiotic Kanamycin) in a 20-L Braun fermenter. The following table depicts the fermentation process. A detailed discussion follows thereafter.

TABLE

FERMENTATION PROCESS

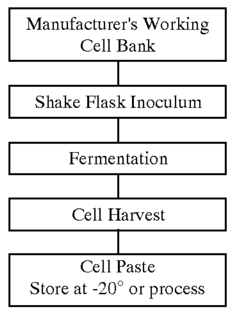

Inoculum preparation proceeded by streaking an LB/Kan agar plate with 0.1-mL of MWCB stock and incubating at 37° C. for 20–30 hours. TB medium was prepared by adding 24-gm yeast extract and 12-gm Trypticase peptone to a 2-L shake flask. Then, 900-mL distilled water was added to the flask and mixed thoroughly. When all contents were in solution, 4-mL glycerol was added and mixed thoroughly. This medium was distributed into three, 1 L flasks, 180 mL/flask. The flasks were plugged, and the plugs covered with Sterigard paper. The flasks were then autoclaved for 30 min. at not less than 121° C. When medium was cooled, 10-mg sterile Kanamycin and 20-mL sterile phosphate solution was added. The phosphate solution was prepared by dissolving 12.5 gm $K_2HPO_4$ and 2.3 gm $KH_2PO_4$ in 100-mL of deionized water in a 500-mL flask. The flask was plugged, and the plug covered with Sterigard paper. This flask was then autoclaved for 30 min. at not less than 121° C. With the addition of the Kanamycin and the phosphate solution, the TB medium was complete. The inoculated flask was shaken at 370° C. and 300–400 rpm for 10–20 hours in a shaker incubator cabinet.

Fermentation preparation ensued by cleaning a 20-L Braun Biostat ED fermenter with a solution of sodium hydroxide, followed by a phosphoric-acid wash, then thoroughly rinsing with deionized water. Deionized water in the amount of 6 L was added to the fermenter. Then, 360 gm yeast extract powder and 180-gm Trypticase peptone were added. An agitator was run to facilitate dissolving the powder. Next, 60-mL glycerol and 2-mL antifoam were added to the fermenter. The walls of the fermenter were rinsed with deionized water and the volume brought to approximately 14 L. The contents of the fermenter were sterilized by using batch control automatic cycle, on control unit, for at least 30 minutes at 121° C.

Fermentation conditions were monitored using the following control loops: pH, dissolved oxygen (DO), and temperature. Temperature was controlled to 300° C.,±0.50° C. Stirring speed was set for 600 rpm and the airflow control to 1 v/v/m,±0.1 v/v/m.

Fermentation inoculation proceeded after all control loops on the fermenter were verified to be on and operating correctly. A septum on the fermenter headplate was pierced with the sterilized manufacturer's inoculation fitting having three 3-ft to 4-ft, 3/32-ID silicone tubes attached. One sterile tube was used to introduce 1.5-L phosphate solution into the fermenter. The second sterile tube was used to introduce inoculum into fermenter. The third sterile tube was reserved for pH control, if necessary. All solutions were introduced into the fermenter using a peristaltic pump. Sterile Kanamycin solution, 50-mg/L, i.e., 750-mg/fermenter, was added to the phosphate solution.

Fermentation ensued with the above-listed parameters under automatic control. Samples of the fermentation broth were removed from the harvest valve at intervals, and the fermentation was complete when the OD600 was 20 or greater. Cells were harvested from the fermenter by drawing broth from the harvest valve into tared 1-L centrifuge bottles. Cells were concentrated by centrifugation at up to 4600 g for 30 minutes in a Jouan centrifuge. The supernatant was decanted, and the bottles were weighed to determine cell yield. From a harvest sample, a 1.5-mL aliquot was processed for mini-prep analysis, and restriction enzyme cuts were made to confirm the identity of the plasmid.

The purification process is depicted in the following table. A detailed discussion follows thereafter.

TABLE

PURIFICATION PROCESS

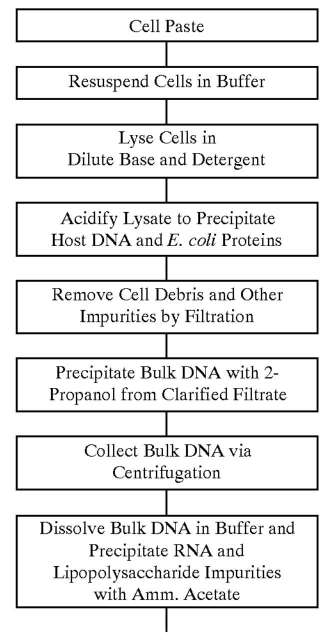

TABLE-continued

PURIFICATION PROCESS

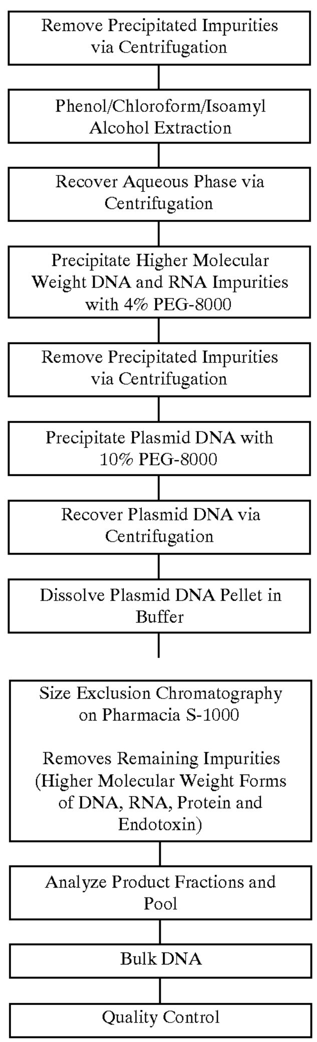

Cell Lysis: The cell paste was resuspended completely in 7 mLs per gram wet bacterial weight Solution I (61 mM Glucose+25 mM Tris buffer pH 8.0+10 mM EDTA pH 8.0 at 5° C.) with a magnetic stirrer at room temperature. To this solution 14 mLs per wet bacterial weight Solution II (0.2 N NaOH/1% SDS) was added and swirled until a viscous solution appeared. This was incubated on ice for 10 minutes without any additional swirling. To the lysed cell solution 10.5 mLs per wet bacterial weight of cold Solution III (3M potassium acetate pH 5.0 at 5° C.) was added, inverted, shaken vigorously, and incubated on ice for 10 minutes.

Filtration: The lysate was carefully filtered through two layers of synthetic cloth, e.g., MiraCloth® synthetic non-woven rayon fabric which has an average pore size of 22 to 25 $\mu$m (Calbiochem, Cat. #475855, La Jolla, Calif.), to remove large particulate debris. This was repeated 3 additional times through 16 layers MiraCloth® synthetic cloth each passage. Crude DNA filtrate was precipitated with 0.6 volumes cold isopropanol, adding about 200 mLs at a time and swirling, and incubated for 1 hour at room temperature. The crude nucleic acid precipitate was collected by centrifugation at 12000 rpm for 30 minutes at 5° C. After discarding the supernatant, the pellet was drained for 15 minutes and then was uprighted to air dry for 5 minutes. The DNA pellet was resuspended in TE buffer (0.01 M Tris-base+0.001 M EDTA pH 8.0) using approximately 1 mL TE per original wet weight bacteria. The filtration step aids in the removal of cell wall debris and chromosomal DNA. If this step were omitted chromosomal contamination would be carried over to final product.

RNA and Lipopolysaccharide Removal: After the pellet was resuspended in TE as described above, 0.29 grams per original wet weight bacteria of ammonium acetate was dissolved into the DNA/TE resuspension so that the final concentration was 2.5 M. Additional TE was added if necessary to correct the volume. This was incubated on ice for 15 minutes and then the process was continued or it was transferred to 4° C. overnight.

This was centrifuges at 10,000 rpm for 20 minutes, the pellet discarded and the supernatant was filtered through a 0.8$\mu$ membrane. An equal amount of phenol: chloroform: isoamyl alcohol (25:24:1) was added to the filtered supernatant. This was stirred using a magnetic stirrer for 30 minutes at room temperature. This was briefly centrifuged at 5000 rpm to facilitate the separation of the aqueous and organic phases. The upper, aqueous phase was collected and the DNA precipitated by the addition of 2 volumes −20° C. ethanol, mixed and incubated on ice for a minimum of 1 hour.

This was centrifuged at 12,000 rpm for 30 minutes. The supernatant was discarded and the remaining pellet was allowed to drain for 15 minutes and then uprighted to air dry for 5 minutes. The pellet was resuspended in TE buffer using 0.5 mLs per original wet weight bacteria.

Sodium acetate pH 5.2 was added to the resuspended pellet to a final concentration of 1.1M. 30% PEG-8000 in 1.6 M NaCl was added to this so that the final concentration was 4% PEG-8000 (w/v). This was allowed to incubate at 4° C. for a minimum of 8 hours.

The ammonium acetate step aids in the removal of some RNA and much of the lipopolysaccharides. The 4% PEG-8000 precipitates some higher molecular weight DNA contaminants and some of the RNA.

Final DNA Precipitation: Following the 4% PEG-8000 treatment, the material was centrifuged at 12,000 rpm for 30 minutes. The supernatant was decanted and additional 30% PEG-8000 in 1.6 M NaCl was added so that the final concentration of PEG-8000 was 10% (w/v). This was incubated at 4° C. for a minimum of 8 hours. It was then centrifuged as described above. The pellet was drained and then resuspended in a small volume (<10 mLs) of TE. One-tenth volume of 3M sodium acetate pH 5.2 was added and then 2 volumes of ethanol were added. This was incubated at −20° C. for a minimum of 1 hour. This was centrifuged at 12,000 rpm at 4–10° C. for 30 minutes and resuspended in a small amount of column buffer (TE+150 mN NACl, pH 8.0).

Gel Filtration Chromatography: A Pharmacia S-1000 (Pharmacia, Piscataway, N.J.) size exclusion column was poured in two Pharmacia XK26/100 columns with a final bed height of 80–85 cm (2.6×80 cm) each resulting in a total column volume of approximately 900 mLs. The columns were individually pressure packed in one direction, reversed and connected in series for equilibration and operation. The column was equilibrated in TE+150 mN NaCl, pH 8.0 and run at a flow rate of 0.75 mLs/min or 17 cm/hr.

Partially purified plasmid DNA was dissolved in 4–9 mLs of the above buffer, filtered through a syringe filter and loaded onto the column. Column operation and fractionation were automated with a Pharmacia FPLC (Pharmacia, Piscataway, N.J.).

Fractions (approximately 0.5–1% of column volume) were collected over the product elution zone and analyzed by 0.8% agarose gels. The exact range of product elution was determined from the gel analysis. Appropriate fractions were pooled and precipitated with 2 volumes of cold ethanol.

The ethanol precipitated bulk DNA was spun at 12,000 rpm for 30 minutes at 4–10° C. The pellets were drained in a laminar flow hood for 15–45 minutes, inverted and air dried for 5–15 minutes.

The pellet was resuspended in injection vehicle. Once the pellet was resuspended, a sample was given to QC to determine the concentration. This information was required so that a final dilution to 0.25 mg/mL±–0.5 mg/mL could be made. The DNA at this concentration was then filtered through a 0.2 μm syringe filter into a pyrogen-free container. Samples were taken for sterility testing and for QC, then aliquoted into 6.0 mL (1.5 mg) units, and stored frozen at −70° C. in a locked box. The aliquots were labeled with a description of the product, Lot #, Part #, volume, concentration, and date. This information was entered into inventory control for later final formulation, sterile fill and finish.

Following chromatography, the column and FPLC was sanitized with at least one column volume of 0.1 M NaOH.

In-Process Quality Control Testing

In process quality control was applied at the following manufacturing steps. Details of these in process quality control steps are described below.

TABLE

IN PROCESS QUALITY CONTROL TESTING

| Manufacturing Steps | In Process Quality Control | |
|---|---|---|
| Host Cell Transformation: Cell Paste | Identity: | mini-prep analysis restriction enzyme cuts |
| Master Cell Bank (MCB): Cell Paste | Plasmid Identity: | mini-prep analysis restriction enzyme cuts *E. coli* characterization |
| Manufacturer's Working Cell Bank (MWCB): Cell Paste | Plasmid Identity: | mini-prep analysis restriction enzyme cuts *E. coli* characterization |
| Fermentation: Cell Paste | Identity: | mini-prep analysis restriction enzyme cuts |
| Purification: Gel Filtration Chromatography purified DNA | Purity: | Agarose Gel Electrophoresis |
| | Concentration | $A_{260}$ |

Cell paste was tested for quality by mini-prep analysis, and restriction enzyme cuts were made to confirm the identity of the plasmid. Cultured cells from the Master Cell Bank, Manufacturer's Working Cell Bank, and manufactured cell paste batches were analyzed qualitatively to identify the presence of the IL-2 plasmid.

An aliquot of the culture was purified using a miniprep system, based on the Promega Wizard™ kit protocol (Promega, Madison, Wis.). The miniprep purified plasmid was analyzed with agarose gel electrophoresis, using three sets of restriction enzyme cuts run against a 1 Kb linear DNA standard ladder, along with uncut plasmid run against a supercoiled DNA ladder.

For the miniprep, aseptically obtained cells were pelleted by centrifugation. The pelleted cells were lysed with a lysis solution provided in the kit, and the cell debris was separated by centrifugation. The supernatant was removed and mixed with kit DNA purification resin. The supernatant-resin mixture was loaded into a kit mini-column. The resin was washed with kit column wash solution with centrifuge spinning to pass the wash solution through the column.

The DNA was then eluted from the resin with TE buffer and analyzed by agarose gel electrophoresis. The size of the uncut plasmid approximated 4900 bp. The restriction enzyme fragment sizes approximated the predicted fragments for cuts of the IL-2 plasmid with restriction enzymes.

Agarose gel electrophoresis was run on the fractions generated from gel filtration chromatography in order to determine which fractions contain supercoiled DNA, and which fractions contain contaminating chromosomal DNA and RNA. Fractions containing supercoiled DNA were pooled, ethanol precipitated and stored at −20° C. until required for preparation of Standard Bulk Plasmid DNA.

Standard Bulk Plasmid DNA Quality Control

The Standard Bulk Plasmid DNA was tested according to written procedures and specifications.

TABLE

SPECIFICATIONS FOR STANDARD BULK PLASMID DNA

| Test | Analytical Method | Specification | SOP # |
|---|---|---|---|
| Appearance | Visual | Clear, colorless solution | QC-0027 |
| Concentration | UV Absorbance, A260 | 0.6 ± 0.06 mg/mL<br>0.2 ± 0.01 mg/mL | QC-0027 |
| Total Size | Agarose Gel Electrophoresis | Approximates 4900 bp | QC-0004 |
| Restriction Sites | Agarose Gel Electrophoresis, Restriction Enzyme Analysis | Approximates predicted bp:<br>Xho I 4900 bp<br>EcoRI 1900 bp<br>3000 bp<br>NcoI 1100 bp<br>3800 bp | QC-0004 |
| Circular Plasmid DNA | Agarose Gel Electrophoresis | >95% (of visualized nucleic acids) | QC-0004 |
| Protein | Protein Slot Blot | <0.016 μg/μg plasmid DNA | QC-0003 |
| RNA | Agarose Gel Electrophoresis | Non-Visualized by Ethidium Bromide Stain | QC-0004 |
| *E. coli* DNA | Southern Slot Blot | <0.01 μg/μg plasmid DNA | QC-0032 |
| Endotoxin | LAL Gel Clot | <0.1 EU/μg plasmid DNA | QC-0002 |
| Bulk Sterility | USP Direct Transfer | No Growth through 14 days | QC-0058 |

Analytical Methods

UV Absorbance (SOP #QC-0027): Double stranded DNA absorbs a maximum amount of UV light at a wavelength of 260 nm. By finding the extinction coefficient for double stranded DNA the relationship of absorbance to concentration was found to be that 1 absorbance unit is equal to 50 μg/mL of plasmid. From this the concentration of a dilute plasmid sample was calculated.

Agarose Gel Electrophoresis (SOP #QC-0004): Agarose gel electrophoresis is a technique for the analytical separation of nucleic acids based on their molecular weights and conformation. Large molecules behave differently in a charged field and can be separated based on their charge densities. Their varying abilities to move through this field or their electrophoretic mobility creates a banding effect similar to a chromatographic technique, so a wide variety of species was separated and inspected. These included chromosomal DNA, various forms of plasmid DNA, and RNA. By running a molecular weight standard curve or ladder, size determinations were also made.

Restriction Enzyme Digestion (SOP #QC-0004): Large DNA molecules have many sites along their chain length where specific nucleases may react and cleave the chain. Generally, there are a number of sites which are quite specific and occur a finite number of times. Bacteria often use this fact to destroy non-genomic DNA by enzymatically looking for certain sequence sites or "restriction sites." One type of nucleases which carries out this function are restriction endonucleases. Restriction endonucleases cleave DNA sequences at highly specific sites which occur very infrequently. By examining enzymatically treated or "digested" samples on an agarose gel against a standard, the size of the fragments can be ascertained and a positive identification based on the fragmentation pattern can be made. Several combinations of restriction enzymes were investigated and it was determined that XhoI, EcoRI, NcoI were appropriate for IL-2 plasmid identification by agarose gel electrophoresis.

Southern Slot Blot Analysis (SOP #QC-0032): The Southern slot blot analysis is a modification of a Southern blot, which is a procedure for detecting known nucleic acid sequences by hybridization. This assay was developed to determine the presence of host genomic DNA in purified plasmid DNA samples. A plasmid DNA sample was denatured and immobilized onto a positively charged membrane which was sandwiched in a slot blot apparatus. The sample was concentrated into a slot. A labeled host DNA probe was used for hybridization. Linearized host DNA was labeled by random primed incorporation of digoxigenin labeled deoxyuridine-triphosphate (DIG-dUTP). Detection of hybridization of the probe to target DNA was done by using an enzyme linked antibody to digoxigenin (alkaline phosphate linked anti-digoxigenin) and visualized by using the substrates X-phosphatase (5-bromo-4-chloro-3-indolyl phosphatase) and NBT (nitroblue tetrazolium salt). By running a genomic DNA standard curve, targeted genomic DNA sequences were analyzed quantitatively for the presence of genomic DNA. Protein Slot Blot Assay (SOP #QC-0003): Plasmid sample with protein was fixed to a hydrophobic microporous PVDF membrane and fixed with 10% acetic acid. This membrane was then stained with coomassie brilliant blue which is selective for protein and does not stain nucleic acid.

LAL Gel Clot Assay (SOP #QC-0002): The Limulus Amebocyte Lysate (LAL) analytical method was based on the method described in United States Pharmacopeia (USP).

Sterility (SOP #QC-0058): Sterility was performed following the United States Pharmacopeia (USP) Procedure for Direct Transfer to Test Media. A 1 mL of sample was aseptically transferred to a vessel containing a minimum of 15 mL of sterile Fluid Thioglycollate Medium, and mixed, being careful not to aerate excessively, then incubated at 30 to 35° C. for 14 days.

Formulation

The drug product is a lipid/DNA complex composed of the IL-2 plasmid DNA with DMRIE/DOPE lipid mixture in an injection vehicle. The plasmid DNA/lipid complex is provided to the clinical site in final dosage form as individual vials for injection.

Four formulations corresponding to the four DNA clinical doses (10 μg, 30 μg, 100 μg, and 300 μg) were prepared.

The details of the formulations are described in the following table. The components were formulated in 1.2 mL of injection vehicle for each dose.

TABLE

| FORMULATION | DNA Dose | | | |
|---|---|---|---|---|
| | 10 μg | 30 μg | 100 μg | 300 μg |
| IL-2 plasmid DNA (μg) | 10 | 30 | 100 | 300 |
| DMRIE/DOPE (μg) | 4 | 12 | 40 | 120 |

1.2 mL of the IL-2 plasmid DNA/lipid complex formulated in the injection vehicle at 0.01 mg DNA/mL, 0.03 mg DNA/mL, 0.10 mg DNA/mL, or 0.30 mg DNA/mL was aseptically filled in 2-mL type I clear glass vials and packaged with 13 mm Teflon-coated gray butyl stoppers and aluminum seals. Detailed descriptions of the formulation for the four different DNA concentrations follow.

TABLE

| PLASMID DNA/DMRIE/DOPE LIPID MIXTURE FORMULATION | |
|---|---|
| **10 μg Dose** | |
| IL-2 plasmid DNA | 0.10 mg/mL |
| DMRIE/DOPE lipid | 0.004 mg/mL |
| **30 μg Dose** | |
| IL-2 plasmid DNA | 0.03 mg/mL |
| DMRIE/DOPE lipid | 0.012 mg/mL |
| **100 μg Dose** | |
| IL-2 plasmid DNA | 0.1 mg/mL |
| DMRIE/DOPE lipid | 0.04 mg/mL |
| **300 μg Dose** | |
| IL-2 plasmid DNA | 0.03 mg/mL |
| DMRIE/DOPE lipid | 0.012 mg/mL |

Standard Bulk Plasmid DNA

Standard Bulk Plasmid DNA was prepared by adjusting the concentration of the purified IL-2 plasmid DNA to 0.20 mg/mL or 0.60 mg/mL with sterile injection vehicle. The standard bulk was then sterile filtered through a 0.2 mm membrane in an aseptic laminar hood and stored frozen until delivery to formulation.

TABLE

STANDARD BULK PLASMID DNA PREPARATION

Figure 3:
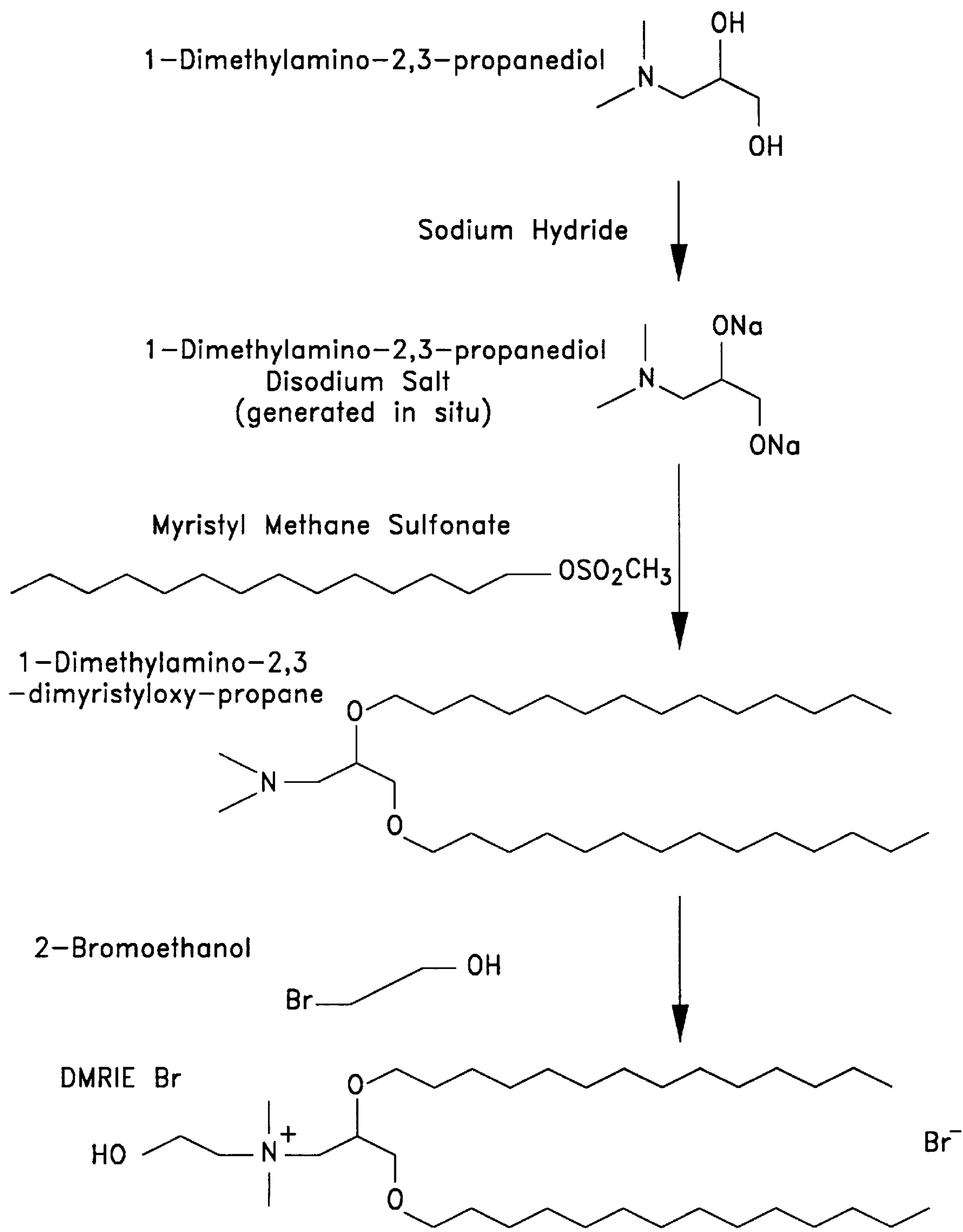
FIG. 3. DMRIE-Br Synthesis. Release Analyses: $^1$H-NMR, IR, TLC, water content, element analysis.

Column Purified Plasmid DNA
↓
Concentration adjustment
↓
Standard Bulk Plasmid DNA
↓
Sterile filtration
↓
Frozen Storage
↓
Delivery to Formulation DRMIE-Br The DMRIE-Br lipid was prepared as illustrated in FIG. 3. Its step-wise synthesis is represented in the following table.

TABLE

STEP-WISE SYNTHESIS OF DMRIE

- Sodium Hydride in mineral oil
- Triturate 3X with dry hexane under Argon gas
- Sodium Hydride
  - Add THF and Ar gas with stirring
  - Add drop-wise 3-dimethylamino-propanediol in dry THF
- Heat to reflux for 17 hours
- Add drop-wise tetradecylmethane sulfonate in dry THF
- Reflux for an additional 52 hours
- Cool solution, filter through Celite® diatomaceous earth, and evaporate
- Dissolve in an appropriate volume of ether and wash with 1/4 volumes of 1.0 N sodium hydroxide and 2 × 1/4 volumes water
- Dry with magnesium sulfate, filter and evaporate with high vacuum
- Silica gel chromatography with a step-wise gradient of 90:10 to 50:50 hexane/ether, then neat ether
- TLC analysis of collected column fractions
- Pool pure fractions and evaporate, dissolve in ether, filter and evaporate with high vacuum TABLE-continued

STEP-WISE SYNTHESIS OF DMRIE

- Analysis of intermediate product: TLC, IR, NMR
- Crude (2,3-dimyristyloxy) propyl, dimethylamine
- Add dry DMF and Ar gas with stirring
- Add 2 molar equivalents of 2-bromoethanol
- Heat to 100° C. for 24 hours
- Vacuum distillation at room temperature to 45° C., then vacuum overnight
- Silica column chromatography with a step-wise gradient from 90:10:0.25:0.25 to 80:20:0.25:0.25 chloroform:methanol:ammonia: water
- TLC analysis of collected column fractions
- Pure fractions are pooled, azeotroped with addition and evaporation of 95:5 chlororform:methanol, dried, dissolved in chloroform, filtered, and evaporated with high vacuum
- TLC analysis of material
- Pure (2,3 dimyristyloxy) propyl, dimethylamine
- Rechromatograph under identical conditions
- Store material in quarantine at -23° C.~-8° C. under dry conditions
- Samples are taken for QC analysis: TLC, IR, water content, elemental analysis and in vitro gene transfection
- Release upon approval by QC
- DMRIE-Br DMRIE-Br Bulk Quality Control The DMRIE-Br Bulk was tested according to written procedures and specifications.

TABLE

SPECIFICATIONS FOR DMRIE-BR BULK

| Test | Analytical Method | Specification | SOP # |
|---|---|---|---|
| Identity | | | |
| Appearance | Visual Observation | White solid | QC-0040 |
| IR | Infrared Spectroscopy | conforms to structure | QC-0041 |
| Purity | | | |
| TLC | TLC Analysis Basic system Neutral system Acidic system | Single spot elutes with the same $R_f$ of the reference sample | QC-0011 |
| Elemental Analysis | Elemental Analysis Carbon Hydrogen Nitrogen | Calculated percent value ± 0.6% | QC-0069 |
| Expression | In Vitro Assay for Transfection Efficiency | Reported value | QC-0033 |

Analytical Methods

Appearance (SOP #QC-0040): Visual examination of the raw material took place in a clear test tube and color, clarity, gross viscosity, crystallinity, etc. was noted. In addition, the bulk of the lot was visually screened for any contaminants.

Infrared Spectroscopy (SOP #QC-0041): A sample was prepared as a thin film, a chloroform solution, a KBr "pellet," or a Nujol mull as appropriate to the specific material. A spectra derived by recording light absorbance as a function of wavelength was recorded and then analyzed on the basis of characteristic functional group patterns and/or compared with a similarly obtained spectrum of a standard material.

Thin Layer Chromatography (TLC) (SOP #QC-0011): Applying functional group specific reagents, visualization under short wave Uw light, and 10% sulfuric acid spray with "charring" were utilized. The $R_f$s (the speed of compound motion relative to the rise of the carrier liquid, 2:1 ether hexane) were characteristic for the system.

Elemental Analysis (SOP #QC-0069): The weight percentages of the elements in a material are a function of the molecular formula (including water of hydration) and elemental weights. Thus, since they are determined strictly mathematically based on standard chemical conventions, these percentage values are invariant and represent relative proportions expected of 100% pure material. The amounts of the individual elements were determined in several ways. For Carbon, Hydrogen and Nitrogen, a weighed sample was burned in oxygen and the amounts of $CO_2$, $H_2O$, and $NO_2$ were determined. For halide and phosphates other chemical analyses were used. Oxygen was not explicitly determined, but was calculated as the difference from 100 and the total of the other elements.

In Vitro Assay for Transfection Efficiency of the Cationic Lipid Drug Product (SOP #QC-0033): CV1 or COS.7 cells were seeded at 20,000 cells per well in a 96 well flat bottom plate and incubated overnight at 37° C., 5%–10% $CO_2$. Cells were approximately 80–90% confluent before transfection.

A reference lot of DMRIE/DOPE was assayed side by side with the sample lot. The cationic lipid product was hydrated or diluted to 0.672 mM. Two fold serial dilutions of the hydrated lipid were performed through 8 plate columns in a fresh 96 well round bottom plate, using OPTI-MEM.

pRSVlacZ DNA was prepared by diluting with OPTI-MEM to 0.08 mg DNA/ml. Two-fold dilutions with OPTI-MEM were prepared in a fresh 96 well plate down through 8 rows.

The DNA was complexed with the lipid by transferring 60 $\mu$l from each well of the DNA dilution plate to the corresponding well of the lipid plate. The solutions were mixed by gentle tapping of the plate, and used for transfection between 15 and 60 minutes after complexion.

100 $\mu$l lipid/DNA complex was added per well over the seeded cell plate (after removing the previous media from the cell plate). The cells were incubated at 37° C., 5% $CO_2$, for 4 hours. 100 $\mu$l of 30% FCS or BCS in OPTI-MEM was added per well at 4 hours post-transfection. 100 $\mu$l of 10% FCS or BCS in OPTI-MEM was added per well at 24 hours post-transfection. Incubation continued for a total of 48 hours post-transfection.

Cells were harvested, lysed with lysis buffer (Triton-X 100 in 250 mM Tris, pH 8), and assayed for beta-galactosidase expression using a CPRG color substrate reaction and a beta-galactosidase standard curve. The red color developed was measured at 580 nm with a microtiter plate reader. The sample result was estimated by the standard curve and compared with the reference lot result.

DOPE

The DOPE lipid was synthesized by Avanti Polar Lipids, Inc., Alabaster, Ala.

DMRIE/DOPE Lipid Mixture Preparation

DMRIE-Br and DOPE were mixed together in chloroform in a sterile glass container. The organic solvent was removed by evaporation under reduced pressure, and the lipid film was held overnight in vacuo. The lipid mixture was hydrated with sterile water for injection. The bulk aqueous lipid mixture was sterilized and stored refrigerated until it was mixed with the IL-2 plasmid DNA.

The preparation of the DMRIE/DOPE mixture is represented in the following table.

TABLE

DMRIE AND DOPE MIXING

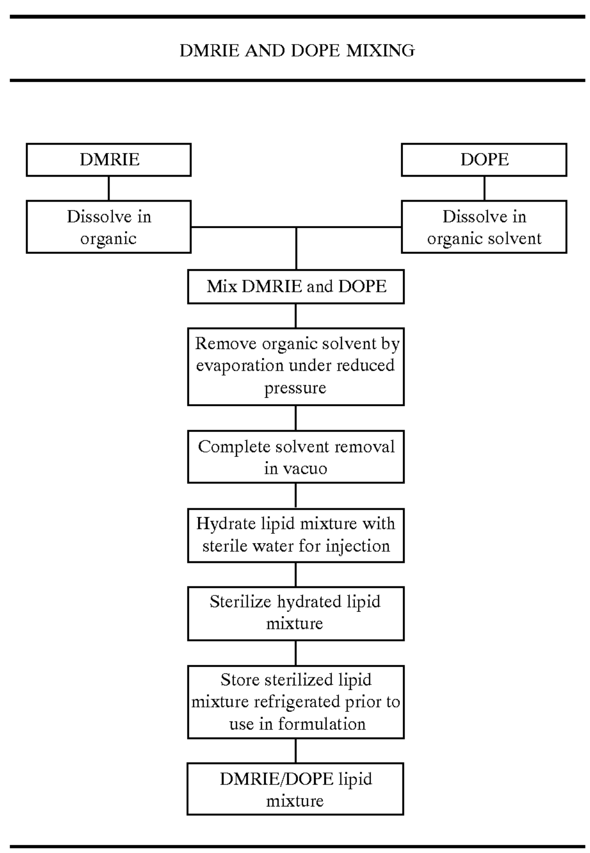

Formulation/Fill

Sterilized hydrated DMRIE/DOPE lipid mixture prepared as described was received from formulation. The standard bulk plasmid DNA was received frozen from production in injection vehicle, thawed at room temperature, and sterile-filtered through a 0.2 mm sterile membrane. The plasmid DNA solution was stored at room temperature until combination with the DMRIE/DOPE solution. The DMRIE/DOPE solution and plasmid DNA solution were combined The DNA/lipid complex mixture was immediately aseptically filled into sterile 2-mL Type 1 glass vials and sealed with sterile 13-mm Teflon-faced gray butyl stoppers. Aluminum crimps were applied to secure the seal. The vials were labeled and placed in quarantine at −20° C. pending QC release. The formulation/fill process is outlined in the following table.

TABLE

FORMULATION/FILL PROCESS

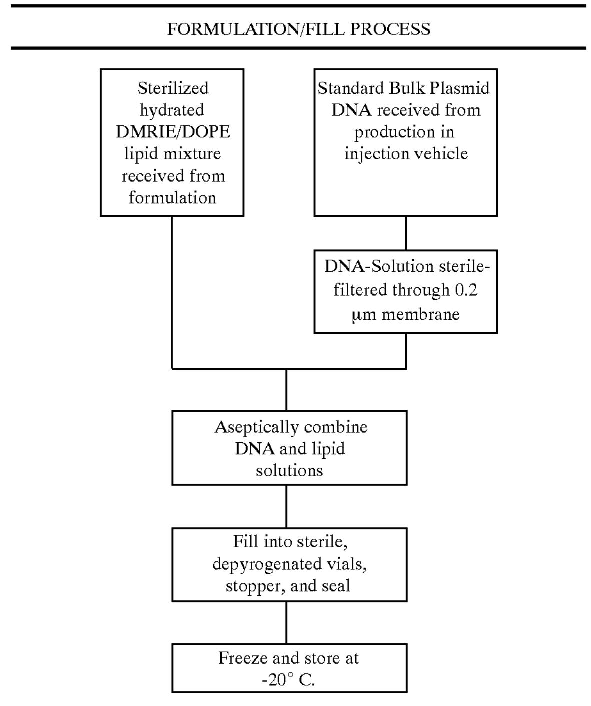

Fill Release

The final filled vials of plasmid DNA, DMRIE/DOPE lipid complex were tested according to written procedures and specifications.

Release Specifications for 10 μg Dose
PLASMID DNA, DMRIE/DOPE LIPID COMPLEX
10 μg Dose, 1.2 ML/VIAL

| Test | Specification | Method | SOP # |
|---|---|---|---|
| Solution appearance | White Opalescent Solution | Visual Observation | QC-0027 |
| Concentration | 10 ± 1 μg/mL | UV Absorbance A260 | QC-0027 |
| Total Size | Approximates 4900 bp | Agarose Gel Electrophoresis | QC-0004 |
| Circular Plasmid DNA | >95% of visualized nucleic acids | Agarose Gel Electrophoresis | QC-0004 |
| Residual Ethanol | <500 ppm | GC | QC-0059 |
| Pyrogen | Not pyrogenic at 5 μg/Kg Rabbit Body Weight | Rabbit pyrogen, USP | QC-0060 |
| Sterility | No growth through 14 days | USP Direct Transfer | QC-0058 |
| Gene Expression | 50% to 200% of reference | In vitro transfection ELISA | QC-0061 |
| General Safety Test | Passes | USP General Safety Test | QC-0062 |

Release Specifications for 30 μg Dose
PLASMID DNA, DMRIE/DOPE LIPID MIXTURE
30 μg Dose, 1.2 ML/VIAL

| Test | Specification | Method | SOP # |
|---|---|---|---|
| Solution appearance | White Opalescent Solution | Visual Observation | QC-0027 |
| Concentration | 30 ± 3 μg/mL | UV Absorbance | QC-0027 |
| Total Size | Approximates 4900 bp | Agarose Gel Electrophoresis | QC-0004 |
| Circular Plasmid DNA | >95% of visualized nucleic acids | Agarose Gel Electrophoresis | QC-0004 |
| Residual Ethanol | <500 ppm | GC | QC-0059 |
| Pyrogen | Not pyrogenic at 5 μg/Kg Rabbit Body Weight | Rabbit pyrogen, USP | QC-0060 |
| Sterility | No growth through 14 days | USP Direct Transfer | QC-0058 |
| Gene Expression | 50% to 200% of reference | In vitro transfection/ ELISA | QC-0061 |
| General Safety Test | Passes | USP General Safety Test | QC-0062 |

Release Specifications for 100 μg Dose
PLASMID DNA, DMRIE/DOPE LIPID MIXTURE
100 μg Dose, 1.2 ML/VIAL

| Test | Specification | Method | SOP # |
|---|---|---|---|
| Solution appearance | White Opalescent Solution | Visual Observation | QC-0027 |
| Concentration | 0.10 ± 0.01 μg/mL | UV Absorbance | QC-0027 |
| Total Size | Approximates 4900 bp | Agarose Gel Electrophoresis | QC-0004 |
| Circular Plasmid DNA | >95% of visualized nucleic acids | Agarose Gel Electrophoresis | QC-0004 |
| Residual Ethanol | <500 ppm | GC | QC-0059 |
| Pyrogen | Not pyrogenic at 5 μg/Kg Rabbit Body Weight | Rabbit pyrogen, USP | QC-0060 |
| Sterility | No growth through 14 days | USP Direct Transfer | QC-0058 |
| Gene Expression | 50% to 200% of reference | In vitro transfection/ ELISA | QC-0061 |
| General Safety Test | Passes | USP General Safety Test | QC-0062 |

Release Specifications for 300 μg Dose
PLASMID DNA, DMRIE/DOPE LIPID MIXTURE
300 μg Dose, 1.2 ML/VIAL

| Test | Specification | Method | SOP # |
|---|---|---|---|
| Solution appearance | White Opalescent Solution | Visual Observation | QC-0027 |
| Concentration | 0.3 ± 0.03 μg/mL | UV Absorbance | QC-0027 |
| Total Size | Approximates 4900 bp | Agarose Gel Electrophoresis | QC-0004 |
| Circular Plasmid DNA | >95% of visualized nucleic acids | Agarose Gel Electrophoresis | QC-0004 |
| Residual Ethanol | <500 ppm | GC | QC-0059 |
| Pyrogen | Not pyrogenic at 5 μg/Kg Rabbit Body Weight | Rabbit pyrogen, USP | QC-0060 |
| Sterility | No growth through 14 days | USP Direct Transfer | QC-0058 |
| Gene Expression | 50% to 200% of reference | In vitro transfection/ ELISA | QC-0061 |
| General Safety Test | Passes | USP General Safety Test | QC-0062 |

Analytical Methods

Spectrophotometry (SOP #QC-0027): Spectrophotometry was performed as for the drug substance.

Agarose Gel Electrophoresis (SOP #QC-0004): Agarose gel electrophoresis was performed as for the drug substance.

Residual Ethanol (SOP #QC-0059): Residual ethanol was analyzed by gas chromatography methodology.

Rabbit Pyrogen (SOP #QC-0060): Rabbit pyrogen was evaluated by the United States Pharmacopeia (USP) Pyrogen Test, by intravenous injection of the test solution in rabbits. The plasmid DNA was diluted aseptically to 5 μg/10 ml with pyrogen-free, sterile vehicle and injected at 10 ml/kg body weight into each of 3 protein naive-rabbits. The rabbits' temperatures were recorded at not more than 30 minutes before injection ("control temperature"), and at 1, 1.5, 2, 2.5, and 3 hours after infection. If no rabbit showed an increase in temperature of 0.6° C. or more above its respective control temperature, and if the sum of the 3 individual maximum temperature rises did not exceed 1.4° C., the product met requirements for absence of pyrogens.

In Vitro Transfection for Coding Potential for IL-2 Expression (SOP #QC-0061): Potency of the IL-2 plasmid DNA was determined by IL-2 expression in transfected B16 cells. A working reference of the IL-2 plasmid DNA was used as a positive control and to determine the relative potency of the test sample. The absolute value of IL-2 expression (μg/well) of the test and reference samples were also reported.

200,000~400,000 B16 cells were seeded per well into 6-well plate the day before transfection. Cells were a >75% confluent monolayer prior to transfection. The IL-2 plasmid DNA/DMRIE/DOPE lipid complex sample was diluted to 5 μg DNA/ml with sterile vehicle. The cells were transfected with 1 mL of the complex solution per well in duplicate. Cells were incubated at 37° C., 5% $CO_2$ throughout the procedure. A reduced serum medium such as Opti-MEM supplemented with fetal calf serum was added to the cells at 3.5–4.5 and 23–24 hours post-transfection. Cell supernatant was harvested 46–48 hours post-transfection. IL-2 expression in the cell supernatants was measured by an enzyme amplified sensitivity immunoassay (Medgenix ELISA, Medgenix Diagnostics, Fleurus, Belgium).

Sterility (SOP #QC-0058): Sterility was performed following the Unites States Pharmacopeia (USP) Procedure for Direct Transfer to Test Media. A 1 ml of sample was aseptically transferred to a vessel containing a minimum of 15 ml of sterile Fluid Thioglycollate Medium, and mixed, being careful not to aerate excessively, then incubated at 30 to 35° C. for 14 days.

General Safety Test (SOP #QC-0062): The General Safety Test was performed as per United States Pharmacopeia (USP) methodology.

Release Protocol

Release protocols were designed for release of each lot of final vialed product.

Stability Data

Stability data is in the process of being collected showing long-term and short-term stability of the final vialed product.

Label Control

Label control and product labeling procedures were put into place.

Pharmacology

A series of pre-clinical studies was conducted to examine efficacy and safety of the IL-2 plasmid DNA.

The IL-2 plasmid was found to have antitumor activity in the murine subcutaneous B16 melanoma and Renca models.

These results are in marked contrast to the inability of other investigators to obtain change in tumor growth following treatment by the direct injection of DNA encoding IL-2 into B16 melanomas. Vile and Hart, Annals of Oncology 5 (Suppl 4): S59 (1994).

In the present preliminary animal studies, it was demonstrated that the direct intratumor injection of a plasmid DNA expression vector, containing the human IL-2 gene, reduced the incidence of tumor formation and slowed tumor growth. By local expression of cytokines at the site of the tumor, lower levels of cytokines should be required for efficacy as compared to systemic administration, and these levels should be sufficiently low to avoid producing toxicity in the patient but be adequate to generate an antitumor response by stimulating the immune system.

Antitumor Efficacy of IL-2 Plasmid DNA in the Murine Subcutaneous B16 Melanoma and Renca Models Objectives: The objectives of the studies described in this section were to evaluate the effect of the direct intratumor injection of plasmid DNA expression vectors encoding the human IL-2 gene in murine tumor models. The efficacy endpoint was measured as reduction in tumor volume. The following parameters were evaluated in this section:

i.) Formulation Screening ii.) Dose response Study iii.) Dose regimen iv.) DNA vs. IL-2 Protein Therapy v.) Efficacy in the subcutaneous Renca model (renal cell carcinoma)

Summary Results: The direct intratumor injection of a plasmid DNA expression vector encoding the human IL-2 gene into subcutaneous B16 melanoma tumors in mice significantly slowed tumor growth and reduced the incidence of palpable tumors. The greatest anti-tumor efficacy was achieved with the IL-2 plasmid DNA of the invention formulated with the cationic lipid DMRIE/DOPE. The anti-tumor response was found to be dose dependent and the optimum regimen was found to be a weekly intratumor injection of 50 μg of plasmid formulated with DMRIE/DOPE at a DNA/lipid mass ratio of 5:1. Formulation of DNA with DMRIE/DOPE enhanced the anti-tumor effect at DNA doses of less than 50 μg.

i. Formulation screening

Objectives: The study objective was to determine the optimum DNA/lipid ratio and to compare the cationic lipids DMRIE/DOPE vs. βAE-DMRIE for efficacy in the murine B16 model. The cationic lipids DMRIE/DOPE and βAE-DMRIE were compared at various DNA/lipid mass ratios. The efficacy end point was measured as reduction of tumor size and extension of survival period.

Methods: B16 melanoma cells (ATCC #CRL 6322) were maintained in DMEM supplemented with non-essential amino acids, glutamate, sodium pyruvate and 10% heat inactivated fetal bovine serum (FBS) at 37° C. and 5% $CO_2$. A single cell suspension was prepared for injection by detaching cells with trypsin/EDTA, washing and resuspending at a concentration of $1\times10^5$ cells/mL in DMEM without 10% FBS.

Plasmid DNA was diluted with normal saline to a concentration of 1.0 mg/mL. The bulk DMRIE/DOPE lipid was reconstituted with normal saline to a concentration of 0.96 mg/mL DMRIE and 1.12 mg/mL DOPE, and diluted with normal saline to give a final concentration of 0.192 mg/mL of DMRIE and 0.224 mg/mL of DOPE. Equal volumes of plasmid DNA at 1.0 mg/mL and DMRIE/DOPE were mixed by gentle vortexing to form the DNA/lipid complex. This resulted in 0.5 mg/mL of plasmid DNA, 0.096 mg/mL DMRIE and 0.112 mg/mL DOPE. The βAE/DMRIE complex was prepared by mixing βAE-DMRIE at 1.0 mg/mL with an equal volume plasmid DNA at 1.0 mg/mL which resulted in a final DNA/lipid ratio of 5:1. The administered volume of 100 μl/dose resulted in a 50 μg dose of DNA and approximately 10 μg of lipid. The DNA/lipid complex was stored on ice after mixing, but warmed to room temperature prior to injection and used immediately. DNA/lipid ratios of 2:1, 1:5, and 1:6 were also tested in tumor bearing mice. Female C57Bl/6 mice (10/group) were injected subcutaneously on the chest with 0.2 mL of B16 melanoma cells at $1.0\times10^5$ cells/mL for a total $2\times10^4$ cells. Twenty four hours post tumor injection, mice were treated by direct intratumor injection with 100 μl of one of the following: 1) the IL-2 plasmid DNA formulated with DMRIE/DOPE or βAE-DMRIE, 50 μg of DNA and 10 μg of lipid; or 2) normal saline (injection vehicle control). Mice were treated three times per week for three consecutive weeks. Tumor volume was measured by calipers three times per week.

Figure 4:
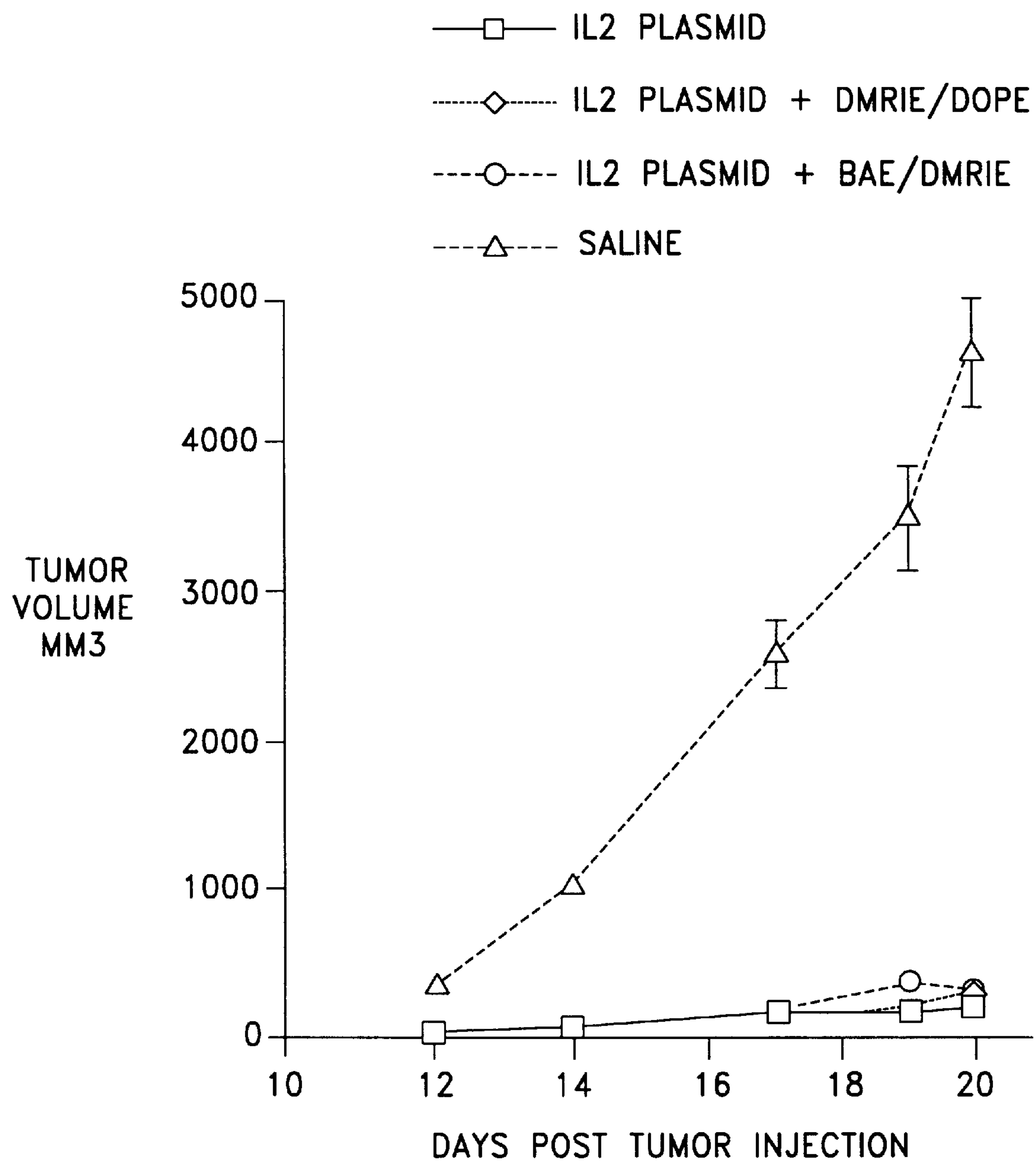
FIG. 4. Tumor regression in the B16 tumor bearing mice treated with IL-2 plasmid DNA plus DMRIE/DOPE or BAE/DMRIE at DNA:lipid ratio of 5:1 versus saline.

Results: Palpable tumors appeared by day 11 post tumor inoculation in all groups. Tumor volume was reduced significantly in the DNA+lipid treated groups compared to the control (FIG. 4). DNA/lipid ratios of 2:1, 1:5, and 1:6 resulted in lipid deposition at the site of injection, thus tumor volume could not be accurately measured.

Figure 5:
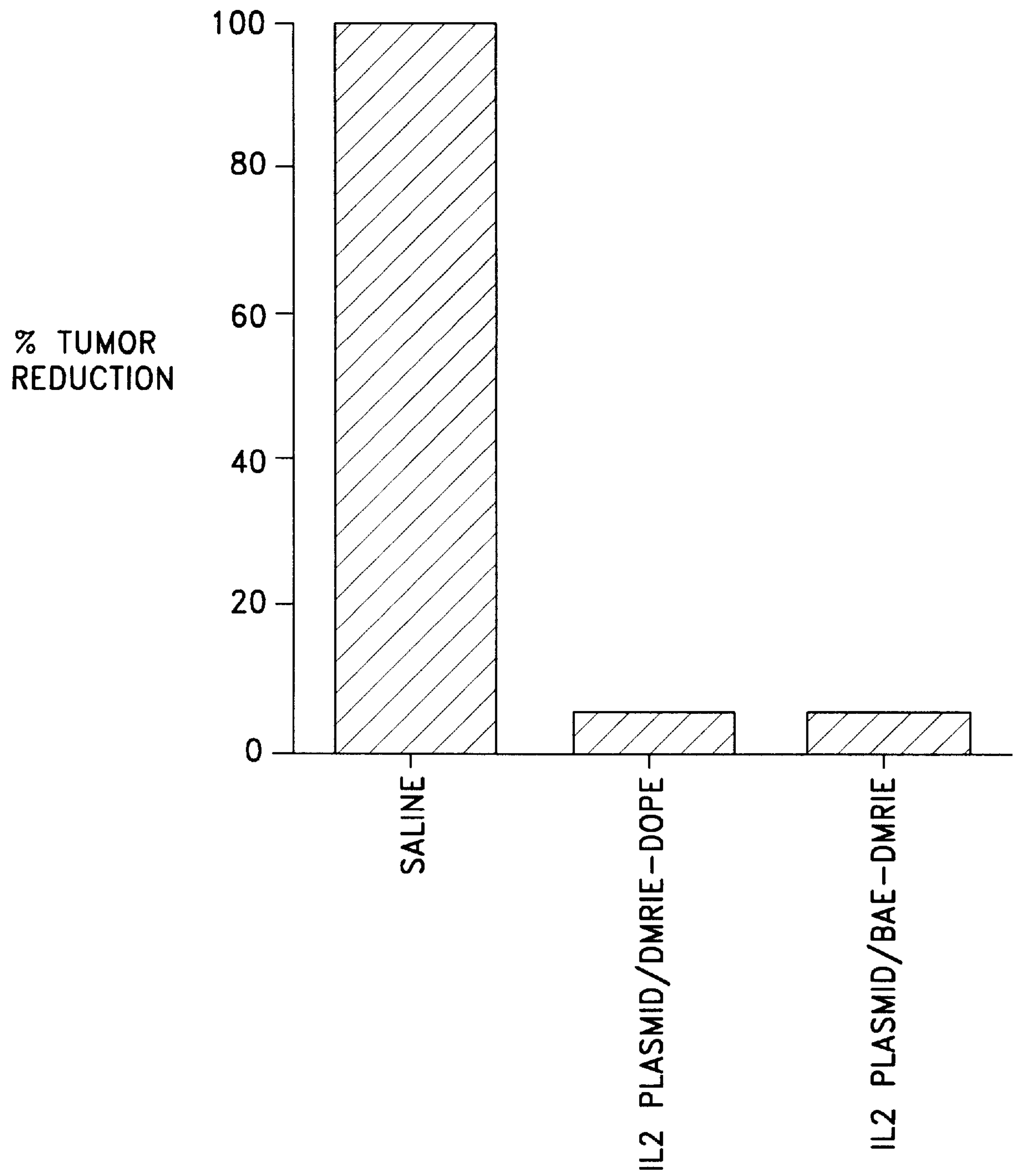
FIG. 5. Tumor reduction in B16 melanoma tumor bearing mice treated with IL-2 plasmid DNA plus DMRIE/DOPE or BAE-DMRIE twenty one days post tumor injection.

There was a 94 percent reduction in tumor volume in the IL-2 plasmid treated mice when the plasmid was formulated with either DMRIE-DOPE or βAE-DMRIE at a 5:1 DNA:lipid ratio (FIG. 5, $P<0.01$). In addition to tumor reduction, survival was enhanced in the treated groups as compared to the controls, 50–60% survival 2 weeks post therapy termination vs. 0% survival in the saline control (Table below).

TABLE

SURVIVAL AND TUMOR INCIDENCE IN MICE 5 WEEKS POST INJECTION WITH B16 MELANOMA CELLS.

| TREATMENT | % SURVIVAL | % TUMOR FREE |
|---|---|---|
| Plasmid alone | 60 | 10 |
| Plasmid + DMRIE/DOPE | 70 | 0 |
| Plasmid + βAE-DMRIE | 80 | 30 |
| DMRIE/DOPE alone | 0 | 0 |
| βAE-DMRIE alone | 0 | 0 |
| Saline | 0 | 0 |

Conclusions: A 5:1 DNA/lipid ratio was determined to be the optimal ratio for anti-tumor efficacy of the IL-2 plasmid. DNA in the B16 model.

ii. Dose response:

Objectives: The study goal was to determine the optimum plasmid DNA dose and optimum lipid, DMRIE/DOPE vs. βAE-DMRIE, for tumor reduction in the B16 melanoma tumor model. The efficacy end point was measured as reduction in tumor volume during a three week study.

Methods: For preparation of B16 cells for injection and preparation of the IL-2 plasmid DNA and cationic lipid formulation refer to i above.

Female C57BL/6 mice (10/group) were injected subcutaneously on the chest with 0.2 mL of B16 melanoma cells at $1.0\times10^5$ cells/mL for a total $2\times10^4$ cells. Twenty four hours post tumor injection, mice were treated by direct intratumor injection with 100 μl of one of the following:

1. IL-2 plasmid: 50 μg, 10 μg, 2 μg and 0.4 μg per injection;

2. IL-2 plasmid: formulated with DMRIE/DOPE or βAE-DMRIE at a DNA/lipid ratio of 5:1 and at DNA concentrations of 50 μg, 10 μg, 2 μg, and 0.4 μg per injection of DNA; or 3. Normal saline (injection vehicle control).

Mice were treated three times per week for three consecutive weeks.

Figure 6:
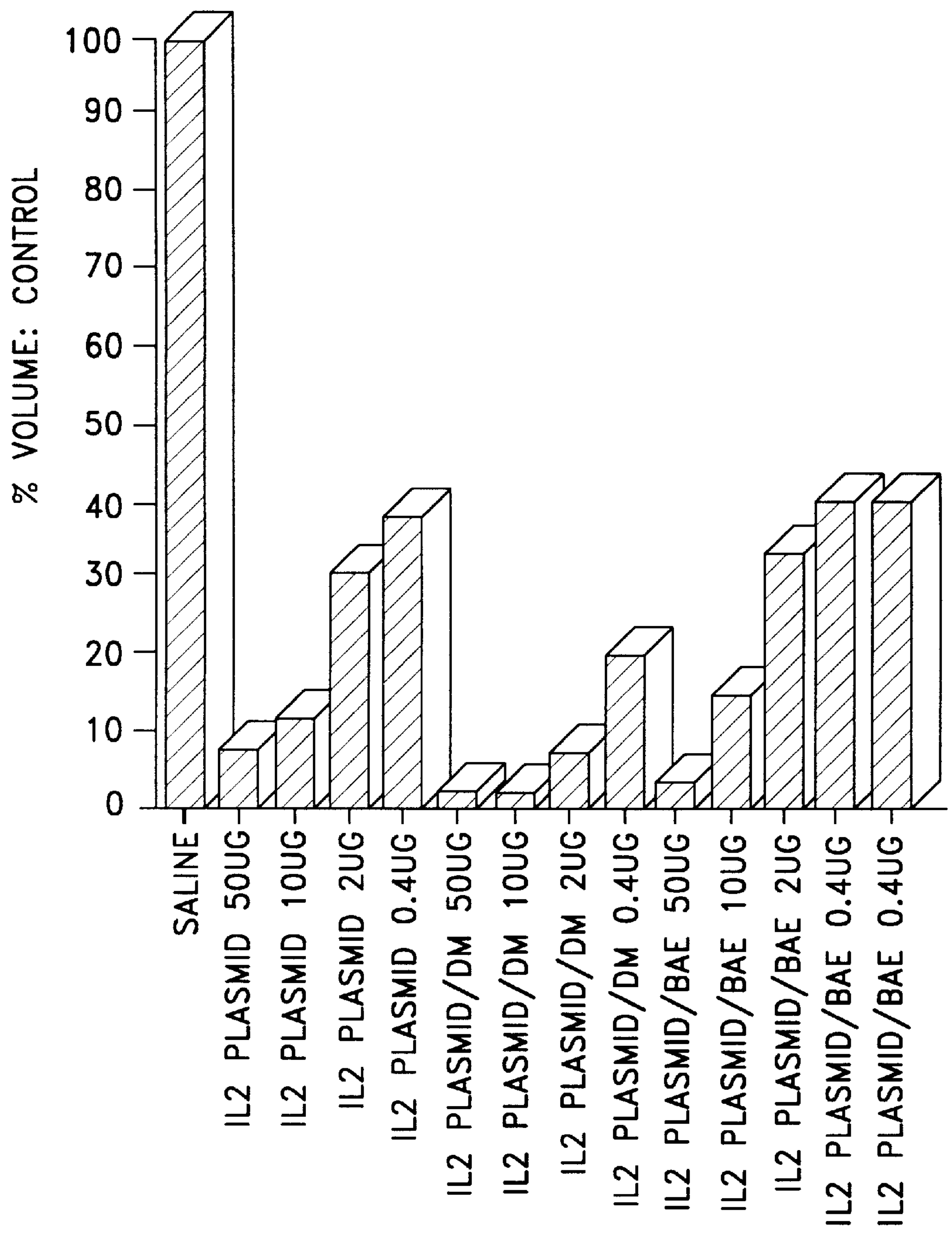
FIG. 6. Tumor reduction at day twenty one in B16 melanoma tumor bearing mice treated with IL-2 plasmid DNA alone or formulated with DMRIE/DOPE, BAE-DMRIE or saline.
Figure 7:
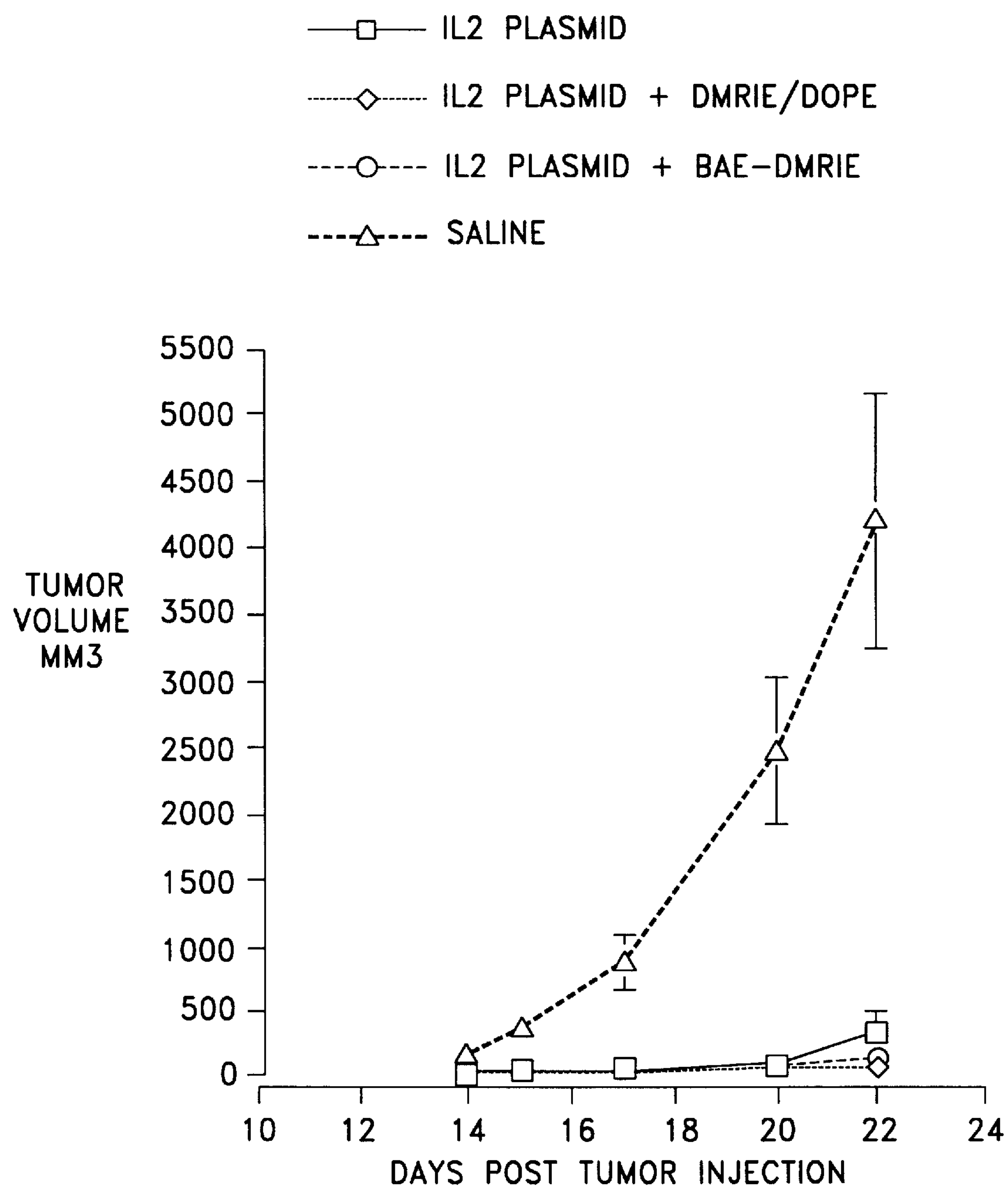
FIG. 7. Tumor growth in B16 melanoma tumor bearing mice treated with 50 $\mu$g IL-2 plasmid DNA alone or formulated with DMRIE/DOPE or BAE-DMRIE.
Figure 8:
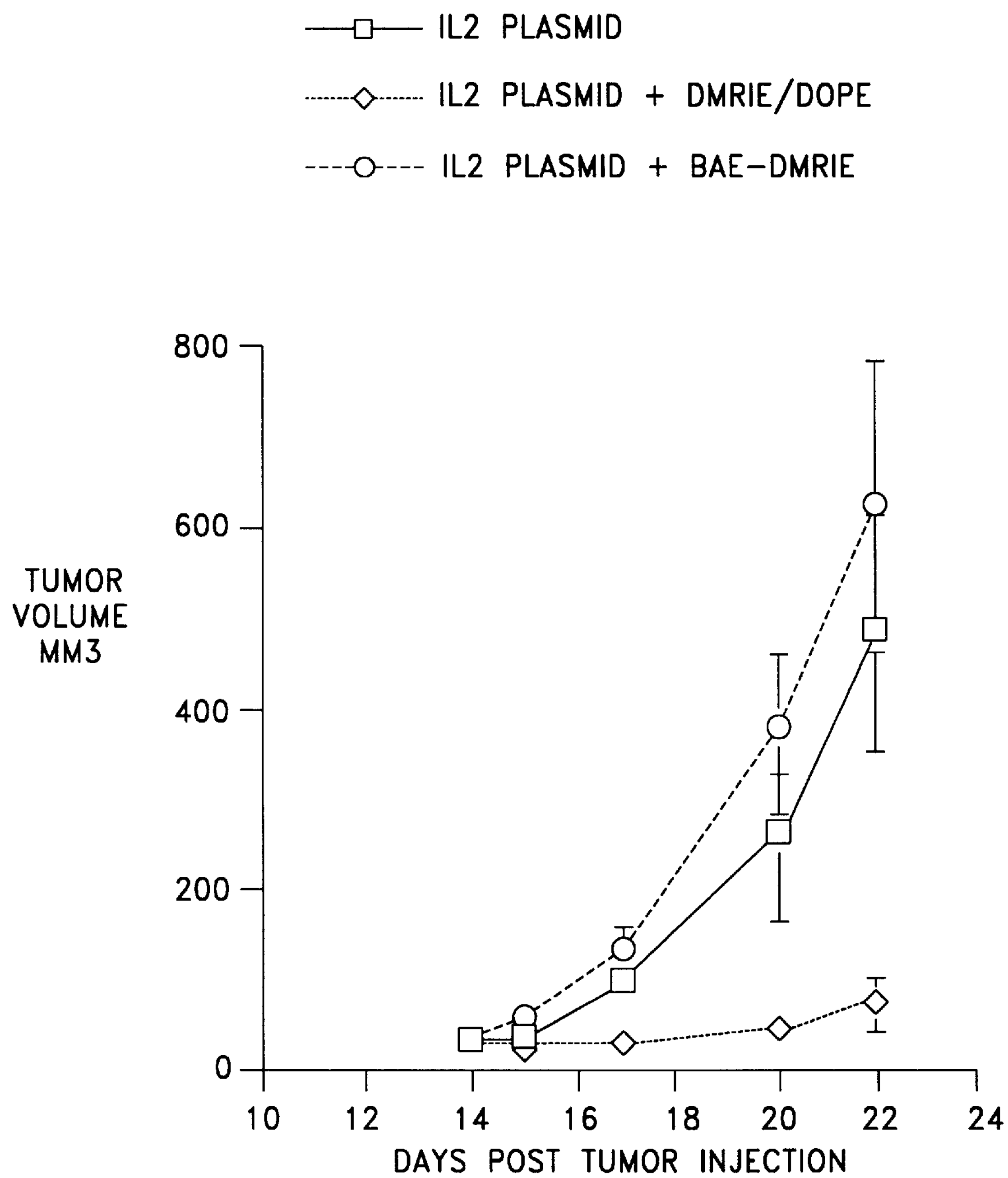
FIG. 8. Tumor growth in B16 melanoma tumor bearing mice treated with 10 $\mu$g IL-2 plasmid DNA alone or formulated with DMRIE/DOPE or BAE-DMRIE.
Figure 9:
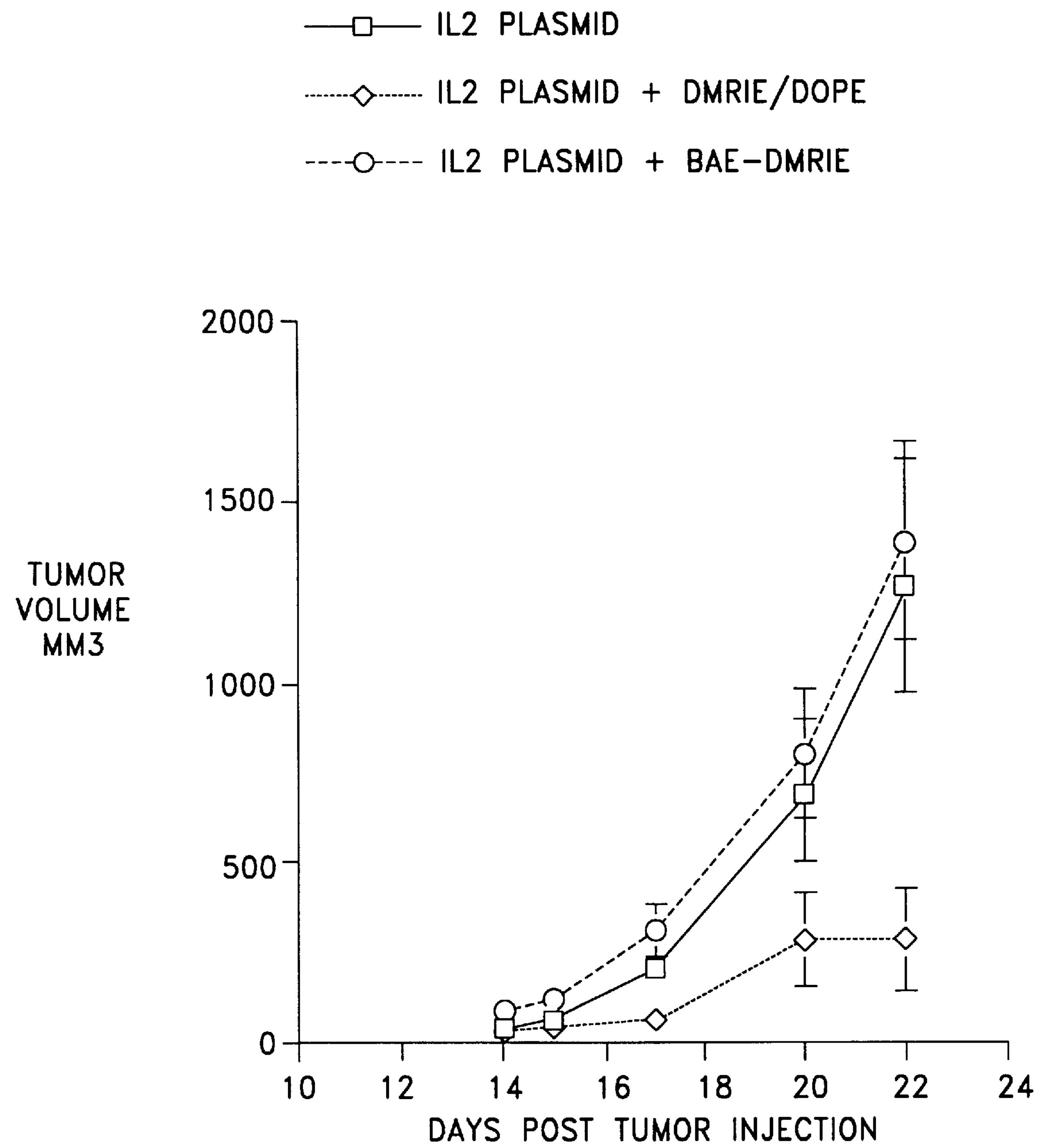
FIG. 9. Tumor growth in B16 melanoma tumor bearing mice treated with 2 $\mu$g IL-2 plasmid DNA alone or formulated with DMRIE/DOPE or BAE-DMRIE.
Figure 10:
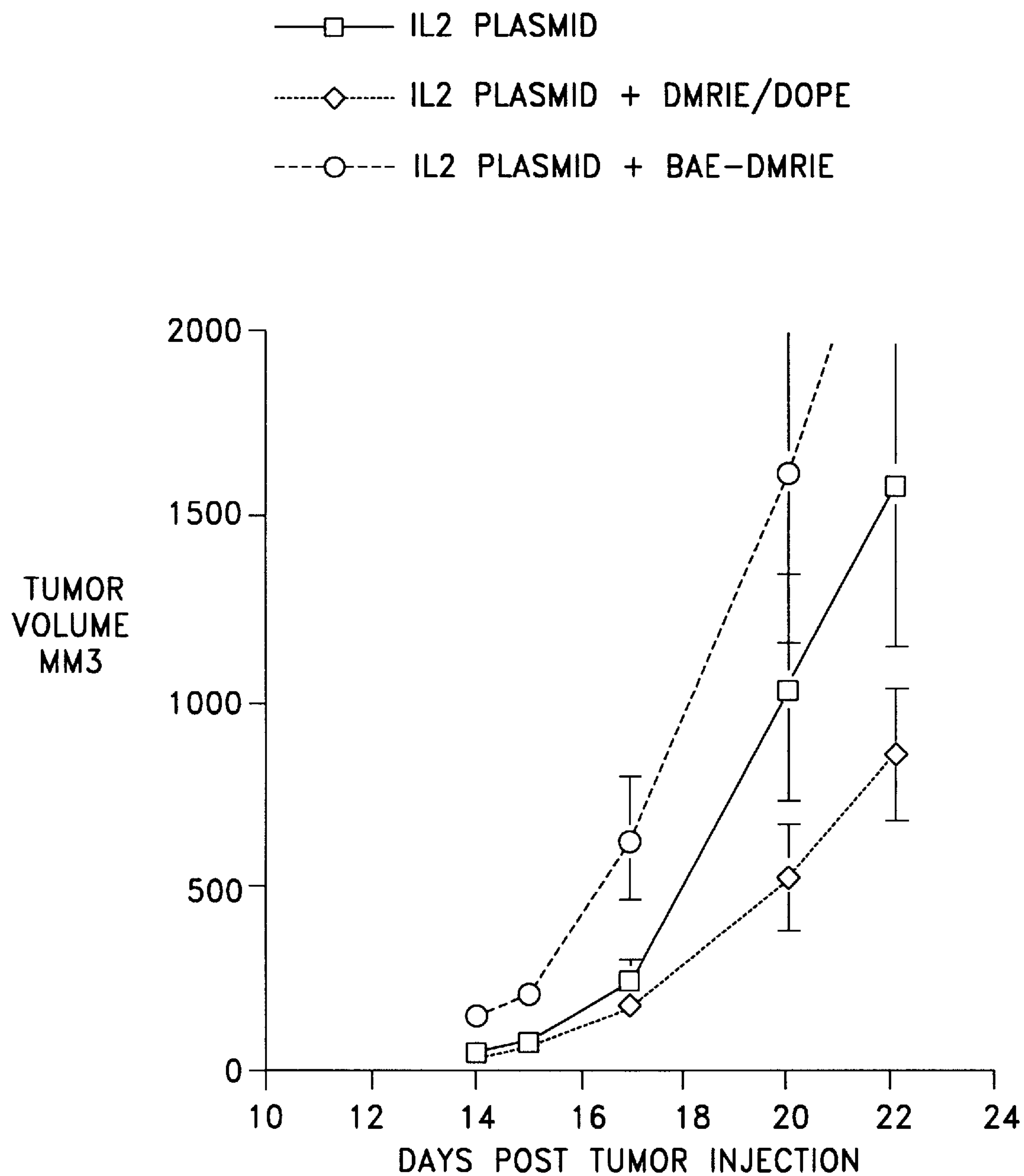
FIG. 10. Tumor growth in B16 melanoma tumor bearing mice treated with 0.4 $\mu$g IL-2 plasmid DNA alone or formulated with DMRIE/DOPE or BAE-DMRIE.

Results: A statistically significant, dose dependent anti-tumor response was observed for plasmid DNA alone or formulated with cationic lipid at DNA doses of 50 μg, 10 μg, 2 μg and 0.4 μg, (FIG. 6, Table below). At the 50 μg DNA dose, there was no significant difference in the tumor reduction observed for DNA alone vs. DNA formulated with DMRIE/DOPE or βAE-DMRIE (FIG. 7, Table below). At the 10 and 2 μg doses, tumor reduction was significantly enhanced when the DNA was formulated with DMRIE/DOPE as compared to DNA alone or DNA formulated with βAE-DMRIE (FIG. 8, FIG. 9, Table below). A significant anti-tumor response was observed even at the lowest dose of 0.4 μg of DNA alone or formulated with DMRIE/DOPE (FIG. 10). At this low dose, the formulations with DMRIE/DOPE did not significantly enhance the antitumor activity of the plasmid DNA (Table below). βAE-DMRIE did not significantly enhance the antitumor activity of the plasmid DNA of any of the doses tested (Table below).

TABLE

| TREATMENT | STATISTICAL ANALYSIS vs. SALINE | vs. DNA + DMRIE/DOPE[1] | vs. DNA + βAE-DMRIE[1] |
|---|---|---|---|
| DNA 50 μg | $p < 0.01$ | NS | NS |
| DNA 10 μg | $p < 0.01$ | $p < 0.01$ | NS |
| DNA 2 μg | $p < 0.05$ | $p < 0.05$ | NS |
| DNA 0.4 μg | $p < 0.05$ | NS | NS |
| + DMRIE/DOPE @ 50 μg DNA | $p < 0.01$ | — | NS |
| + DMRIE/DOPE @ 10 μg DNA | $p < 0.01$ | — | $p < 0.01$ |
| + DMRIE/DOPE @ 2 μg DNA | $p < 0.01$ | — | $p < 0.01$ |
| + DMRIE/DOPE @ 0.4 μg DNA | $p < 0.01$ | — | $p < 0.05$ |
| + BAE-DMRIE @ 50 μg DNA | $p < 0.01$ | | |
| + BAE-DMRIE @ 10 μg DNA | $p < 0.01$ | | |
| + BAE-DMRIE @ 2 μg DNA | $p < 0.05$ | | |
| + BAE-DMRIE @ 0.4 μg DNA | NS | | |

[1]At the equivalent DNA dose. Statistical analysis of the tumor volume at Day 22 post tumor injection using the 2-tailed t-TEST for samples with unequal volume, NS = not statistically significant.

Conclusions: A dose dependent and statistically significant tumor reduction was achieved in mice treated with 50, 10, 2, and 0.4 μg of the IL-2 plasmid DNA formulated with or without lipid as compared to normal saline. At the highest DNA dose of 50 μg, there was no significant difference in the tumor reduction when the DNA was administered with or without lipid. A lipid dependent enhancement of the anti-tumor response was observed at the lower DNA doses (10 μg and 2 μg), but only with the cationic lipid, DMRIE/DOPE. βAE did not enhance the antitumor response of the plasmid DNA at any of the DNA dose levels tested.

iii. Dose Regimen

Objectives: The study objective was to determine the optimum injection regimen for the IL-2 plasmid DNA in the B16 model. Injection frequencies of 3, 2, and 1 time per week for three weeks were compared. The efficacy endpoint was measured as reduction of tumor volume.

Methods: For preparation of B16 cells for injection and preparation of the IL-2 plasmid DNA refer to i above.

Female C57BL/6 mice (10/group) were injected subcutaneously on the chest with 0.2 mL of B16 melanoma cells at $1.0\times10^5$ cells/mL for a total $2\times10^4$ cells. Twenty four hours post tumor injection, mice were treated for three consecutive weeks by direct intratumor injection with 100 μl according to the following regimen:

1. IL-2 plasmid (50 μg)±DMRIE/DOPE 3×per week;
2. IL-2 plasmid (50 μg)±DMRIE/DOPE 2×per week;
3. IL-2 plasmid (50 μg)±DMRIE/DOPE 1×per week;
4. IL-2 plasmid (10 μg)±DMRIE/DOPE 3×per week;
5. IL-2 plasmid (10 μg)±DMRIE/DOPE 2×per week;
6. IL-2 plasmid (10 μg)±DMRIE/DOPE 1×per week; or
7. Saline 3×per week.

Figure 11:
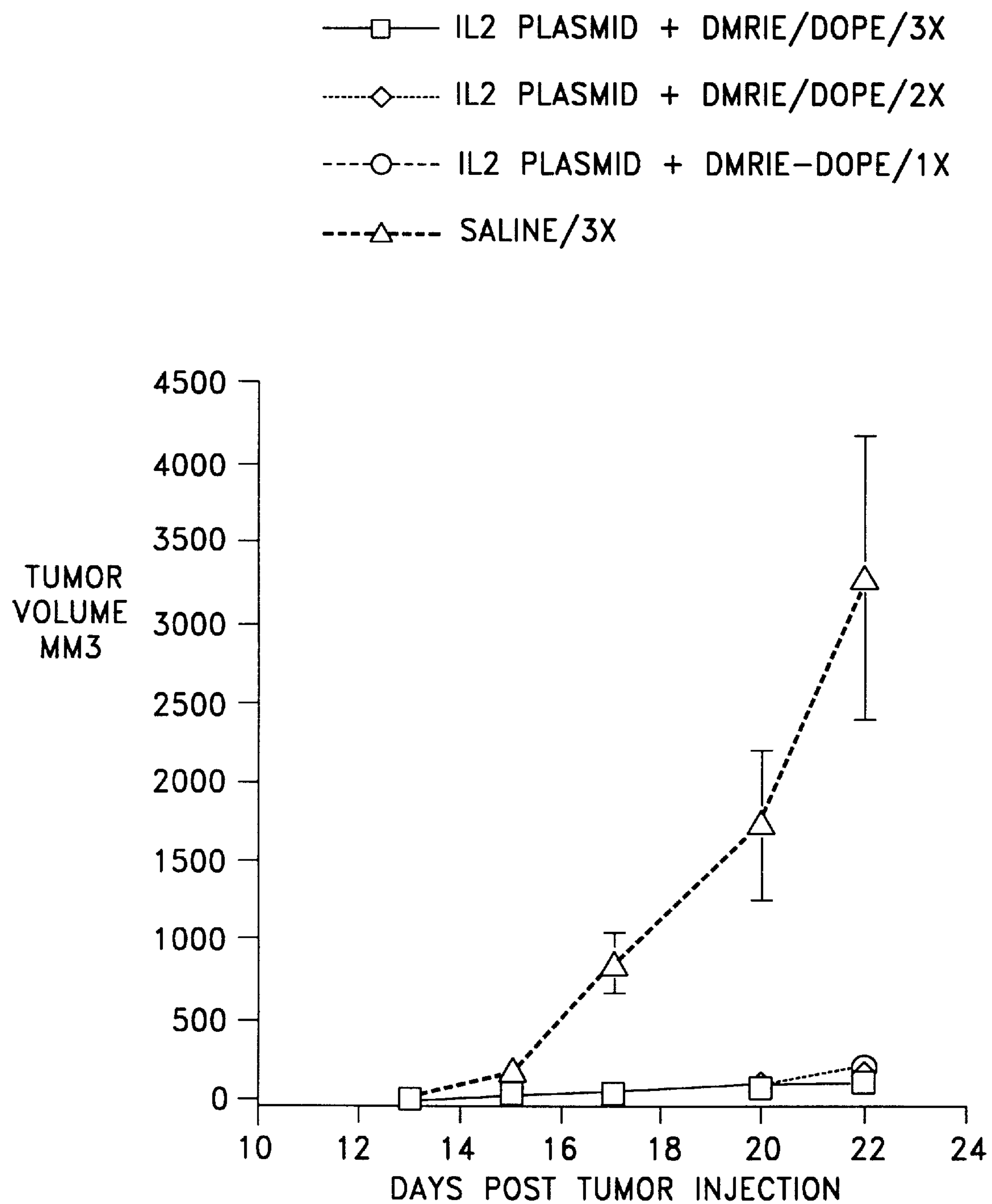
FIG. 11. Tumor growth in B16 melanoma tumor bearing mice treated with IL-2 plasmid DNA plus DMRIE/DOPE at 50 $\mu$g of DNA per injection for 3, 2, and 1 time per week for three consecutive weeks.
Figure 12:
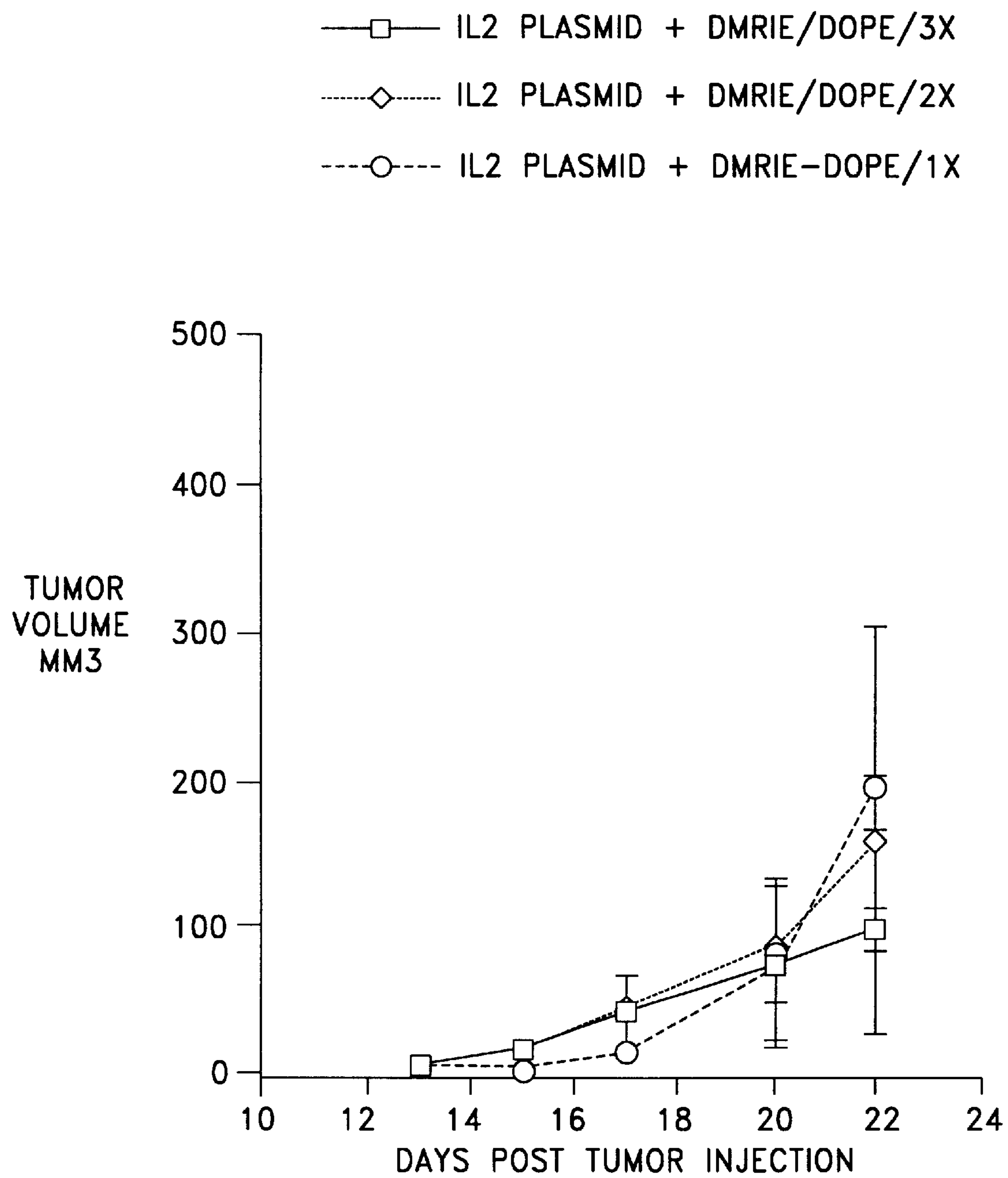
FIG. 12. Tumor growth in B16 melanoma tumor bearing mice treated with IL-2 plasmid DNA plus DMRIE/DOPE at 50 $\mu$g of DNA per injection for 3, 2, and 1 time per week for three weeks after tumor injection.
Figure 13:
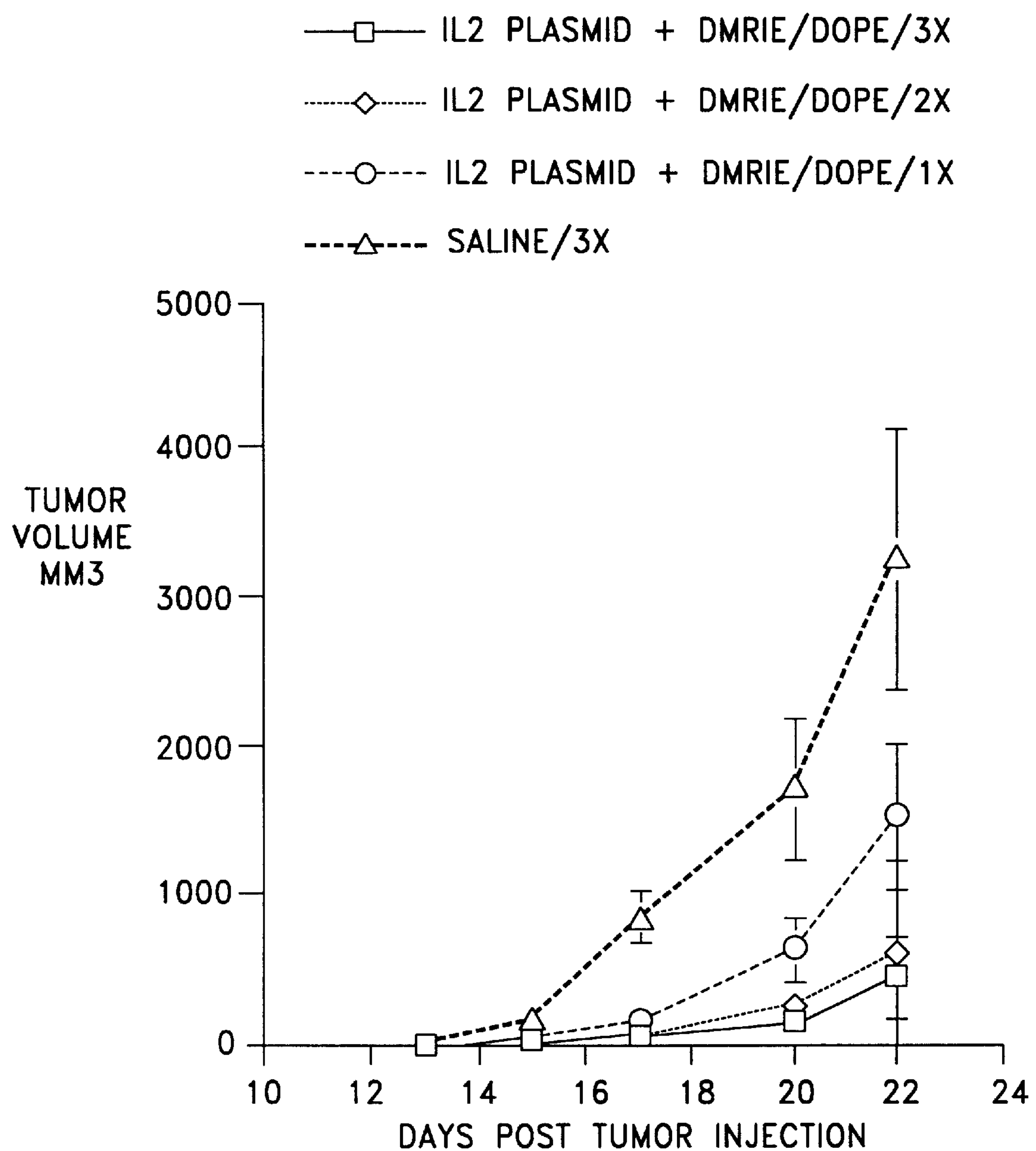
FIG. 13. Tumor growth in B16 melanoma tumor bearing mice treated with IL-2 plasmid DNA plus DMRIE/DOPE at 10 $\mu$g of DNA per injection for 3, 2, and 1 time per week for three consecutive weeks.
Figure 14:
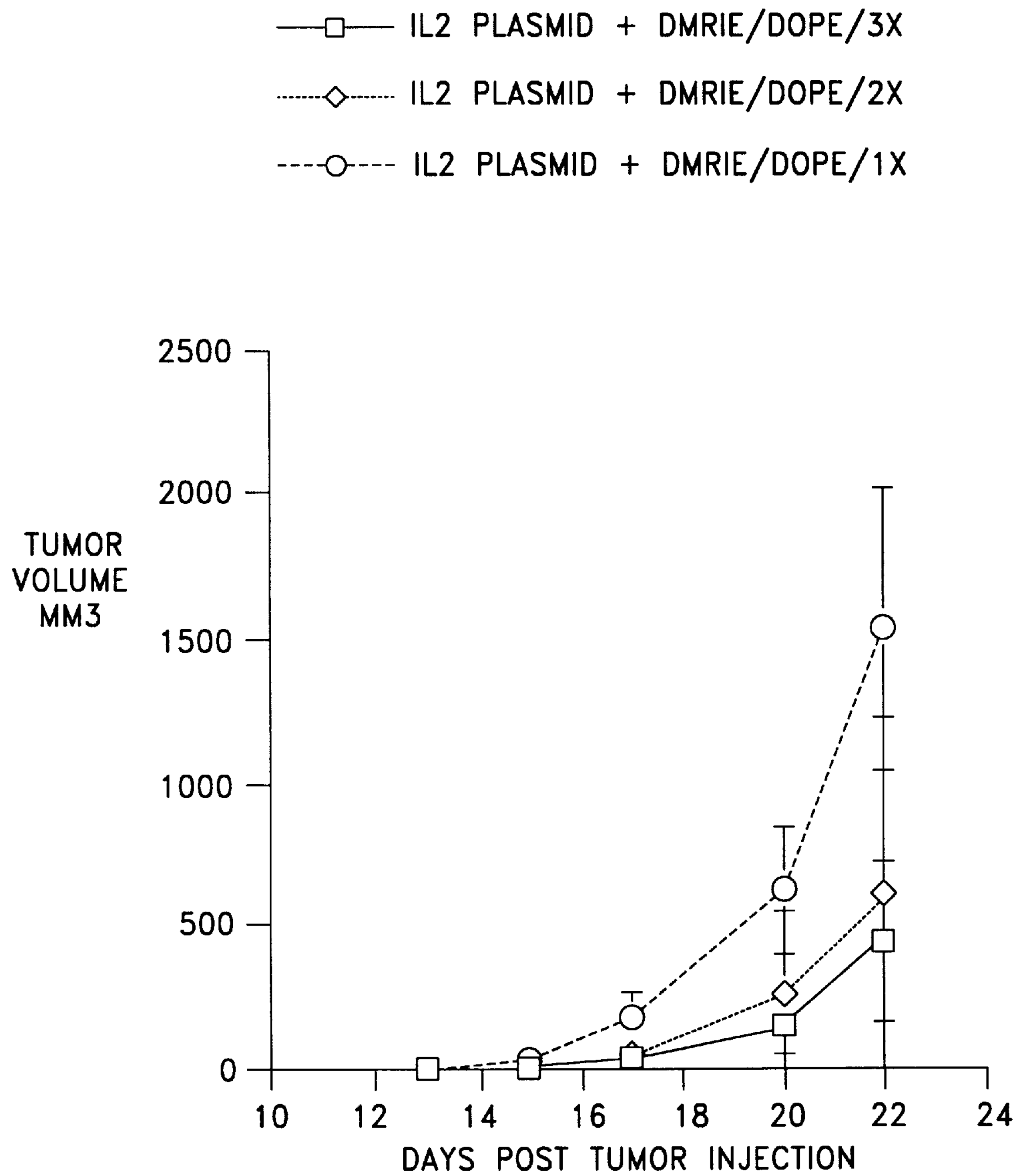
FIG. 14. Tumor growth in B16 melanoma tumor bearing mice treated with IL-2 plasmid DNA plus DMRIE/DOPE at 10 $\mu$g of DNA per injection for 3, 2, and 1 time per week for three weeks after tumor injection.
Figure 15:
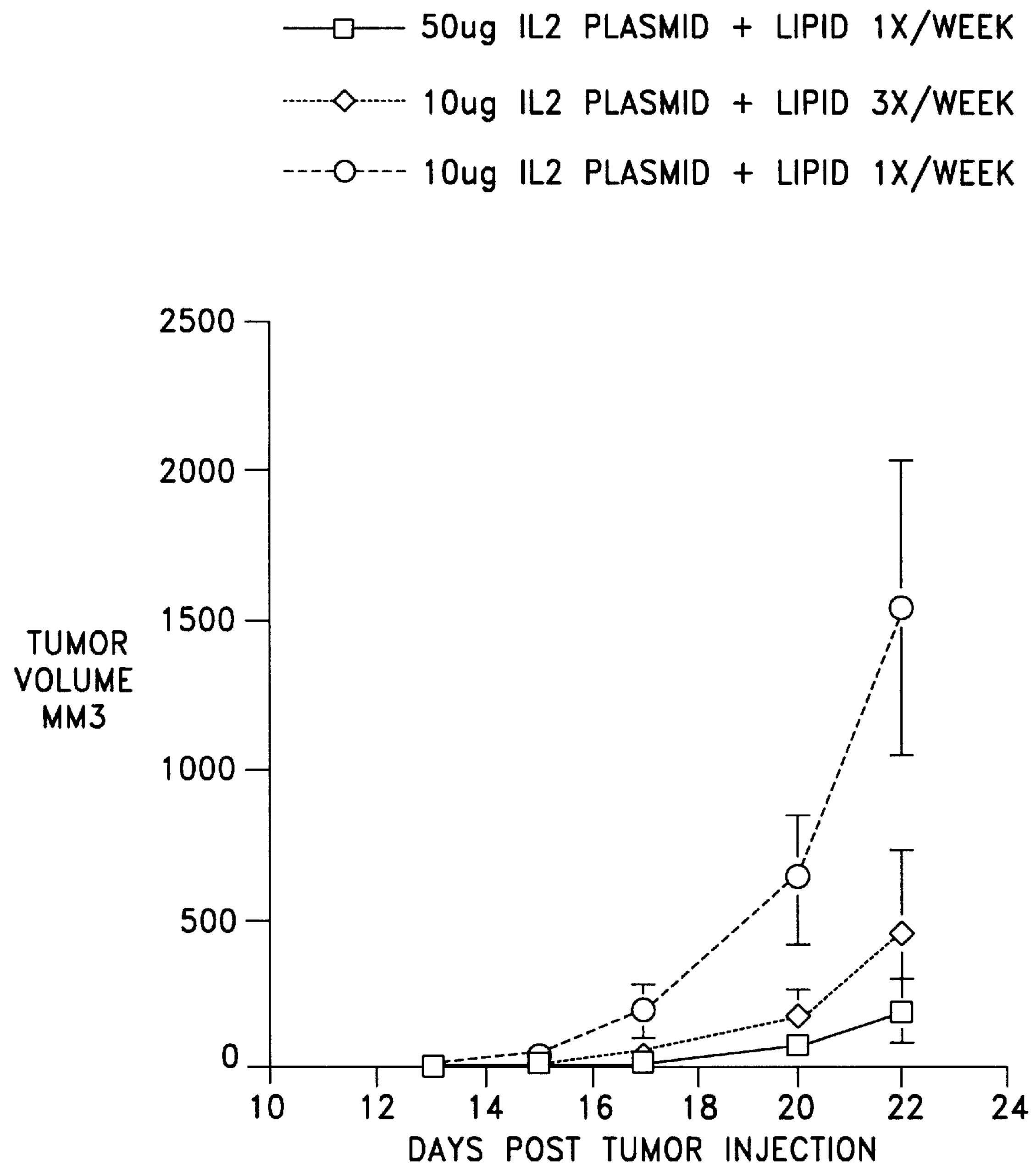
FIG. 15. Tumor growth in B16 melanoma tumor bearing mice treated with IL-2 plasmid DNA formulated with DMRIE/DOPE at 50 $\mu$g and 10 $\mu$g, injected three or one time per week for three consecutive weeks.

Results: A statistically significant antitumor response was observed for intratumor injection at the 50 μg DNA dose regardless of the frequency at which it was administered (FIG. 11). A single weekly injection of 50 μg of DNA was as effective as both 2 and 3 injections per week (FIG. 12). At the 10 μg DNA dose, 2 or 3 injections per week were found to be equally effective in slowing tumor progression (FIG. 13). A single injection of 10 μg of DNA was not found to be effective in preventing tumor progression (FIG. 14). A single injection of 50 μg of DNA per week was comparable to three injections of 10 μg of DNA per week (FIG. 15).

Conclusions: A single injection of 50 μg of the IL-2 plasmid DNA formulated with DMRIE/DOPE was determined to be the optimum dosing regimen in the B16 model.

iv. DNA vs. Protein Therapy

Objectives: The study objective was to compare the anti-tumor activity of the IL-2 plasmid DNA vs. therapy with recombinant IL-2 protein therapy in the B16 melanoma model. The therapy regimen used for the recombinant protein was the protocol that has been demonstrated previously in the literature to result in optimal anti-tumor activity.

Methods: For preparation of B16 cells for injection and preparation of the IL-2 plasmid DNA refer to i above.

Female C57BL/6 mice (10/group) were injected subcutaneously on the chest with 0.2 mL of B16 melanoma cells at $1\times10^5$ cells/mL for a total of $2\times10^4$ cells. Recombinant human IL-2 protein was purchased from Genzyme, Cambridge, Mass. Twenty four hours post tumor injection, mice were treated for three consecutive weeks by direct intratumor injection with 100 μl according to the following regimen:

1. IL-2 plasmid DNA (5μg)±DMRIE/DOPE 3×per week;

2. IL-2 plasmid DNA (50μg)±DMRIE/DOPE 1×per week;

3. rh-IL-2 protein 20,000 units 3×per week; or 4. Saline 3×per week.

Figure 16:
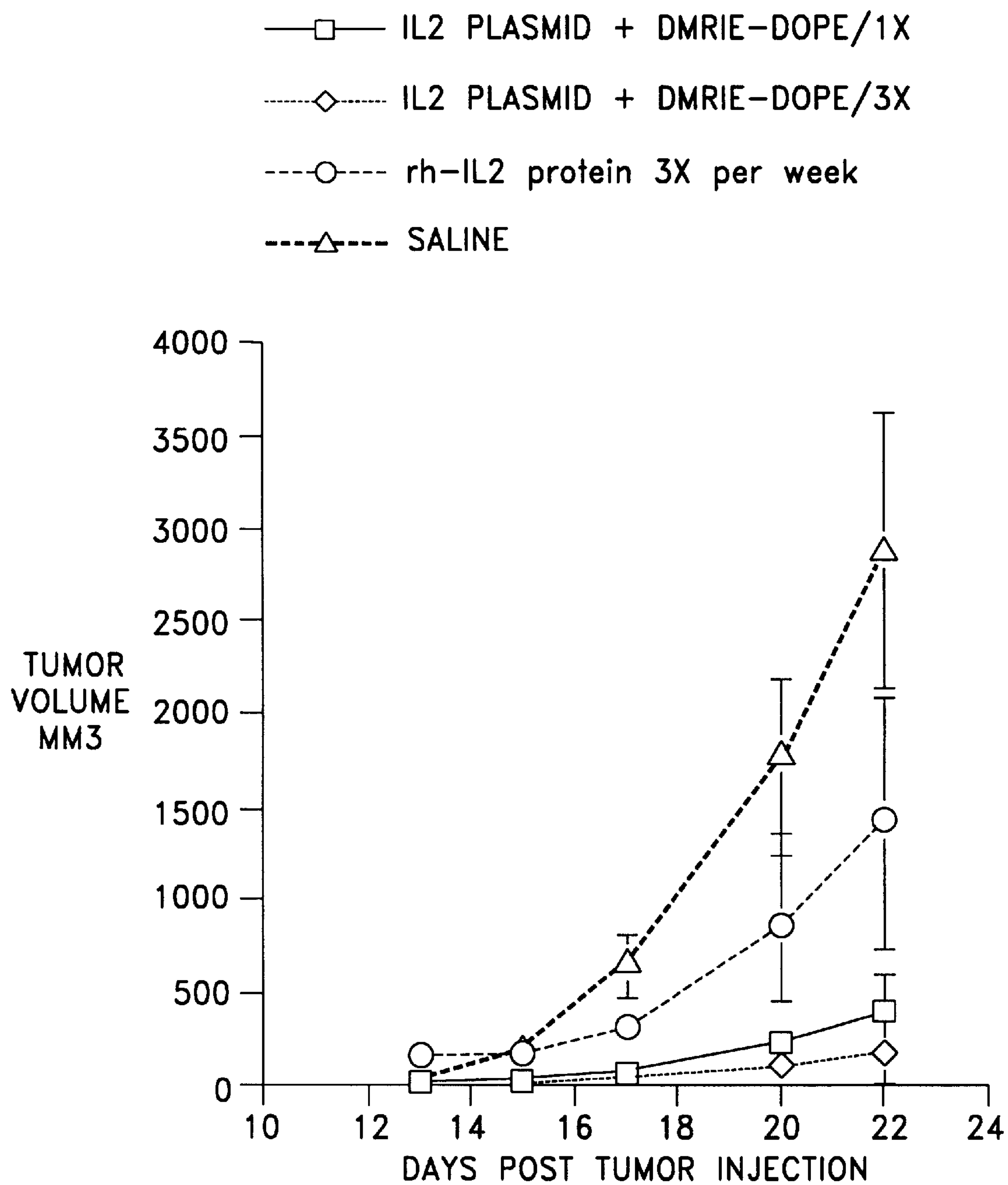
FIG. 16. Comparison of DNA vs. protein therapy.

Results: The treatment of mice either three times or one time per week with the IL-2 plasmid DNA+DMRIE/DOPE slowed tumor progression more effectively than treatment with recombinant IL-2 protein over a period of three weeks (FIG. 16). At the end of the study 22 days post tumor inoculation, DNA treatment resulted in a statistically significant reduction in tumor mass compared to saline ($p<0.01$). The tumor mass in the protein treated animals was not statistically significantly different from either the DNA treated or the saline treated animals. At three weeks post tumor inoculation, 60% of the animals which had received the IL-2 plasmid DNA three times per week remained tumor free and 40% of the animals which had a single weekly injection of the IL-2 plasmid DNA remained tumor free compared to no tumor free animals in the IL-2 protein and saline treated groups.

Conclusions: The IL-2 plasmid DNA administered three times a week for three consecutive weeks was more effective in the B16 model than treatment with 20,000 units of recombinant human Il-2 protein three times a week. Tumor growth was slower in the DNA treated mice and at three weeks post tumor inoculation 60% of the DNA treated animals remained tumor free compared to no tumor free mice in the protein treated group.

v. Efficacy in Renca

Objectives: The study objective was to evaluate the anti-tumor activity of the IL-2 plasmid DNA in another murine tumor model. In this study the murine renal cell adenocarcinoma (Renca) subcutaneous tumor model was evaluated in Balb/c mice.

Methods: Renca cells (Dr. Drew Pardoll, Johns Hopkins University) were prepared for injection according to the same protocol used for the B16 cells, and the IL-2 plasmid DNA was prepared as described in i above.

Figure 17:
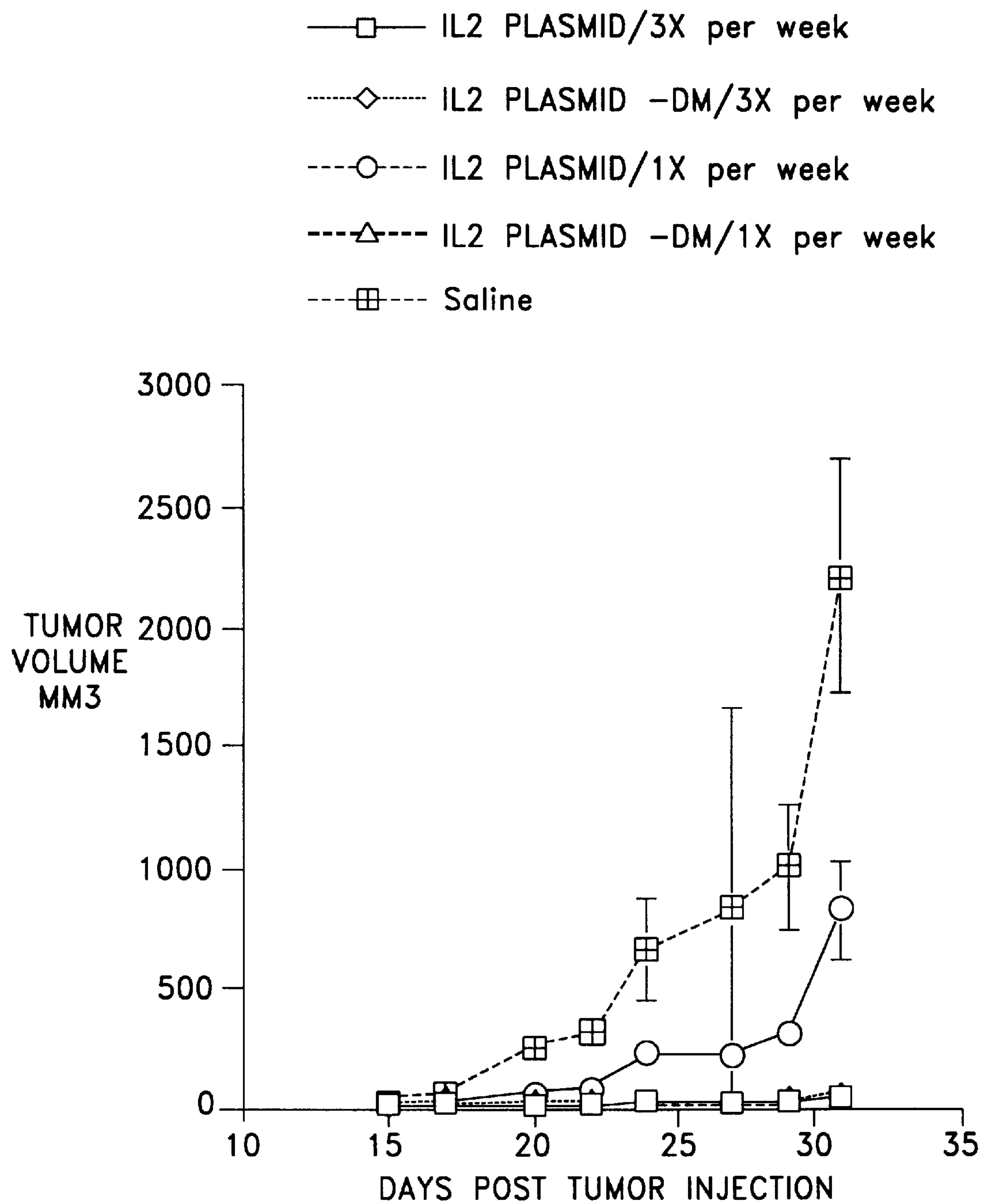
FIG. 17. The effect of IL-2 plasmid DNA alone or formulated with DMRIE/DOPE on the growth of murine renal cell carcinoma.

Female Balb/c mice (10/group) were injected subcutaneously with 0.2 mL of Renca cells for a total $2\times10^4$ cells. Twenty four hours post tumor injection, mice were treated for four consecutive weeks by direct intratumor injection with 100 $\mu$l according to the following regimen:

1. IL-2 plasmid DNA (50 $\mu$g)+DMRIE/DOPE 3×per week;
2. IL-2 plasmid DNA (50 $\mu$g)+DMRIE/DOPE 1×per week; or
3. Saline 3×per week Results: Palpable tumors began to appear 15 days post tumor inoculation in all groups (FIG. 17). Tumor volume was reduced significantly in mice treated with DNA alone or DNA+lipid as compared to the control regardless of the frequency of injection. DNA alone administered three times per week was as effective as DNA+lipid administered either one time or three times per week. A lipid mediated enhancement of the anti-tumor response was observed when DNA was administered one time per week ($p<0.05$ for DNA+lipid vs. DNA alone).

Conclusions: Efficacy as measured by reduction in tumor volume was achieved in the Renca model following direct intratumor injection of the IL-2 plasmid DNA. A lipid mediated enhancement of the anti-tumor response was observed when the IL-2 plasmid DNA was administered as a single weekly injection.

Detection of IL-2 Protein Produced by Tumors Following Direct Intratumor Injection of IL-2 Plasmid DNA in Mice Objectives: IL-2 protein was not detected in the serum of tumor bearing animals that received intratumor injections of the IL-2 plasmid DNA. The failure to detect systemic levels of IL-2 may result from the short in vivo half life of the protein or the expression by the tumors localized to the site of the tumor and the levels secreted by the tumors. Therefore, to determine whether intratumor injection of the IL-2 plasmid DNA could result in the expression of IL-2 protein, experiments were conducted to measure the amount of IL-2 secreted by tumors which were removed from treated animals and cultured in vitro.

Methods: In these experiments mice bearing subcutaneous B16 melanoma tumors received intratumor injection of the IL-2 plasmid DNA, IL-2 plasmid DNA+DMRIE/DOPE, or DMRIE/DOPE daily for three consecutive days (total of three injections) Twenty four hours after the final injection, tumors were removed and cultured in vitro for 72 hours. The culture supernates were collected and screened for human IL-2 by ELISA (Medgenix Diagnostics, Fleurus, Belgium)

Figure 18:
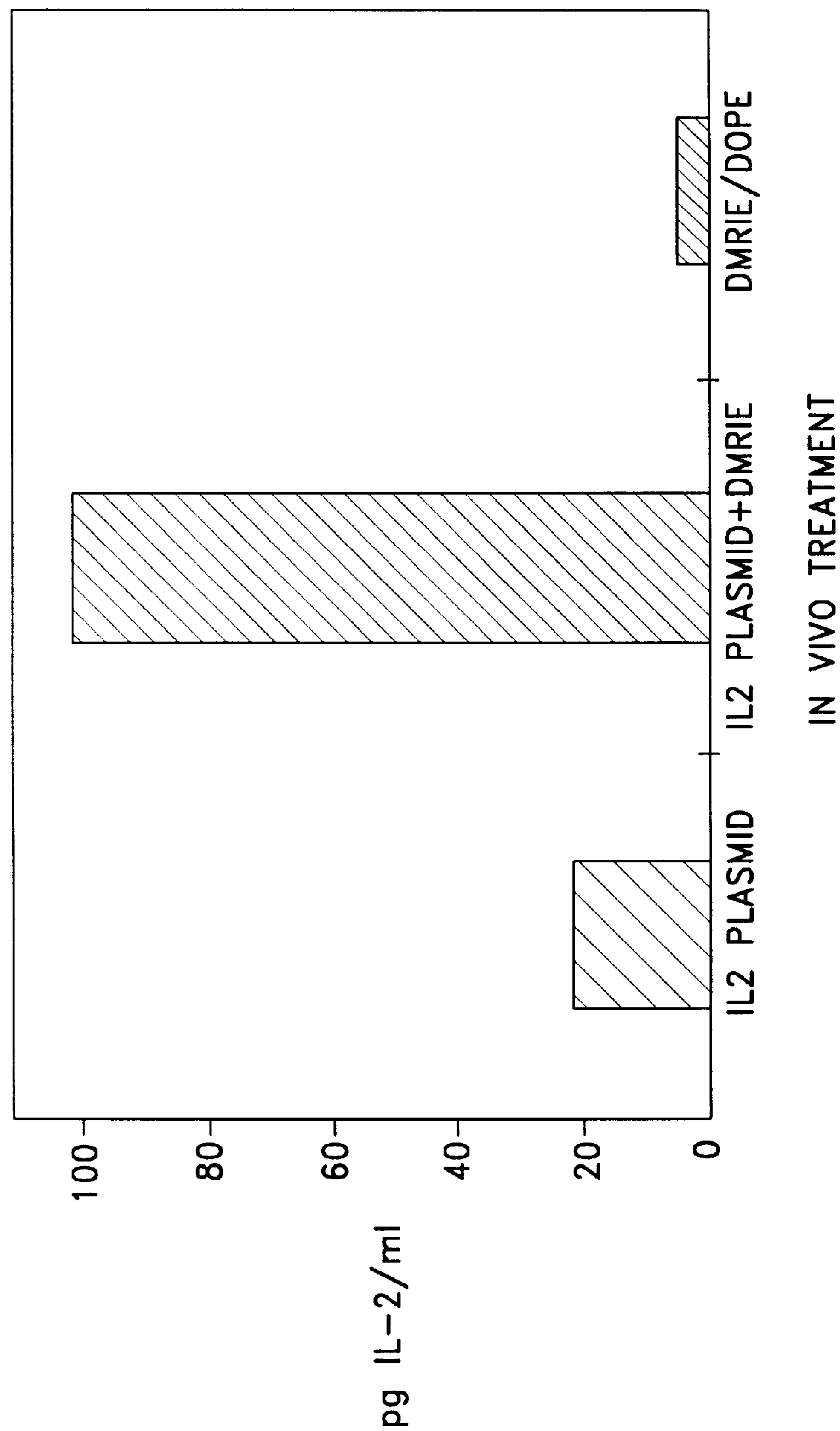
FIG. 18. IL-2 secreted by B16 tumors following in vitro culture.

Results: Tumors that were injected with the IL-2 plasmid DNA secreted approximately 20 pg/mL of IL-2 (FIG. 18). Tumors that were injected with the IL-2 plasmid DNA+DMRIE/DOPE secreted an average of 100 pg/mL of IL-2. Tumors that were injected with DMRIE/DOPE secreted negligible amounts of IL-2.

Conclusions: This data demonstrated that the direct intratumor injection of the IL-2 plasmid DNA resulted in the secretion of IL-2.

In Vitro Transfection of Cells with IL-2 Plasmid DNA

Background: The IL-2 plasmid was designed to effect high level expression of the human IL-2 protein based on relative production of secreted immunoreactive protein by cells grown in culture. Several constructs were made in an effort to develop the DNA component of the IL-2 plasmid. The final product is an IL-2 fusion protein expressed via the cloning of a portion encoding a short segment of the 5' untranslated (UT) region and the first six amino acids of the leader peptide of the rat insulin II gene 5' of the human IL-2 coding sequence minus the first two amino acids (Met-Tyr) of its leader peptide. Changes in this 5' sequence and were found to profoundly affect levels of expression. The best biosynthesis of IL-2 was found to be via a composite mRNA transcriptionally controlled by the cytomegalovirus (CMV) promoter and containing a primary transcript which included, in addition to the IL-2 fusion protein coding region, a large portion of the CMV immediate early 1 gene UT region, including the 800+ bp intron, and a 3' UT region derived from the bovine growth hormone (BGH) gene. Termination and polyadenylation of this eukaryotic cell specific MRNA transcript was via control signals derived from the bovine growth hormone gene.

Various expression plasmid constructs, now viewed as intermediary in the development of the IL-2 plasmid, were tested, comparatively, using an in vitro cell culture based transfection assay. The IL-2 plasmid DNA was chosen as the final drug candidate based on efficiency of expression following in vitro transfection of murine tumor cells. The B16 and Renca cells grown in culture were the same cells used to develop melanoma tumors in vivo, making these test results particularly relevant.

Objectives: To compare the efficacy of human IL-2 expression in cells in culture following transfection using various constructs of plasmid DNA encoding the IL-2 protein. All transfections were carried out using plasmid DNA complexed at defined ratios to the cytofectin, DMRIE/DOPE.

Summary Results: Transient transfection of mouse B16 cells in culture using the IL-2 plasmid resulted in a 10 to 60 fold increase in secreted immunoreactive human IL-2 relative to precursor plasmid constructs.

Description of the In Vitro System: Transient in vitro transfection assays provide a means to compare the relative activities of plasmid DNA constructs and/or cytofectin compounds. It is a rapid and inexpensive method for deriving preliminary information on the efficacy of a new plasmid and/or the efficacy of a plasmid-cytofectin combination. In these assays, actively dividing cells in culture were exposed to DNA-cytofectin complexes for between 3–6 hours. The DNA was subsequently washed away, and the cells were provided with fresh media and allowed to continue growing in culture for a period of 48 hours. For secreted gene products, like IL-2, spent media was collected from these 48 hour cultures and assayed directly for the presence of immunoreactive IL-2 using an ELISA.

Figure 19:
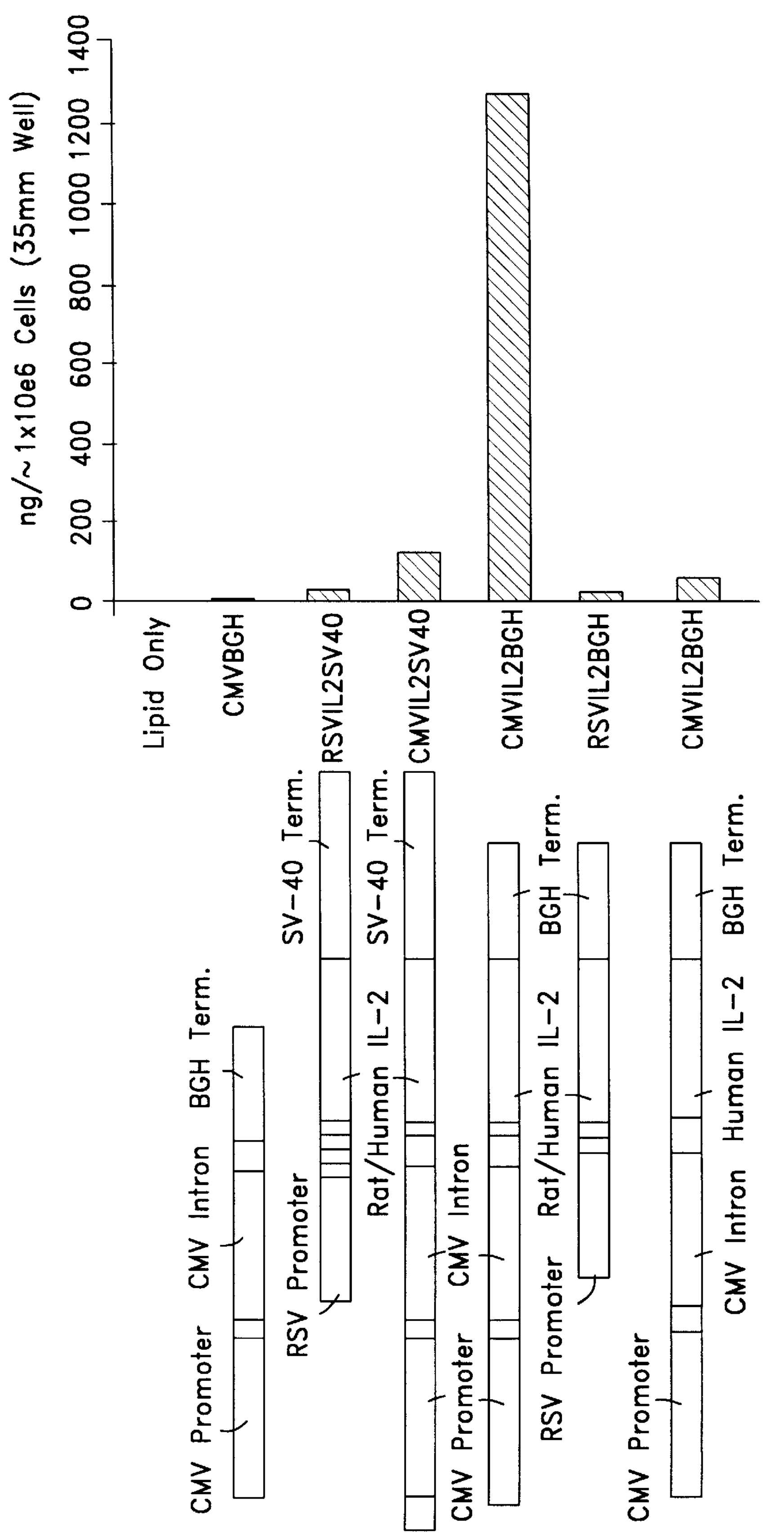
FIG. 19. Human IL-2 Expression in Mouse Melanoma (B16) Cells Transfected with Plasmid DNA.

Materials: The components of the several eukaryotic control elements were tested by constructing the several plasmids diagrammed in FIG. 19. Initially, the Rous Sarcoma Virus 3' LTR (RSV) promoter with the Simian Virus 40 (SV-40) transcriptional terminator/polyadenylation signal sequence were used to express the rat insulin II/IL-2 fusion protein sequence (RSVIL2SV40). A modification of this transcriptional unit was made by substituting the CMV promoter for the RSV promoter in the construct termed CMVIL2SV40. In addition, the SV-40 transcriptional terminator/polyadenylation signal sequence was replaced with the bovine growth hormone gene transcriptional terminator/polyadenylation signal sequence and combined with the CMV promoter in CMVIL2BGH (the IL-2 plasmid of the invention), and with the RSV promoter in RSVIL2BGH. Finally, a construct was made to determine if the components of the rat insulin II gene were effective in fostering high levels of IL-2 expression by replacing the rat insulin II gene sequence with the human IL-2 5' UT and signal peptide sequence (i.e., wild type human IL-2 coding sequence) in the plasmid construct designated CMVLIL2BGH. The control plasmid used in these experiments was CMVBGH, which contains the eukaryotic control elements found in CMVIL2BGH without the human IL-2 coding sequence. These plasmids were harvested from bacterial cells, purified and formulated with DMRIE/DOPE (equimolar ratio). Mouse B16 cells (ATCC #CRL 6322) were obtained and grown in commercial (GIBCO) DMEM media containing 10% fetal calf serum (FCS). An IL-2 ELISA was carried out using commercial reagents and procedures obtained from Medgenix Diagnostics, Fleurus, Belgium.

Methods: 5 μg of supercoiled plasmid DNA formulated with DMRIE/DOPE, at a lipid-to-DNA molar ratio of 2, was added to approximately $5\times10^5$ cells, growing 24 hours in a multi-well culture plate. DNA samples were tested in triplicate. After 4 hours at 37° C., the cells were washed free of DNA and incubated for 48 hours in fresh media. The 48 hour spent media was harvested and tested, following serial dilution, for immunoreactivity using a human IL-2 specific ELISA obtained commercially from Medgenix. Results were normalized to show ng of IL-2 expressed/$10^6$cells/48 hr period.

Results: The ability of CMVIL2BGH, the IL-2 plasmid of the invention, to express secreted human IL-2 protein was compared to an early generation plasmid, RSVIL2SV40, and to 5' and 3' eukaryotic regulatory region modified versions of the CMVIL2BGH plasmid. The results indicated that a combination of these regulatory factors found in CMVIL2BGH resulted in about a 10 fold and, with respect to RSVIL2SV40, about a 60 fold increase in human IL-2 expression. The highest level of expression combined the CMV IE promoter and a portion of the 5' UT region of the CMV IE gene, a portion of the rat insulin II gene 5' UT and signal peptide coding sequence, and the bovine growth hormone gene transcriptional terminator/polyadenylation signal sequence. All comparisons were done using DNAs formulated with DMRIE/DOPE in the transient transfection assay. The controls, using DMRIE/DOPE alone or CMVBGH formulated with DMRIE/DOPE were considered baseline levels of activity using this assay.

Figure 20:
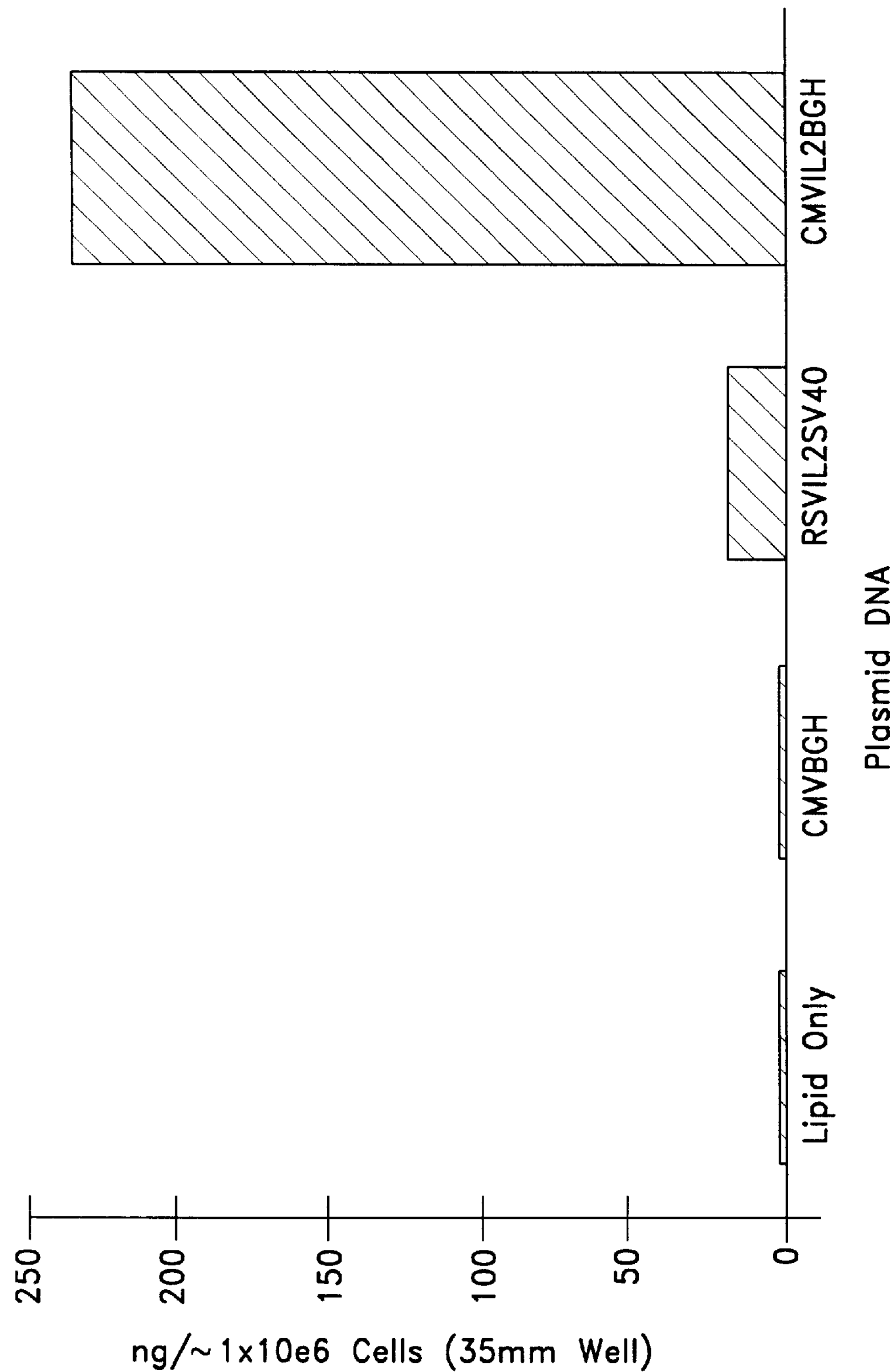
FIG. 20. Human IL-2 Expression in Renca Cells Transfected with Plasmid DNA.
Figure 2I:
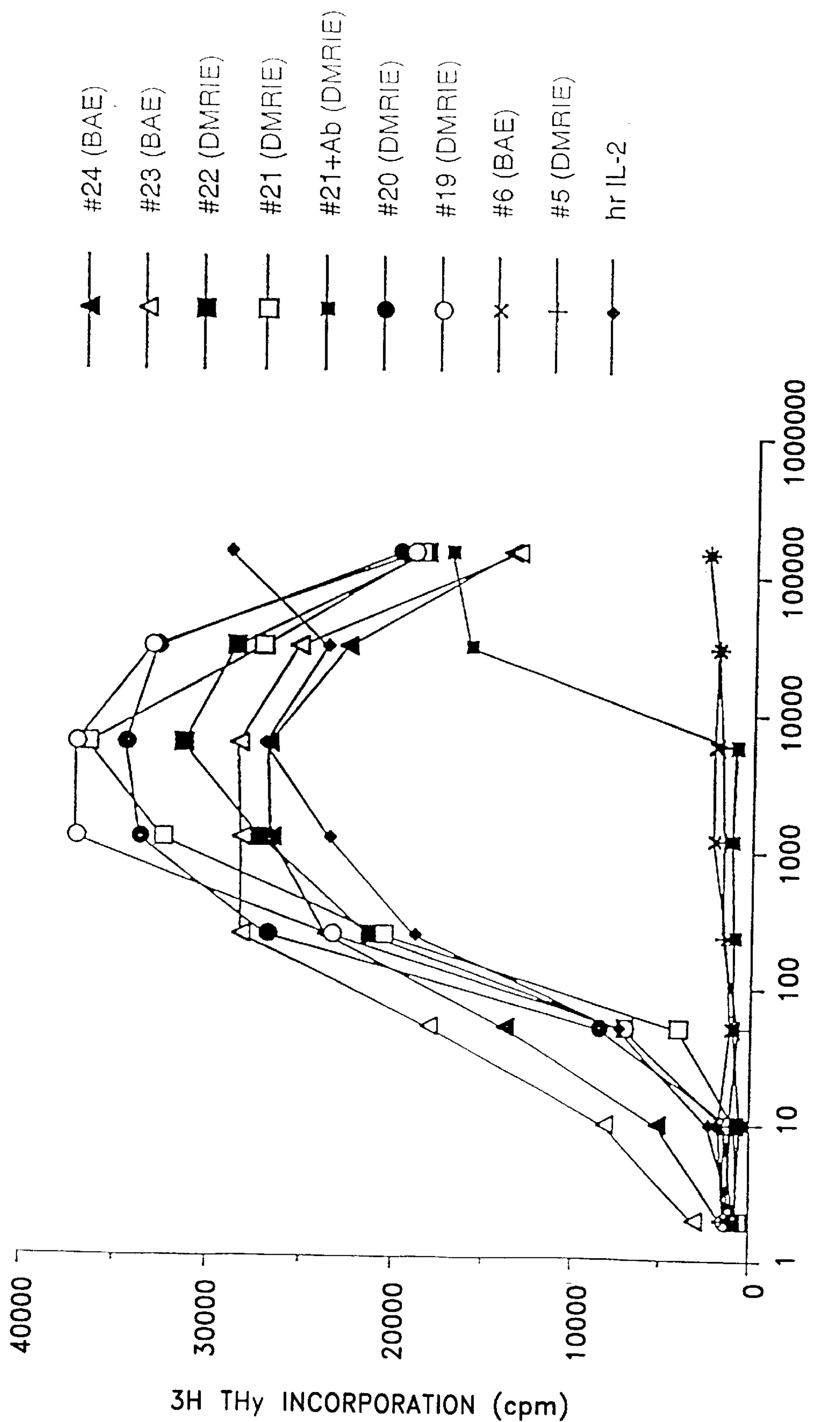

A similar pattern of relative IL-2 immunoreactivity was seen using in vitro transfections of Renca cells (FIG. 20). In general, the Renca cells produced a lower level of transfection based gene activity. This observation was corroborated with a number of expression vectors using reporter genes, such as chloramphenicol acetyl transferase (CAT) and firefly luciferase, as well as with heterologous genes of therapeutic interest. Therefore, the finding was not unexpected that the absolute level of IL-2 secreted into 48 hour media by transfected Renca cells in culture was approximately 1/10th that seen with B16 cells. More importantly, the relative level of expression of CMVIL2BGH, the IL-2 plasmid of the invention, was 10 to 20 fold greater than RSVIL2SV40, similar to that seen with B16 cells.

Conclusions: The results presented above indicated that the IL-2 plasmid, an immunotherapeutic reagent containing the human IL-2 cDNA sequence regulatorily controlled by the CMV promoter and the BGH gene terminator/polyadenylation signal sequence, expressed comparatively high levels of a secreted and immunoreactive human IL-2 protein when introduced into tumorigenic cells grown in culture. This high level of expression was not cell specific in that both Renca and B16 cells exhibited similar results.

Biological Activity of IL-2 in Supernatants of B16 Cells Transfected In Vitro with IL-2 Plasmid DNA Background: The IL-2 plasmid DNA codes for human IL-2. A standard CTLL-2 cell line proliferation assay was utilized to verify the ability of the IL-2 plasmid to transfect cells and to produce biologically active IL-2.

Objectives: To show that supernatants from B16 melanoma cells transfected in vitro with the IL-2 plasmid DNA contained biologically active IL-2, and to quantitate levels of the IL-2 using recombinant IL-2 standards from commercial sources.

Summary Results: Supernatants from B16 cells transfected in vitro with the IL-2 plasmid DNA contained high levels of biologically active IL-2.

Description of the System: Supernatants from transient in vitro transfections of B16 melanoma cells with the IL-2 plasmid DNA were collected 24 hours post transfection and frozen. IL-2 biological activity was quantitated using CTLL-2 cells, an IL-2 dependent murine cell line.

Materials: The IL-2 plasmid (human IL-2 sequence) and CMVBGH (blank plasmid control) were prepared. DMRIE/DOPE and βAE cytofectins were prepared. The CTLL-2 murine T cell line was obtained (ATCC #TIB 214). Recombinant human IL-2 was obtained from R&D Systems (Cat. #202-IL-2). The anti-human IL-2 neutralizing antibody was obtained from R&D Systems (Cat. #AB-202-NA).

Methods: The in vitro transfection of B16 cells with the IL-2 plasmid DNA was described above.

The CTLL-2 cells were maintained in RPMI 1640+10% FCS+1 U of human recombinant IL-2. Cells were fed twice weekly. Dilutions of test samples derived from supernatants of B16 melanoma cells transfected in vitro with the IL-2 plasmid DNA complexed with DMRIE/DOPE or βAE/DMRIE, or recombinant IL-2 standards, with or without neutralizing anti-IL-2 antibody, were made in 96-well plates. $5\times10^4$ CTLL-2 cells in 100 μl of RPMI 1640 per well were added. The plates were incubated at 37° C. for 24 h. 25 μl of RPMI 1640 containing 0.5 μCi of [$^3$H] TdR were added per well, and 4 h later the cells were analyzed for incorporated radioactivity.

Results: Supernatants from B16 cells transfected in vitro with the IL-2 plasmid DNA induced proliferation of CTLL-2 cells (FIG. 21). This activity was abrogated by anti-IL-2 antibody. DMRIE-DOPE and βAE cytofectins were both effective as transfection facilitators. Supernatants from cells transfected with the control plasmid in presence of lipids did not induce proliferation of CTLL-2 cells. Comparison of IL-2 containing supernatants and standard recombinant IL-2 showed very similar bioactivity for both IL-2s on the per unit of weight basis.

Conclusions: The IL-2 plasmid DNA transfected B16 cells and induced secretion of biologically active IL-2.

Pharmacokinetics: Blood half-life and Tissue Distribution of IL-2 Plasmid DNA

Experiments are conducted to determine the blood half-life and tissue distribution of DNA following intravenous administration in mice. The intravenous route of administration is chosen for these studies because this route has the greatest potential for the manifestation of systemic toxicity. Therefore, the kinetics of degradation in the blood (half-life) and the tissue distribution of DNA over time are determined.

Effects of Direct Intrahepatic Injection of IL-2 Plasmid DNA

Experiments are conducted to determine the consequences of the transfection of normal tissue. The study is designed to evaluate the effects of the direct intrahepatic injection of the IL-2 plasmid DNA. At various time points following intrahepatic administration of the IL-2 plasmid DNA, mice are necropsied and analyzed for clinical biochemistry and liver histopathology.

Methods: A single vial formulation of the IL-2 plasmid DNA+DMRIE/DOPE (DNA/lipid mass ratio of 5:1) is prepared as described above.

10 male and 10 female mice/group receive a direct intrahepatic injection into the left lateral lobe of the liver of 20 μl of the IL-2 plasmid DNA (1 or 10 μg of plasmid DNA) using a 28 gauge needle with a depth limiting collar of 3 mm. Injections of non-anesthetized mice are targeted to the center of the left lateral lobe by first penetrating the flap of the medial lobe. 10 male and 10 female mice/time point receive a similar injection of 20 μl of the injection vehicle and serve as the vehicle controls. Additional groups, 10 mice per sex/group, receive a series of 2 weekly intrahepatic injections of 20 μl of the IL-2 plasmid DNA (10 μg of plasmid DNA) or 4 weekly intrahepatic injections of 20 μl of the IL-2 plasmid DNA (1 or 10 μg of plasmid DNA).

Anesthetized animals are exsanguinated by cardiac puncture and serum and blood samples are obtained as outlined in the table below. Serum and blood samples are analyzed. Serum is analyzed for serum alanine aminotransferase (ALT), serum aspartate aminotransferase (AST), creatinine (CREA), lactate dehydrogenase (LDH), blood urea nitrogen (BUN), and alkaline phosphatase (ALP) and total bilirubin. Blood is analyzed for RBC, WBC, platelets, hemoglobin, hematocrit, and red cell indices.

Upon necropsy, the injected livers are examined in situ, removed and put into formalin for histopathology. One uninjected lobe from each animal is also removed and put into formalin for histopathology.

Safety

The IL-2 plasmid DNA was evaluated for safety in an acute study in mice and in repeat dose studies in mice and cynomolgus monkeys. Drug safety studies were performed in mice and cynomolgus monkeys by intravenous administration of DNA. This route of administration was chosen because it has the greatest potential to manifest systemic toxicity. In an acute safety study in mice, the IL-2 plasmid DNA was administered as a single intravenous dose of 0.1, 1.0, 10 or 50 μg of plasmid DNA, and mice were observed for 14 days. In a repeat dose study in mice, animals received repeat iv injections three times per week for four consecutive weeks (12 total injections) of 0.1, 1.0 or 10 μg of plasmid. Half of the mice from each group were necropsied 24 hours after the final dose (terminal necropsy) and the remaining mice remained on study, untreated, for an additional 28 days to determine the reversibility, persistence, or delayed occurrence of toxic effects. Cynomolgus monkeys are to receive a series of iv injections once a week for six consecutive weeks (6 total injections) of the IL-2 plasmid DNA (300 μg of plasmid per injection). Animals are to be necropsied 24 hours after the final dosing and an additional recovery group is to remain on study, untreated, for an additional 28 days to determine the reversibility, persistence, or delayed occurrence of toxic effects.

The following table shows a comparison of the doses that are to be used in the pre-clinical safety studies vs. the proposed human doses.

TABLE

COMPARISON OF PLASMID DNA DOSES USED IN THE PRE-CLINICAL SAFETY STUDIES VS. THE PROPOSED HUMAN DOSE

| | EQUIVALENT HUMAN DOSE[1] |
|---|---|
| ACUTE-MICE DOSE | |
| 0.1 μg | 0.2 X |
| 1.0 μg | 2 X |
| 10 μg | 20 X |
| 50 μg | 100 x |
| REPEAT DOSE-MICE DOSE | |
| 0.1 μg × 12 | 2.3 X |
| 1.0 μg × 12 | 23 X |
| 10 μg × 12 | 230 X |
| REPEAT DOSE-MONKEY DOSE | |
| 300 μg × 6 | 35 x |

[1]Based on a cumulative human dose of 1.8 mg/kg adult and assuming an average mouse weight of 20 g and an average cynomolgus monkey weight of 2.0 kg.

The cumulative doses administered in the drug safety studies range from 0.2 to 230 times the proposed human dose.

Acute Intravenous Safety Study of IL-2 Plasmid DNA in Mice

Experiments were conducted to evaluate the safety of intravenous administration of the IL-2 plasmid DNA in mice. The test article, a plasmid DNA/lipid complex, was prepared by mixing the IL-2 plasmid DNA, a plasmid DNA coding for the human IL-2 gene, formulated in injection vehicle, with DMRIE/DOPE lipid reconstituted in injection vehicle. The test article was administered as a single intravenous bolus injection to four groups of mice (5/sex/group) at DNA dose levels of 0.1, 1.0, 10 and 50 μg of plasmid DNA at a constant dose volume of 0.1 mL/mouse. An additional group of 20 mice (10 males and 10 females) received 0.1 mL of injection vehicle and served as the vehicle control. The administration of a single intravenous dose of the IL-2 plasmid DNA ( 0.1, 1.0, 10 and 50 μg of plasmid DNA) did not produce any signs of acute toxicity nor signs of residual toxicity in mice over a fourteen day observation period.

Fourteen Day Repeat Dose Study of IL-2 Plasmid DNA in Mice

Experiments were performed to determine the safety of repeated daily intravenous administration of the IL-2 plasmid DNA in mice three times a week for four consecutive weeks. In addition, a recovery group for each dose level remained on study, untreated for an additional 28 days to determine the reversibility, persistence, or delayed occurrence of any effects.

The test article, a plasmid DNA/lipid complex, was prepared by mixing the IL-2 plasmid DNA, a plasmid DNA coding for the human IL-2 gene, formulated in injection vehicle, with DMRIE/DOPE lipid reconstituted in injection vehicle. The test article was administered three times a week for four weeks as an intravenous injection to four groups of mice (10 males and 10 females/group) at dose levels of 0.1, 1.0, 10 μg of plasmid DNA at a constant dose volume of 0.1 mL mouse. An additional group of twenty mice (10 males and 10 females) receive 0.1 mL of injection vehicle and served as the vehicle control. Five males and five females from each group were sacrificed 72 hours following the final IL-2 plasmid DNA injection (terminal necropsy), and the remaining mice were kept as a recovery group (recovery necropsy).

The data presently available from this study is from the hematological analysis at days 31 and 56. The hematology results from the mice analyzed on day 31 (72 hours post final injection) are summarized in the table below. A statistically significant increase in the WBC counts was observed for the male 10 μg dose group ($p<0.05$) and for all of the dosed female groups ($p<0.01$). This increase in WBC counts was primarily due to significant increases in the lymphocyte populations from these animals. A statistically significant increase in the monocyte counts was observed for the male 0.1 μg dose group ($p<0.05$) and the female 10 μg dose group ($p<0.01$). A statistically significant increase was also observed for the basophil counts for the female 0.1 and 10 μg dose groups ($p<0.01$). There was no effect on the neutrophil or eosinophil counts. No effects on hematology were observed on day 56 after the 28 day post dosing recovery period.

The repeated administration of the IL-2 plasmid DNA resulted in a significant increase in the WBC counts for both the male and female groups with the effect being most pronounced in the female animals. The increase in WBC counts was primarily a result of increases in the lymphocyte counts. In the case of the female animals, the number of lymphocytes almost doubled as compared to the vehicle control group. The effects of other WBC subsets such as the monocytes and basophils were not as dramatic and may be incidental. These effects were transitory and were no longer observed following a 28 day post dosing recovery period. The elevated lymphocyte counts may have resulted from systemic IL-2 secretion following DNA injection. It is interesting to note that the effect was most evident for the lymphocytes, cells normally responsive to IL-2.

Twenty-eight Day Repeat Dose Study of IL-2 Plasmid DNA in Cynomolgus Monkeys (*Maccaca fascicularis*)

Experiments are conducted to provide safety information on the IL-2 plasmid DNA when administered as weekly intravenous injections for 6 consecutive weeks to cynomolgus monkeys, and to include a 28 day post dose observation/recovery period in selected animals. The intravenous route is chosen because this route has the greatest potential for manifestation of systemic toxicity. This old world primate is selected because it should maximize the likelihood of the occurrence of toxic responses which are quantitatively similar to those which may be expected in humans.

A single intravenous injection of 1.0 mL of the IL-2 plasmid DNA is administered to 5 males and 5 females on Days 1, 8, 15, 22, 29 and 36 (the first day of dosing is designated as Day 1). This results in a single dose of 300 μg of plasmid DNA and a cumulative dose of 1.8 mg of plasmid DNA. An additional 5 males and 5 females receive 1.0 mL of injection vehicle on Days, 1, 8, 15, 22, 29, and 36 and serve as the vehicle control. Blood samples are collected for clinical chemistry and hematology pre-study and on days 7, 14, 21, 28, 35, 42, 49, 56. Three monkeys/group/sex are necropsied on day 37 (24 hours post final injection) and the remaining 2 monkeys/group/sex remain on study for an additional 28 days.

While particular embodiments of the invention have been described in detail, it will be apparent to those skilled in the art that these embodiments are exemplary rather than limiting, and the true scope of the invention is that defined within the attached claims.

IL-2 PLASMID DNA REPEAT DOSE SAFETY STUDY: HAMATOLOGY DAY 31

| Dose | WBC $10^3/mm^3$ | Lymph $10^3/mm^3$ | Neut $10^3/mm^3$ | Mono $10^3/mm^3$ | Eos $10^3/mm^3$ | Baso $10^3/mm^3$ |
|---|---|---|---|---|---|---|
| | | | MALES | | | |
| 0 | 8.68 ± 2.60 | 6.47 ± 1.84 | 1.61 ± 0.87 | 0.28 ± 0.12 | 0.14 ± 0.08 | 0.05 ± 0.02 |
| 0.1 μg | 6.06 ± 1.46 | 4.64 ± 0.96 | 0.96 ± 0.24 | 0.13 ± 0.05* | 0.24 ± 0.38 | 0.03 ± 0.01 |
| 1.0 μg | 9.98 ± 2.39 | 7.65 ± 1.77 | 1.64 ± 0.66 | 0.19 ± 0.07 | 0.18 ± 0.06 | 0.05 ± 0.03 |
| 10 μg | 13.30 ± 1.63* | 11.22 ± 2.55** | 1.36 ± 0.18 | 0.25 ± 0.08 | 0.18 ± 0.03 | 0.08 ± 0.02 |
| | | | FEMALES | | | |
| 0 | 6.29 ± 2.68 | 4.62 ± 2.21 | 0.91 ± 0.34 | 0.15 ± 0.07 | 0.37 ± 0.63 | 0.05 ± 0.02 |
| 0.1 μg | 13.10 ± 1.62** | 10.76 ± 1.38** | 1.56 ± 0.26 | 0.22 ± 0.03 | 0.29 ± 0.26 | 0.11 ± 0.02** |
| 1.0 μg | 11.46 ± 1.14** | 9.16 ± 0.55** | 1.61 ± 0.78 | 0.24 ± 0.03 | 0.23 ± 0.10 | 0.05 ± 0.01 |
| 10 μ | 12.69 ± 1.75** | 9.27 ± 1.66** | 2.51 ± 1.63 | 0.31 ± 0.08** | 0.30 ± 0.16 | 0.08 ± 0.01 |

White blood cell (WBC), lymphocyte (Lymph), neutrophil (Neut), monocyte (Mono), eosinophil (Eos), and basophil (Bas) counts.
*$p < 0.05$,
**$p < 0.01$

What is claimed is:

1. A method for treating cancer in a human patient, comprising:

administering in vivo directly into a tumor of said patient a DNA plasmid formulated with a cationic lipid;

wherein said plasmid comprises:

(1) a first polynucleotide encoding a mature human interleukin 2 (IL-2) polypeptide;

(2) a second polynucleotide encoding a peptide leader operably linked to said first polynucleotide, wherein said peptide leader directs secretion of said IL-2; and (3) a promoter operably associated with said first and second polynucleotides;

wherein said plasmid and cationic lipid are administered in an amount sufficient that uptake of said plasmid into the cells of said tumor occurs, and sufficient expression and secretion of said IL-2 results, to reduce tumor growth.

2. The method of claim 1, wherein said promoter is a CMVIE promoter.

3. The method of claim 1, wherein said plasmid further comprises a transcriptional terminator and polyadenylation signal sequence from the bovine growth hormone (BGH) gene positioned 3' and in operable association with said first polynucleotide encoding mature human IL-2.

4. The method of claim 1, wherein said peptide leader is the native human IL-2 peptide leader.

5. The method of claim 1, wherein said peptide leader is identical to the native human IL-2 peptide leader with the following exception, the first two amino acids at the amino terminal end of said native human IL-2 peptide leader are replaced with Met-Ala-Leu-Trp-Ile-Asp (SEQ ID NO:3).

6. The method of claim 1, wherein said plasmid and said cationic lipid formulation are present at a ratio from 9:1 to 1:9.

7. The method of claim 6, wherein said ratio is 5:1.

8. The method of claim 1, wherein said cationic lipid formulation comprises both positively charged lipids and neutral lipids.

9. The method of claim 1, wherein said cationic lipid formulation comprises DMRIE.

10. The method of claim 1, wherein said cationic lipid formulation comprises DOPE.

11. The method of claim 1, wherein said cationic lipid formulation comprises DMRIE and DOPE.

12. The method of claim 11, wherein DMRIE and DOPE are present at a ratio of 1:1.

13. The method of claim 1, wherein said cancer is melanoma.

14. The method of claim 1, wherein said cancer is renal cell carcinoma.

15. The method of claim 5, wherein said cancer is melanoma.

16. The method of claim 5, wherein said cancer is renal cell carcinoma.

17. The method of claim 8, wherein said cancer is melanoma.

18. The method of claim 8, wherein said cancer is renal cell carcinoma.

19. The method of claim 9, wherein said cancer is melanoma.

20. The method of claim 9, wherein said cancer is renal cell carcinoma.

21. The method of claim 11, wherein said cancer is melanoma.

22. The method of claim 11, wherein said cancer is renal cell carcinoma.

23. The method of claim 12, wherein said cancer is melanoma.

24. The method of claim 12, wherein said cancer is renal cell carcinoma.

* * * * *